United States Patent
Asako

(10) Patent No.: US 10,364,448 B2
(45) Date of Patent: Jul. 30, 2019

(54) METHOD FOR PRODUCING L-α-AMINO ACID COMPOUND

(71) Applicant: Sumitomo Chemical Company, Limited, Chuo-ku, Tokyo (JP)

(72) Inventor: Hiroyuki Asako, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 96 days.

(21) Appl. No.: 15/325,190

(22) PCT Filed: Jul. 2, 2015

(86) PCT No.: PCT/JP2015/069105
§ 371 (c)(1),
(2) Date: Jan. 10, 2017

(87) PCT Pub. No.: WO2016/006521
PCT Pub. Date: Jan. 14, 2016

(65) Prior Publication Data
US 2017/0191097 A1    Jul. 6, 2017

(30) Foreign Application Priority Data
Jul. 11, 2014    (JP) .................. 2014-143021

(51) Int. Cl.
| | | |
|---|---|---|
| C12P 13/12 | (2006.01) | |
| C12P 11/00 | (2006.01) | |
| C12P 13/04 | (2006.01) | |
| C12N 15/09 | (2006.01) | |
| C12P 9/00 | (2006.01) | |
| C12P 7/40 | (2006.01) | |
| C12N 5/10 | (2006.01) | |
| C12N 9/06 | (2006.01) | |

(52) U.S. Cl.
CPC ............ *C12P 13/12* (2013.01); *C12N 5/10* (2013.01); *C12N 9/0016* (2013.01); *C12N 15/09* (2013.01); *C12P 7/40* (2013.01); *C12P 9/00* (2013.01); *C12P 11/00* (2013.01); *C12P 13/04* (2013.01); *C12Y 102/01002* (2013.01); *C12Y 104/01009* (2013.01); *C12Y 111/01006* (2013.01)

(58) Field of Classification Search
CPC . C12P 13/12; C12P 11/00; C12P 13/04; C12P 9/00; C12P 7/40; C12Y 111/01006; C12Y 102/01002; C12Y 104/01009; C12N 9/0016; C12N 15/09; C12N 5/10
See application file for complete search history.

(56) References Cited

U.S. PATENT DOCUMENTS

| | | |
|---|---|---|
| 4,782,020 A | 11/1988 | Leuchtenberger et al. |
| 4,824,781 A | 4/1989 | Hummel et al. |
| 2006/0063238 A1 | 3/2006 | Hummel et al. |
| 2010/0028959 A1 | 2/2010 | Kanamaru et al. |
| 2011/0281309 A1 | 11/2011 | Kanamaru et al. |

FOREIGN PATENT DOCUMENTS

| | | |
|---|---|---|
| JP | S55-102557 A | 8/1980 |
| JP | S60-041495 A | 3/1985 |
| WO | 2012036302 A1 | 3/2012 |

OTHER PUBLICATIONS

Strnad et al., GenBank accession No. ADP14612, Jan. 18, 2011.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Int'l Search Report dated Oct. 6, 2015 in Int'l Application No. PCT/JP2015/069105.
Written Opinion dated Oct. 6, 2015 in Int'l Application No. PCT/JP2015/069105.
Ferjancic-Biagini et al, "In Vitro Oxidative Decarboxylation of L-2-Hydroxy-4-Methylthiobutanoic Acid by L-2-Hydroxy Acid Oxidase A from Chicken Liver," Biochimie, vol. 77, pp. 249-255 (1995).
Ding et al, "Characterization of a Thermally Stable and Organic Solvent-Adaptative NAD+-Dependent Formate Dehydrogenase from *bacillus* sp. F1," Journal of Applied Microbiology, vol. 111, pp. 1075-1085 (2011).
Triggs-Raine et al, "Nucleotide Sequence of katG, Encoding Catalase HPI of *Escherichia coli*," Journal of Bacteriology, vol. 170, No. 9, pp. 4415-4419 (1988).
Katoh et al, "Cloning and Sequencing of the Leucine Dehydrogenase Gene from Bacillus Sphaericus IFO 3525 and Importance of the C-Terminal Region for the Enzyme Activity," Journal of Molecular Catalysis B: Enzymatic, vol. 23, pp. 239-247 (2003).
Kataoka et al, "Alteration of Substrate Specificity of Leucine Dehydrogenase by Site-Directed Mutagenesis," Journal of Molecular Catalysis B: Enzymatic, vol. 23, pp. 299-309 (2003).
Search Report and Written Opinion dated Nov. 21, 2017 in SG Application No. 11201700099P.
Uniprot-E3HN95, "FMN-Dependent Alpha-Hydroxy Acid Dehydrogenase Family Protein 1," Jan. 11, 2011, downloaded from web page: http://www.uniprot.org/uniprot/E3HN95, Download date: Feb. 21, 2018, 4 pages.
Uniprot-J4PD10, "FMN-Dependent Alpha-Hydroxy Acid Dehydrogenase Family Protein 1," Oct. 31, 2012, downloaded from web page: http://www.uniprot.org/uniprot/J4PD10#, Download date: Feb. 21, 2018, 4 pages.
Uniprot-H0F521, "FMN-Dependent Alpha-Hydroxy Acid Dehydrogenase Family Protein 1," Feb. 22, 2012, downloaded from web page: http://www.uniprot.org/uniprot/H0F521, Download date: Feb. 21, 2018, 4 pages.

(Continued)

*Primary Examiner* — Delia M Ramirez
(74) *Attorney, Agent, or Firm* — Panitch Schwarze Belisario & Nadel LLP

(57) ABSTRACT

Isolated oxidases, isolated polynucleotides encoding the oxidases, and methods of using the oxidases to produce α-oxocarboxylic acid compounds or L-α-amino acid compounds are described.

15 Claims, No Drawings
Specification includes a Sequence Listing.

(56) References Cited

OTHER PUBLICATIONS

Uniprot-J4Z5J9, "FMN-Dependent Alpha-Hydroxy Acid Dehydrogenase Family Protein 2," Oct. 31, 2012, downloaded from web page: http://www.uniprot.org/uniprot/J4Z5J9, Download date: Feb. 21, 2018, 4 pages.
Uniprot-E3HGV8, "FMN-Dependent Alpha-Hydroxy Acid Dehydrogenase Family Protein 2," Jan. 11, 2011, downloaded from web page: http://www.uniprot.org/uniprot/E3HGV8, Download date: Feb. 21, 2018, 4 pages.
Uniprot-H0FBE3, "FMN-Dependent Alpha-Hydroxy Acid Dehydrogenase Family Protein 2," Feb. 22, 2012, downloaded from web page: http://www.uniprot.org/uniprot/H0FBE3, Download date: Feb. 21, 2018, 4 pages.
Uniprot-A0A052I918, "(S)-mandelate Dehydrogenase," Jul. 9, 2014, downloaded from web page: http://www.uniprot.org/uniprot/A0A052I918.txt?version=1, Download date: Feb. 21, 2018, 1 page.
Belmouden et al., "The role of a β barrel loop 4 extension in modulating the physical and functional properties of long-chain 2-hydroxy-acid oxidase isozymes," Eur. J. Biochem., vol. 238, No. 3, pp. 790-798 (1996).
Extended European Search Report dated Dec. 19, 2017 in EP Application No. 15818623.9.
Strnad et al., "Achromobacter xylosoxidans A8 FMN-dependent dehydrogenase family protein 2" (2010).
Trimble et al., "Achromobacter piechaudii HLE FMN-dependent dehydrogenase family protein 1" (2012).
Li et al., "Achromobacter arsenitoxydans SY8 FMN-dependent dehydrogenase family protein 1" (2011).
Rusch et al., "The Sorcerer II Global Ocean Sampling expedition: northwest Atlantic through eastern tropical Pacific" (2007).
Li et al., "Achromobacter arsenitoxydans SY8 FMN-dependent dehydrogenase family protein 2" (2011).
Strnad et al., "Achromobacter xylosoxidans A8 FMN-dependent dehydrogenase family protein 1" (2010).
GenBank accession No. LN831029, Achromobacter xylosoxidans genome assembly NCTC10807 chromosome: 1 (2005).
Ferjancic-Biagini et al., "Inhibitory effects of anions and active site amino acid sequence of chicken liver L-2-hydroxyacid oxidase A, a member of the FMN-dependent α-hydroxyacid oxidizing enzyme family," Biochimie, vol. 80, No. 12, pp. 1047-1054 (1998).
Office Action dated Dec. 20, 2018 in JP Application No. 2016532901.

* cited by examiner

METHOD FOR PRODUCING L-α-AMINO ACID COMPOUND

CROSS-REFERENCE TO RELATED APPLICATION

This application is a Section 371 of International Application No. PCT/JP2015/069105, filed Jul. 2, 2015, which was published in the Japanese language on Jan. 14, 2016, under International Publication No. WO 2016/006521 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "600630-434US Sequence Listing" and a creation date of Jan. 10, 2017, and having a size of 50.7 kB. The sequence listing submitted via EFS-Web is part of the specification and is herein incorporated by reference in its entirety.

TECHNICAL FIELD

The present invention relates to an oxidase, a polynucleotide encoding the same, and a method for producing an α-amino acid compound, etc. using these.

BACKGROUND ART

Conventionally, methionine, one of the α-amino acid compounds, has been used as a feed additive for animals. To produce the compound, acrolein is reacted with methyl mercaptan to produce 3-(methylthio)propionaldehyde, and this is further reacted with prussic acid, ammonia, and carbon dioxide to produce 5-(2-methyl-mercaptoethyl)-hydantoin (methionine hydantoin). Finally, this is hydrolyzed with an alkali to produce alkali metal methionate, and then neutralized by using an acid, for example, sulfuric acid or carbonic acid, to release methionine (see, for example, Patent Document 1, etc.).

PRIOR ART DOCUMENT

Patent Document

Patent Document 1: JP 55-102557 A

DISCLOSURE OF THE INVENTION

Problems to be Solved by the Invention

The production method mentioned above uses prussic acid and acrolein as a C1- or C3-component, and the handling of these raw material compounds requires sufficient control and suitable facilities, etc. Therefore, development of a new method for producing an α-amino acid compound such as methionine is expected.

Means for Solving the Problems

The present invention provides the followings:
Item 1. A polynucleotide encoding any one of the following amino acid sequences (A1) to (A4):

(A1) an amino acid sequence represented by SEQ ID NO: 1, 3, or 5, (A2) an amino acid sequence i) having at least 45% sequence identity to an amino acid sequence represented by SEQ ID NO: 1, 3, or 5, and ii) having the ability to oxidize a 2-hydroxy-4-(methylthio)butyric acid derivative and convert the same into a corresponding 2-oxo-4-(methylthio)butyric acid derivative, (A3) an amino acid sequence i) encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or (A4) an amino acid sequence i) represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative (hereinafter sometimes referred to as the present invented polynucleotide (A));

Item 2. The polynucleotide according to the above item 1, which has a base sequence represented by SEQ ID NO: 2, 4, 6, 15, 16, or 17;

Item 3. A polynucleotide in which a promoter which can function in a host cell is connected with the polynucleotide according to the above item 1 or 2 so that they can function;

Item 4. A recombinant vector comprising the polynucleotide according to any one of the above items 1 to 3 (hereinafter sometimes referred to as the present invented recombinant vector);

Item 5. The recombinant vector according to the above item 4, which further comprises a polynucleotide encoding an amino acid sequence of a protein having the ability to aminate an α-oxocarboxylic acid compound and convert the same into a corresponding L-α-amino acid compound, or a polynucleotide in which the polynucleotide is connected with a promoter which can function in a host cell so that they can function;

Item 6. The recombinant vector according to the above item 5, wherein the amino acid sequence of the protein having the ability to aminate an α-oxocarboxylic acid compound and convert the same into a corresponding L-α-amino acid compound is any one of the following amino acid sequences (B1) to (B3):

(B1) an amino acid sequence represented by SEQ ID NO: 7, (B2) an amino acid sequence i, having at least 90% sequence identity to an amino acid sequence represented by SEQ ID NO: 7, and ii) of a protein having the ability to aminate a 2-oxo-4-(methylthio)butyric acid derivative and convert the same into a corresponding L-methionine derivative, or (B3) an amino acid sequence i) represented by SEQ ID NO: 7 in which one or plural amino acids are deleted, substituted, or added, and ii) of a protein having the ability to aminate a 2-oxo-4-(methylthio)butyric acid derivative and convert the same into a corresponding L-methionine derivative;

Item 7. A transformant in which the polynucleotide according to any one of the above item 1 to 3 or the recombinant vector according to the above item 4 is introduced into a host cell;

Item 8. The transformant according to the above item 7, wherein the host cell is a microorganism or *E. coli*;

Item 9. A transformant in which the recombinant vector according to the above item 5 or 6 is introduced into a host cell;

Item 10. The transformant according to the above item 9, wherein the host cell is a microorganism or *E. coli*;

Item 11. A transformant having the polynucleotide according to any one of the above items 1 to 3;

Item 12. A transformant having the followings:
i) a polynucleotide having a base sequence encoding an amino acid sequence of a protein having the ability to aminate an α-oxocarboxylic acid compound and convert the same into a corresponding L-α-amino acid compound, or a polynucleotide in which the polynucleotide is connected with a promoter which can function in a host cell so that they can function; and
ii) the polynucleotide according to any one of the above items 1 to 3;

Item 13. A method for producing a recombinant vector, which comprises the step of integrating the polynucleotide according to any one of the above items 1 to 3 into a vector which can be replicated in a host cell;

Item 14. A method for producing a transformant, which comprises the step of introducing the polynucleotide according to any one of the above items 1 to 3 or the recombinant vector according to any one of the above items 4 to 6 into a host cell;

Item 15. A protein having any one of the following amino acid sequences (A1) to (A4):
(A1) an amino acid sequence represented by SEQ ID NO: 1, 3, or 5,
(A2) an amino acid sequence i) having at least 45% sequence identity to an amino acid sequence represented by SEQ ID NO: 1, 3, or 5, and ii) of a protein having the ability to oxidize a 2-hydroxy-4-(methylthio)butyric acid derivative and convert the same into a corresponding 2-oxo-4-(methylthio)butyric acid derivative,
(A3) an amino acid sequence i) encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or
(A4) an amino acid sequence i) represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative (hereinafter sometimes referred to as the present invented protein (A));

Item 16. A method for producing an α-oxocarboxylic acid compound, which comprises the step of reacting a protein having any one of the following amino acid sequences (A1) to (A4):
(A1) an amino acid sequence represented by SEQ ID NO: 1, 3, or 5,
(A2) an amino acid sequence i) having at least 45% sequence identity to an amino acid sequence represented by SEQ ID NO: 1, 3, or 5, and ii) of a protein having the ability to oxidize a 2-hydroxy-4-(methylthio)butyric acid derivative and convert the same into a corresponding 2-oxo-4-(methylthio)butyric acid derivative,
(A3) an amino acid sequence i) encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or
(A4) an amino acid sequence i) represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative;
with an α-hydroxycarboxylic acid compound (hereinafter sometimes referred to as the present inventive production method 1);

Item 17. The production method according to the above item 16, wherein the α-hydroxycarboxylic acid compound is a sulfur-containing α-hydroxycarboxylic acid compound, and the corresponding α-oxocarboxylic acid compound is a sulfur-containing α-oxocarboxylic acid compound;

Item 18. The production method according to the above item 17, wherein the sulfur-containing α-hydroxycarboxylic acid compound is a compound represented by formula (1):

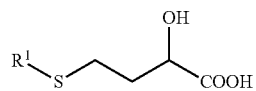

(1)

wherein $R^1$ represents a hydrogen atom or an optionally substituted a C1-8 alkyl group;
and the sulfur-containing α-oxocarboxylic acid compound is a compound represented by formula (2):

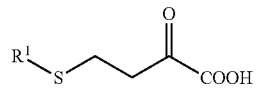

(2)

wherein $R^1$ is the same as defined above;

Item 19. The production method according to any one of the above items 16 to 18, wherein the protein having any one of the amino acid sequences (A1) to (A4) is provided in a reaction system in the form in which the protein is included in a transformant in which a polynucleotide encoding the protein is introduced into a host cell or in a treated product thereof;

Item 20. The production method according to the above item 19, wherein the transformant is the transformant according to any one of the above items 7, 8, and 11;

Item 21. The production method according to any one of the above items 16 to 20, wherein the step is performed in the presence of a protein having the ability to convert hydrogen peroxide into molecular oxygen;

Item 22. The production method according to the above item 21, wherein the protein having the ability to convert hydrogen peroxide into molecular oxygen is a catalase;

Item 23. The production method according to the above item 21 or 22, wherein the protein having the ability to convert hydrogen peroxide into molecular oxygen is provided in a reaction system in the form in which the protein is included in a transformant in which a polynucleotide encoding the protein is introduced into a host cell or in a treated product thereof;

Item 24. A method for producing an L-α-amino acid compound, which comprises (1) the step of reacting a protein having any one of the following amino acid sequences (A1) to (A4):
(A1) an amino acid sequence represented by SEQ ID NO: 1, 3, or 5,
(A2) an amino acid sequence i) having at least 45% sequence identity to an amino acid sequence represented by SEQ ID NO: 1, 3, or 5, and ii) of a protein having the ability to oxidize a 2-hydroxy-4-(methylthio)butyric acid derivative and convert the same into a corresponding 2-oxo-4-(methylthio)butyric acid derivative,
(A3) an amino acid sequence i, encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or
(A4) an amino acid sequence i) represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative;
with an α-hydroxycarboxylic acid compound to obtain a corresponding α-oxocarboxylic acid compound, and
(2) the step of reacting a protein having the ability to aminate an α-oxocarboxylic acid compound and convert the same into a corresponding L-α-amino acid compound with the α-oxocarboxylic acid compound obtained in the step (1) to obtain a corresponding L-α-amino acid compound (hereinafter sometimes referred to as the present inventive production method 2);

Item 25. The production method according to the above item 24, wherein the α-hydroxycarboxylic acid compound is a sulfur-containing α-hydroxycarboxylic acid compound, the corresponding α-oxocarboxylic acid compound is a sulfur-containing α-oxocarboxylic acid compound, and the corresponding L-α-amino acid compound is a sulfur-containing L-α-amino acid compound;

Item 26. The production method according to the above item 25, wherein the sulfur-containing α-hydroxycarboxylic acid compound is a compound represented by formula (1):

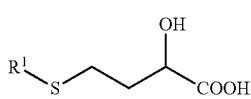

(1)

wherein $R^1$ represents a hydrogen atom or an optionally substituted a C1-8 alkyl group;
the sulfur-containing α-oxocarboxylic acid compound is a compound represented by formula (2):

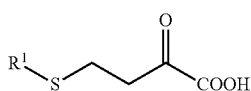

(2)

wherein $R^1$ is the same as defined above;

and the sulfur-containing L-α-amino acid compound is a compound represented by formula (3):

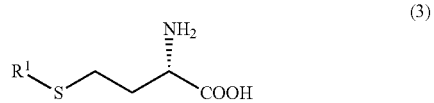

(3)

wherein $R^1$ is the same as defined above;

Item 27. The production method according to any one of the above items 24 to 26, wherein the protein having the ability to aminate an α-oxocarboxylic acid compound and convert the same into a corresponding L-α-amino acid compound is a leucine dehydrogenase;

Item 28. The production method according to the above item 27, wherein the leucine dehydrogenase is a leucine dehydrogenase derived from *Bacillus sphaericus*;

Item 29. The production method according to any one of the above items 24 to 27, wherein the amino acid sequence of a protein having the ability to aminate an α-oxocarboxylic acid compound and convert the same into a corresponding L-α-amino acid compound is any one of the following amino acid sequences (B1) to (B3):
(B1) an amino acid sequence represented by SEQ ID NO: 7,
(B2) an amino acid sequence i) having at least 90% sequence identity to an amino acid sequence represented by SEQ ID NO: 7, and ii) of a protein having the ability to aminate a 2-oxo-4-(methylthio)butyric acid derivative and convert the same to a corresponding L-methionine derivative, or
(B3) an amino acid sequence i) represented by SEQ ID NO: 7 in which one or plural amino acids are deleted, substituted, or added, and ii) of a protein having the ability to aminate a 2-oxo-4-(methylthio)butyric acid derivative and convert the same into a corresponding L-methionine derivative;

Item 30. The production method according to any one of the above items 24 to 29, wherein the protein having any one of the amino acid sequences (A1) to (A4) is provided in a reaction system in the form in which the protein is included in a transformant in which a polynucleotide encoding the protein is introduced into a host cell or in a treated product thereof;

Item 31. The production method according to the above item 30, wherein the transformant is the transformant according to any one of the above items 7 to 12;

Item 32. The production method according to any one of the above items 24 to 31, wherein the protein having the ability to aminate an α-oxocarboxylic acid compound and convert the same into a corresponding L-α-amino acid compound is provided in a reaction system in the form in which the protein is included in a transformant in which a polynucleotide encoding the protein is introduced into a host cell or in a treated product thereof;

Item 33. The production method according to the above item 32, wherein the transformant is the transformant according to any one of the above items 9, 10, and 12;

Item 34. The production method according to any one of the above items 24 to 33, wherein the step (1) is performed in the presence of a protein having the ability to convert hydrogen peroxide into molecular oxygen;

Item 35. The production method according to the above item 34, wherein the protein having the ability to convert hydrogen peroxide into molecular oxygen is a catalase;

Item 36. The production method according to the above item 34 or 35, wherein the protein having the ability to convert hydrogen peroxide into molecular oxygen is provided in a reaction system in the form in which the protein is included in a transformant in which a polynucleotide encoding the protein is introduced into a host cell or in a treated product thereof;

Item 37. The production method according to any one of the above items 24 to 36, wherein the step (2) is performed in the presence of a protein having the ability to convert an oxidized β-nicotinamide adenine dinucleotide or an oxidized β-nicotinamide adenine dinucleotide phosphate into its reduced form;

Item 38. The production method according to the above item 37, wherein the protein having the ability to convert an oxidized β-nicotinamide adenine dinucleotide or an oxidized β-nicotinamide adenine dinucleotide phosphate into its reduced form is a formate dehydrogenase;

Item 39. The production method according to the above item 37 or 38, wherein the protein having the ability to convert an oxidized β-nicotinamide adenine dinucleotide or an oxidized β-nicotinamide adenine dinucleotide phosphate into its reduced form is provided in a reaction system in the form in which the protein is included in a transformant in which a polynucleotide encoding the protein is introduced into a host cell or in a treated product thereof;

Item 40. The production method according to any one of the above items 24 to 39, wherein the step (1) and the step (2) are performed in one reaction system; and the like.

Effects of the Invention

According to the present invention, it is possible to provide an oxidase, a polynucleotide encoding the same, a method for producing an α-amino acid compound such as methionine using these, and the like.

MODE FOR CARRYING OUT THE INVENTION

To express a target polynucleotide in a host cell, for example, a polynucleotide in which a promoter which can function in a host cell is connected with the polynucleotide so that they can function is prepared, and introduced into a host cell.

As used herein, "connected so that they can function-"means that when a host cell is transformed by introducing a target polynucleotide into the host cell, the polynucleotide is bound to a promoter so that it is expressed under control of the promoter.

Examples of the promoter which can function in a microorganism include a lactose operon promoter of *E. coli*, a tryptophan operon promoter of *E. coli*, a T7 phage promoter, or a synthetic promoter which can function in *E. coli*, such as a tac promoter, a trc promoter, or a T7lac promoter.

A recombinant vector can be prepared by integrating a target polynucleotide, or a polynucleotide in which a promoter which can function in a host cell is connected with the polynucleotide so that they can function into a vector. Examples of the vector to be used can include a vector which contains genetic information replicable in a host cell, can proliferate autonomously, can be isolated and purified from a host cell, and encodes a detectable marker. Examples of a vector available when the host cell is *E. coli* include pUC119 (manufactured by Takara Bio), pTV118N (manufactured by Takara Bio), pBluescriptIII (manufactured by Toyobo), pCR2.1-TOPO (Invitrogen), pTrc99A (manufactured by GE Healthcare Japan), pKK22 3-3 (manufactured by GE Healthcare Japan), pET-22b (manufactured by Novagen), and pET-15b (manufactured by Novagen). When a vector containing a selection marker gene (e.g., an antibiotic resistance-imparting gene such as a kanamycin resistance gene and a neomycin resistance gene) is used as the vector, a transformant into which the vector is introduced can be selected using the phenotype, etc. of the selection marker gene as an index.

A transformant to be used in the present invention can be produced by introducing a target polynucleotide, a polynucleotide in which a promoter which can function in a host cell is connected with the polynucleotide so that they can function, or a recombinant vector containing these polynucleotides into a host cell.

Examples of the host cell include a microorganism belonging to the genus *Escherichia, Bacillus, Corynebacterium, Staphylococcus, Streptomyces, Saccharomyces, Kluyveromyces, Pichia, Rhodococcus,* or *Aspergillus*.

As a method for introducing a polynucleotide or a recombinant vector into a host cell, a usually used introduction method can be applied depending on a host cell to be used, and examples thereof include the calcium chloride method mentioned in "Molecular Cloning: A Laboratory Manual 2nd edition" (1989), Cold Spring Harbor Laboratory Press, "Current Protocols in Molecular Biology"(1987), John Wiley & Sons, Inc. ISBNO-471-50338-X, and the like, and electroporation mentioned in "Methods in Electroporation: Gene Pulser/*E. coli* Pulser System" Bio-Rad Laboratories, (1993), and the like.

A transformant into which a target polynucleotide or a recombinant vector, etc. is introduced can be selected by, for example, using the phenotype of a selection marker gene contained in a vector as mentioned above as an index.

The fact that the obtained transformant has the target polynucleotide can be confirmed by, for example, performing confirmation of a restriction enzyme site, analysis of a base sequence, Southern hybridization, Western hybridization, and the like, in accordance with a usual method mentioned in "Molecular Cloning: A Laboratory Manual 2nd edition" (1989), Cold Spring Harbor Laboratory Press, and the like.

As a medium for culture of the transformant to be used in the present invention, for example, various media appropriately containing a carbon source, a nitrogen source, an organic salt, an inorganic salt, and the like which are usually used for culture of host cells of microorganisms, etc. can be used.

Examples of the carbon source include saccharides such as glucose, dextrin, and sucrose; sugar alcohols such as glycerol; organic acids such as fumaric acid, citric acid, and pyruvic acid; animal oil; vegetable oil; and molasses. The amount of these carbon sources added to a medium is usually within a range of about 0.1 to 30% (w/v) based on the amount of a culture solution.

Examples of the nitrogen source include natural organic sources of nitrogen such as meat extract, peptone, yeast extract, malt extract, soy flour, corn steep liquor, cottonseed flour, dried yeast, and casamino acid; amino acids; sodium salts of inorganic acids such as sodium nitrate; ammonium salts of inorganic acids such as ammonium chloride, ammonium sulfate, and ammonium phosphate; ammonium salts of organic acids such as ammonium fumarate and ammonium citrate; and urea. Of these, ammonium salts of organic acids, natural organic sources of nitrogen, amino acids, and the like can also be often used as a carbon source. The amount of these nitrogen sources added to a medium is usually within a range of about 0.1 to 30% (w/v) based on the amount of a culture solution.

Examples of the organic salt and the inorganic salt can include chlorides, sulfates, acetates, carbonates, and phosphates of potassium, sodium, magnesium, iron, manganese, cobalt, zinc, and the like. Specific examples thereof include sodium chloride, potassium chloride, magnesium sulfate, ferrous sulfate, manganese sulfate, cobalt chloride, zinc sulfate, copper sulfate, sodium acetate, calcium carbonate, monopotassium hydrogenphosphate, and dipotassium hydrogenphosphate. The amount of these organic salts and/or inorganic salts added to a medium is usually within a range of about 0.0001 to 5% (w/v) based on the amount of a culture solution.

In the case of a transformant into which a polynucleotide is introduced in which a promoter induced by allolactose such as a tac promoter, a trc promoter, a T7lac promoter, and a lac promoter is connected with a polynucleotide encoding a target protein so that they can function, for example, a small amount of isopropyl thio-β-D-galactoside (IPTG) may be added to a medium as an inducer for inducing the production of the target protein. Also, in the case of culture of a transformant in which a polynucleotide in which a T7 phage promoter is connected with a polynucleotide encoding a target protein so that they can function is introduced into a lysogen of bacteriophage DE3 (λDE3 lysogen) in which a T7 RNA polymerase gene is integrated under control of an acJV5 promoter, a small amount of IPTG may be added to a medium as an inducer for inducing the production of the target protein.

Culture of the transformant can be performed in accordance with a method usually used for culture of host cells such as microorganisms, and examples thereof include liquid culture and solid culture such as test tube-shaking culture, reciprocal shaking culture, jar fermenter culture, and tank culture.

The culture temperature can be appropriately changed in a range so that the transformant can grow, and is usually about 15° C. to about 40° C. The pH of the medium is preferably within a range of about 6 to about 8. The culture time varies depending on the culture condition, and is usually preferably about one day to about 5 days.

As a method for purifying a target protein from a cultured product of a transformant producing the target protein having a polynucleotide encoding the target protein, for example, a transformant in which a polynucleotide encoding the target protein is introduced into a host cell, a usual method used for purification of proteins can be applied, and examples thereof can include the following methods:

Cells are collected by centrifugation, etc. from a cultured product of the transformant, and then the cells are disrupted by physical disruption such as sonication, Dyno-Mill treatment, or French press treatment or by chemical disruption using surfactants or lytic enzymes such as lysozyme, etc. From the disruption liquid thus obtained, impurities are removed by centrifugation, membrane filter filtration, and the like to prepare a cell-free extract. The extract is fractionated by appropriately using a separation and purification method such as cation exchange chromatography, anion exchange chromatography, hydrophobic interaction chromatography, gel filtration chromatography, metal chelate chromatography, and affinity chromatography, and thereby the target protein can be purified.

Examples of a carrier to be used in the chromatography include an insoluble macromolecular carrier such as cellulose, dextrin, or agarose into which a carboxymethyl (CM) group, a diethylaminoethyl (DEAE) group, a phenyl group, or a butyl group is introduced. A commercial carrier-filled column can be used, and examples of the commercial carrier-filled column include Q-Sepharose FF (trade name, manufactured by GE Healthcare Japan), Phenyl-Sepharose HP (trade name, manufactured by GE Healthcare Japan), and TSK-gel G3000SW (trade name, manufactured by Tosoh Corporation).

When the target protein is a protein in which consecutive several residues of histidine are added to its amino-terminal or carboxy-terminal domain, the protein can be purified by using a metal chelate affinity column. When the target protein is produced as a protein fused with a glutathione S-transferase, the protein can be purified by using a glutathione S-transferase monoclonal antibody column.

Examples of "treated product of transformant" as used herein include a freeze-dried transformant, an organic solvent-treated transformant, a dried transformant, a triturated transformant, an autolysate of a transformant, a sonicate of a transformant, a transformant extract, and an alkali-treated product of a transformant. Examples of the transformant extract include a cell-free extract, a partially purified protein or a purified protein prepared from a transformant, and an immobilized product thereof. Examples of a method for obtaining the immobilized product include the carrier binding method (a method for adsorbing a target protein, etc. to an inorganic carrier such as a silica gel and a ceramic, cellulose, or an ion exchange resin, etc.) and the entrapment method (a method for trapping a target protein, etc. in a macromolecular meshwork such as polyacrylamide, a sulfur-containing polysaccharide gel (e.g., a carrageenan gel), an alginic acid gel, or an agar gel, etc.).

Taking account of industrial production using a transformant, rather than use of a living transformant, use of a treated product obtained by killing the transformant is preferable in terms of less limitation on a production facility. Examples of a method for killing a transformant include physical sterilization (heating, drying, freezing, light, sonication, filtration, electrification) and chemical sterilization (alkali, acid, halogen, an oxidizing agent, sulfur, boron, arsenic, metal, alcohol, phenol, amine, sulfide, ether, aldehyde, ketone, cyanogen, and an antibiotic). Generally, of these sterilization methods, it is desirable to select a treatment method which does not inactivate the enzyme activity of the target protein as possible and has less effects on the reaction system such as residue and contamination.

The present invented polynucleotide (A) encodes any one of the following amino acid sequences (A1) to (A4):

(A1) an amino acid sequence represented by SEQ ID NO: 1, 3, or 5, (A2) an amino acid sequence i) having at least 45% sequence identity to an amino acid sequence represented by SEQ ID NO: 1, 3, or 5, and ii) of a protein having the ability to oxidize a 2-hydroxy-4-(methylthio)butyric acid derivative and convert the same into a corresponding 2-oxo-4-(methylthio)butyric acid derivative, (A3) an amino acid sequence i) encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or (A4) an amino acid sequence i % represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative.

The present invented protein (A) has any one of the following amino acid sequences (A1) to (A4):

(A1) an amino acid sequence represented by SEQ ID NO: 1, 3, or 5, (A2) an amino acid sequence i) having at least 45% sequence identity to an amino acid sequence represented by SEQ ID NO: 1, 3, or 5, and ii) of a protein having the ability to oxidize a 2-hydroxy-4-(methylthio)butyric acid derivative and convert the same into a corresponding 2-oxo-4-(methylthio)butyric acid derivative, (A3) an amino acid sequence i) encoded by a polynucleotide hybridized under a stringent condition to a polynucleotide composed of a sequence complementary to a base sequence represented by SEQ ID NO: 2, 4, or 6, and ii) of a protein having the ability to oxidize a 2-hydroxy-4-(methylthio)butyric acid derivative and convert the same into a corresponding 2-oxo-4-(methylthio)butyric acid derivative, or (A4) an amino acid sequence i) represented by SEQ ID NO: 1, 3, or 5 in which one or plural amino acids are deleted, substituted, or added, and ii) of a protein having the ability to oxidize a 2-hydroxy-4-(methylthio)butyric acid derivative and convert the same into a corresponding 2-oxo-4-(methylthio)butyric acid derivative.

A difference which is sometimes observed between an amino acid sequence encoded by the present invented polynucleotide (A) or an amino acid sequence of the present invented protein (A) and an amino acid sequence represented by SEQ ID NO: 1, 3, or 5 is deletion, substitution, or addition, etc. of some amino acids (hereinafter sometimes generally referred to as alteration of an amino acid). The "addition" includes not only addition of an amino acid to the end of a sequence but also insertion of an amino acid into a sequence. Examples of the alteration of an amino acid can include (a) deletion by intracellular processing of a protein having an amino acid sequence represented by SEQ ID NO: 1, 3, or 5, (b) deletion, substitution, or addition of an amino acid as a result of a naturally occurring gene mutation due to the species difference or individual difference of an organism from which the protein is derived, or (c) deletion, substitution, or addition of an amino acid occurring due to a mutation of an artificially introduced gene, etc.

The number of amino acids to be altered is not limited as long as the number is within a range so that a protein having the above altered amino acid sequence can exert the ability to oxidize a 2-hydroxy-4-(methylthio)butyric acid derivative and convert the same into a corresponding 2-oxo-4-(methylthio)butyric acid derivative. Examples of "plural amino acids" in the amino acid sequence (A4) encoded by the present invented polynucleotide (A) or the amino acid sequence (A4) of the present invented protein (A) include 2, 3, 4, 5, 6, 7, 10, 15, 20, 25, 30, 35, or 40 amino acids.

Examples of the substitution of an amino acid include conservative substitution to an amino acid having similar hydrophobicity, electric charge, pK, conformational characteristics, or the like. Specific examples of such substitution include substitution of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine; and the like in the group.

Examples of the addition of an amino acid can include addition of about 20 residues of amino acid including about consecutive 6 residues of histidine to the amino terminus or carboxy terminus of an amino acid sequence.

Examples of a method for artificially altering an amino acid include a method in which a site-specific mutation is introduced into a polynucleotide encoding an amino acid sequence represented by SEQ ID NO: 1, 3, or 5 and then this polynucleotide is expressed by a conventional method. Examples of a method for introducing a site-specific mutation can include the methods by Olfert Landt et al. (Gene 96 125-128 1990), Smith et al. (Genetic Engineering 3 1 Setlow, J. and Hollaender, A Plenum: New York), Vlasuk et al. (Experimental Manipulation of Gene Expression, Inouye, M.: Academic Press, New York), Hos. N. Hunt et al. (Gene 77 51 1989), and the like, and a method for using commercial kits such as Mutan-Express Km (manufactured by Takara Bio), TaKaRa La PCR in vitro Mutagenesis Kit (manufactured by Takara Bio), and QuickChange II Site-Directed Mutagenesis Kit (manufactured by STRATAGENE).

Examples of the method for artificially altering an amino acid also include a method in which a mutation is randomly introduced into a polynucleotide encoding an amino acid sequence represented by SEQ ID NO: 1, 3, or 5 and then this polynucleotide is expressed by a conventional method. Examples of a method for randomly introducing a mutation include a method in which PCR is performed using a polynucleotide encoding any one of the above amino acid sequences as a template and using a primer pair which can amplify the full length of each polynucleotide, under a reaction condition in which the concentration of each of dATP, dTTP, dGTP, and dCTP added which is used as a substrate is changed from the normal concentration, or a reaction condition in which the concentration of $Mg^{2+}$, which accelerates the polymerase reaction, is increased compared with the normal concentration. Examples of such PCR method include the method mentioned in Method in Molecular Biology, (31), 1.994, 97-112.

"Sequence identity" means the identity between two amino acid sequences or base sequences. The "sequence identity" is determined by comparing two sequences aligned to an optimal state over all regions of sequences to be compared. In optimal alignment of amino acid sequences or base sequences to be compared, addition or deletion (e.g., gap, etc.) may be allowed. Such sequence identity can be calculated by using, for example, sequence analysis tools such as the BESTFIT program (Devereux et al. (1984) Nucleic Acids Research 12, p 387-395) provided by UWGCG Package, PILEUP, and the BLAST algorithm (Altschul S. F. (1993) J Mol Evol 36:290-300; Altschul S. F. (1990) J Mol Biol 215:403-10). Sequence identity can also be calculated by using commercial sequence analysis software.

Examples of "at least 45% sequence identity" in the amino acid sequence (A2) encoded by the present invented polynucleotide (A) or the amino acid sequence (A2) of the present invented protein (A) include at least 45, 50, 55, 60, 65, 70, 75, 80, 85, 90, 95, 98, or 99% sequence identity.

In an amino acid sequence encoded by the present invented polynucleotide (A) or an amino acid sequence of the present invented protein (A), "polynucleotide hybridized under a stringent condition to a polynucleotide composed of a sequence complementary to a base sequence represented by SEQ ID NO: 2, 4, or 6" means a polynucleotide (1) which form a hybrid by base pairing with a polynucleotide composed of a sequence complementary to a base sequence represented by SEQ ID NO: 2, 4, or 6 by being hybridized at 65° C. under a high ionic concentration [for example, 6×SSC (900 mM sodium chloride and 90 mM sodium citrate)] and (2) in which the hybrid is maintained even after being incubated at 65° C. for 30 minutes under a low ionic concentration [for example, 0.1×SSC (15 mM sodium chloride and 1.5 mM sodium citrate)] in the Southern hybridization mentioned in, for example, "Cloning and Sequence" (supervised by Itaru Watanabe, edited by Masahiro Sugiura, 1989, published by Nosonbunka-sha), etc.

Specific examples of the above polynucleotide include a polynucleotide having a base sequence represented by SEQ ID NO: 2, 4, 6, 15, 16, or 17, a polynucleotide having a base sequence represented by SEQ ID NO: 2, 4, 6, 15, 16, or 17 in which some bases are deleted, substituted, or added, or a polynucleotide having a base sequence having at least 90%, 95%, 98%, or 99% sequence identity to a base sequence represented by SEQ ID NO: 2, 4, 6, 15, 16, or 17.

The present invented polynucleotide (A) may be a polynucleotide cloned from DNAs existing in the natural world, a polynucleotide into which deletion, substitution, or addition of some bases in a base sequence of this cloned polynucleotide is artificially introduced, or a chemically synthesized polynucleotide.

The present invented polynucleotide (A) can be obtained from, for example, a microorganism having the ability to oxidize α-hydroxycarboxylic acid to corresponding α-oxocarboxylic acid, and specifically, a microorganism belonging to the genus *Achromobacter* such as an *Achromobacter denitrificans* ATCC55564 strain. These microorganisms may be separated naturally, or may be obtained through purchase from culture collection institutes.

Examples of the culture collection institutes from which such microorganisms can be obtained can include the following culture collection institutes.

1. Institute for Fermentation, Osaka (IFO) Collection

At present, it is transferred to the NITE Biological Resource Center (NBRC). For obtaining microorganisms, it is only necessary to apply purchase to the NBRC. For purchase application, for example, it is only necessary to access the website of the NBRC.

2. American Type Culture Collection (ATCC)

Microorganisms can be obtained through the ATCC Business Group of Summit Pharmaceuticals International Corporation. For purchasing microorganisms, for example, it is only necessary to access the website of the Group. Microorganisms may be purchased directly from the ATCC.

3. Japan Collection of Microorganisms (JCM)

At present, it is transferred to the Japan Collection of Microorganisms of RIKEN BioResource Center (RIKEN BRC). For obtaining microorganisms, it is only necessary to apply purchase to the institute, and, for example, to access websites related to culture collection on the website of the institute.

4. IAM Culture Collection

At present, among the IAM Culture Collection preserved strains, bacteria, yeasts, filamentous fungi are transferred to the RIKEN BRC-JCM, and microalgae are transferred to the Microbial Culture Collection at the National Institute for Environmental Studies (NIES). For obtaining microorganisms, it is only necessary to apply purchase to these institutes, and, for example, to access websites related to culture collection on the websites of these institutes.

The present invented polynucleotide (A) can be prepared by, for example, the following procedures.

A DNA library is prepared from a microorganism belonging to the genus *Achromobacter* such as *Achromobacter denitrificans*, etc. in accordance with a usual genetic engineering method (e.g., the method mentioned in "New Cell Engineering Experimental Protocol" (edited by Department of Oncology, Institute of Medical Science, the University of Tokyo, Shujunsha Co., Ltd., 1993)). Then, by performing PCR using the DNA library thus prepared as a template and using an appropriate primer, a polynucleotide encoding an amino acid sequence represented by SEQ ID NO: 1, 3, or 5, a polynucleotide encoding an amino acid sequence represented by SEQ ID NO: 1, 3, or 5 in which one or plural amino acids are deleted, substituted, or added, or a polynucleotide having a base sequence represented by SEQ ID NO: 2, 4, or 6, etc. is amplified, and thereby the present invented polynucleotide (A) can be prepared.

A restriction enzyme recognition sequence, etc. may be added to the 5' end side, the 3' end side, or both of a primer used for the above PCR.

For example, by performing PCR using the above DNA library as a template and using an oligonucleotide having a base sequence represented by SEQ ID NO: 9 and an oligonucleotide having a base sequence represented by SEQ ID NO: 10 as a primer, a polynucleotide composed of a base sequence represented by SEQ ID NO: 2 is amplified, and thereby the present invented polynucleotide (A) can be prepared.

By performing PCR using the above DNA library as a template and using an oligonucleotide having a base sequence represented by SEQ ID NO: 11 and an oligonucleotide having a base sequence represented by SEQ ID NO: 12 as a primer, a polynucleotide composed of a base sequence represented by SEQ ID NO: 4 can be amplified.

By performing PCR using the above DNA library as a template and using an oligonucleotide having a base sequence represented by SEQ ID NO: 13 and an oligonucleotide having a base sequence represented by SEQ ID NO: 14 as a primer, a polynucleotide composed of a base sequence represented by SEQ ID NO: 6 can be amplified.

Examples of a condition for the above PCR include a condition in which a reaction solution prepared by mixing 20 μM each of 4 dNTPs, 15 pmol each of 2 oligonucleotide primers, 1.3 U of a Taq polymerase, and a DNA library as a template is incubated at 94° C. for 2 minutes, and then an incubation cycle consisting of incubation at 94° C. for 10 seconds, followed by 65° C. for 30 seconds, followed by 72° C. for 90 seconds is performed 10 times, subsequently an incubation cycle consisting of incubation of 94° C. for 10 seconds, followed by 65° C. for 30 seconds, followed by 72° C. for one minute and 5 seconds is performed 20 times, and further the solution is maintained at 72° C. for 7 minutes.

Also by performing PCR using the above DNA library as a template and using an oligonucleotide having a partial base sequence selected from a base sequence encoding an amino acid sequence represented by SEQ ID NO: 1, 3, or 5 (e.g., an oligonucleotide composed of a base sequence of at least about 14 bases at the 5' end of a base sequence encoding an amino acid sequence represented by SEQ ID NO: 1, 3, or 5) and an oligonucleotide of at least about 14 bases composed of a base sequence complementary to a base sequence near the DNA insertion site of the vector used for the DNA library construction as a primer, a polynucleotide having a base sequence encoding an amino acid sequence represented by SEQ ID NO: 1, 3, or 5, or a polynucleotide having a base sequence encoding an amino acid sequence represented by SEQ ID NO: 1, 3, or 5 in which one or plural amino acids are deleted, substituted, or added, etc. is amplified, and thereby the present invented polynucleotide (A) can be prepared.

The present invented polynucleotide (A) can also obtained by, for example, hybridizing, as a probe, DNA composed of a base sequence of at least about 15 bases having a partial base sequence selected from a base sequence encoding an amino acid sequence represented by SEQ ID NO: 1, 3, or 5 to a DNA library into which a vector derived from a microorganism or a phage is inserted under the condition mentioned below to detect DNA to which the probe specifically binds.

Examples of a method for hybridizing a probe to chromosomal DNA or a DNA library include colony hybridization and plaque hybridization, and a method can be selected according to the type of the vector used for preparation of the library.

When a library to be used has been prepared by using a plasmid vector, it is better to use colony hybridization. Specifically, the DNA of the library is introduced into a host microorganism to obtain a transformant, and the transformant thus obtained is diluted, and then the dilution is seeded on an agar medium and cultured until a colony appears.

When a library to be used has been prepared by using a phage vector, it is better to use plaque hybridization. Specifically, a host microorganism and a phage of the library are mixed under an infectible condition, and further mixed with a soft agar medium, and then the mixture is seeded on an agar medium and cultured until a plaque appears.

In any hybridization above, a membrane is placed on the above cultured agar medium, a transformant or a phage is adsorbed/transcribed on the membrane. After this membrane is treated with an alkali, it is neutralized, and then DNA is immobilized on the membrane. More specifically, for example, in the case of plaque hybridization, a nitrocellulose membrane or a nylon membrane (e.g., Hybond-N+ (GE Healthcare Japan, trade mark)) is placed on the agar medium, and allowed to stand for about one minute to adsorb/transcribe a phage particle to the membrane. Next, phage DNA is eluted on the membrane by immersing the membrane in an alkali solution (e.g., 1.5 M sodium chloride and 0.5 M sodium hydroxide) for about 3 minutes to dissolve the phage particle, and the membrane is immersed in a neutralizing solution (e.g., 1.5 M sodium chloride and 0.5 M Tris-hydrochloric acid buffer pH 7.5) for about 5 minutes. Subsequently, the membrane is washed with a rinsing fluid (e.g., 0.3 M sodium chloride, 30 mM citric acid, and 0.2 M Tris-hydrochloric acid buffer pH 7.5) for about 5 minutes, and then, for example, the membrane is heated at about 80° C. for about 90 minutes to immobilize the phage DNA on the membrane.

Using the membrane prepared in this way, hybridization is performed using the above DNA as a probe. Hybridization can be performed in accordance with, for example, the description such as J. Sam brook, E. F. Frisch, T. Maniatis "Molecular Cloning: A Laboratory Manual 2nd edition (1989)" Cold Spring Harbor Laboratory Press.

DNA to be used as a probe may be labeled by a radioisotope or labeled by a fluorochrome.

Examples of a method for labeling DNA to be used as a probe by a radioisotope include a method in which PCR is performed using DNA to be used as a probe as a template by substituting dCTP in a PCR reaction solution by ($\alpha$-$^{32}$P) dCTP by using the Random Primer DNA Labeling Kit (manufactured by Takara Bio), etc.

When DNA used as a probe is labeled by a fluorochrome, for example, the ECL Direct Nucleic Acid Labeling and Detection System (manufactured by GE Healthcare Japan), etc. can be used.

Hybridization can be performed, for example, as follows. A prehybridization solution containing 450 to 900 mM sodium chloride and 45 to 90 mM sodium citrate, containing sodium dodecyl sulfate (SDS) at a concentration of 0.1 to 1.0% by weight, containing denatured non-specific DNA at a concentration of 0 to 200 µl/ml, and optionally containing albumin, Ficoll, polyvinylpyrrolidone, and the like at a concentration of 0 to 0.2% by weight each (preferably, a prehybridization solution containing 900 mM sodium chloride, 90 mM sodium citrate, 1.0% by weight of SDS, and 100 µl/ml of denatured calf-thymus DNA) is prepared in the proportion within a range of 50 to 200 µl based on 1 cm$^2$ of the membrane prepared as mentioned above, and the membrane is immersed in the prehybridization solution and incubated at 42 to 65° C. for 1 to 4 hours.

Next, a solution prepared by mixing, for example, a hybridization solution containing 450 to 900 mM sodium chloride and 45 to 90 mM sodium citrate, containing SDS at a concentration of 0.1 to 1.0% by weight, containing denatured non-specific DNA at a concentration of 0 to 200 µg/ml, and optionally containing albumin, Ficoll, polyvinylpyrrolidone, and the like at a concentration of 0 to 0.2% by weight each (preferably, a hybridization solution containing 900 mM sodium chloride, 90 mM sodium citrate, 1.0% by weight of SDS, and 100 µg/ml of denatured calf-thymus DNA) with a probe obtained by preparation using the method mentioned above (the amount corresponds to 1.0× 10$^4$ to 2×10$^6$ cpm based on 1 cm$^2$ of the membrane) is prepared in the proportion within a range of 50 to 200 µl based on 1 cm$^2$ of the membrane, and the membrane is immersed in the hybridization solution and incubated at 42 to 65° C. for 12 to 20 hours.

After the hybridization, the membrane is removed, and washed with a rinsing fluid at 42 to 65° C. containing 15 to 300 mM sodium chloride, 1.5 to 30 mM sodium citrate, 0.1 to 1.0% by weight of SDS, and the like (preferably, a rinsing fluid at 65° C. containing 15 mM sodium chloride, 1.5 mM sodium citrate, and 1.0% by weight of SDS), etc. The washed membrane is gently washed with 2×SSC (300 mM sodium chloride and 30 mM sodium citrate), and then dried. By subjecting this membrane to, for example, autoradiography, etc. to detect the position of the probe on the membrane, a clone at the position on the membrane of DNA to be hybridized to the probe used is identified on the original agar medium, and fishing of this is performed to isolate a clone having the DNA.

From a cultured cell obtained by culture of the clone thus obtained, the present invented polynucleotide (A) can be prepared.

The present invented polynucleotide (A) can also be prepared by performing chemical synthesis of a nucleic acid having a target base sequence in accordance with a usual method such as, for example, the phosphite-triester method (Hunkapiller, M. et al., Nature, 310, 105, 1984), based on its base sequence.

The present invented polynucleotide (A) can also be prepared by selecting, as a codon encoding any one of the above amino acid sequences (A1) to (A4), a codon so that the frequency of use of codon corresponds to that in *E. coli* to design a base sequence, and by chemically synthesizing a polynucleotide composed of the base sequence thus designed.

Specifically, for example, a codon corresponding to each amino acid contained in an amino acid sequence represented by SEQ ID NO: 1, 3, or 5 is selected so that the frequency of use of codon is close to that in a microbial cell to be expressed (e.g., *E. coli*) to design a base sequence encoding a target amino acid sequence. Information on the frequency of use of codon in *E. coli*, etc. can be obtained by, for example, using the DNA database well known for a person skilled in the art (GenBank, EMBL, DDBJ, and the like).

Specific examples will be described below.

The number of respective amino acids contained in a target amino acid sequence is calculated. Codons to be used are assigned to the amino acids with the number calculated above so that the frequency is closest to the mean appearance frequency of codon in a microbial cell in which a polynucleotide is expressed. The use order of each codon is assigned so that the same codon is not consecutive as possible. From an amino acid at the N-terminal side in order, a codon is selected for each amino acid in the determined order, and is tentatively determined as a codon of its amino acid residue. By repeating these procedures, codons of all amino acids up to the C terminus are tentatively determined, and finally a termination codon is placed. With respect to a base sequence composed of the tentatively determined codons, the fact that a base sequence inhibiting the transcription of genes in a microbial cell and a base sequence recognized by restriction enzymes to be used in the subsequent operations do not exist is confirmed. If such base sequence exists, the codon involved in this base sequence is replaced by a codon used in other parts. In such base sequence design, it is preferable to add a base sequence recognized by appropriate restriction enzymes to the 5' end side and the 3' end side for the subsequent operations.

Synthesis of a polynucleotide having a base sequence designed in this way can be performed by the long-chain DNA synthesis method using PCR (Cell Engineering Supplement, Plant Cell Engineering Series 7 "PCR Experimental Protocol for Plants", p 95-100, supervised by Takumi Shimamoto and Takuji Sasaki, Shujunsha Co., Ltd., published on Jul. 1, 1997) (hereinafter this method is sometimes referred to as the assembly PCR method). In the method, DNA is synthesized using only a long synthetic oligonucleotide primer. A primer pair is synthesized so that the 3' end of each primer has a complementary strand or an overlap of about 10 bp to about 12 bp, and DNA synthesis is performed using mutual primers as a template. Examples of the full length of the primer can include about 60 mer to about 100 mer. Preferably, examples thereof include about 80 mer to about 100 mer.

By binding these oligonucleotide primers in order by PCR reaction, DNA having a target base sequence is obtained. The DNA thus obtained is introduced into a cloning vector and cloned in accordance with a conventional method. The base sequence of the clone thus obtained is confirmed with a DNA sequencer, and the fact that a polynucleotide having the target base sequence was obtained is confirmed. In this way, the present invented polynucleotide (A) can be obtained by, for example, artificially synthesizing a polynucleotide having a base sequence represented by SEQ ID NO: 15, 16, or 17 of the present invention.

The polynucleotide prepared as mentioned above can be cloned into a vector in accordance with the method mentioned in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like.

The base sequence of the polynucleotide prepared as mentioned above can be analyzed by the dideoxy terminator method, etc. mentioned in F. Sanger, S. Nicklen, A. R. Coulson, Proceeding of Natural Academy of Science U.S.A. (1977) 74: 5463-5467, etc. For sample preparation for base sequence analysis, for example, a commercial reagent such as ABI PRISM Dye Terminator Cycle Sequencing Ready Reaction Kit by PerkinElmer Inc. may be used.

The fact that the polynucleotide prepared as mentioned above encodes an amino acid sequence of a protein having the ability to oxidize α-hydroxycarboxylic acid (e.g., 2-hydroxy-4-(methylthio)butyric acid) and convert the same into corresponding α-oxocarboxylic acid (e.g., 2-oxo-4-(methylthio)butyric acid) can be confirmed by, for example, the following procedures.

The polynucleotide obtained as mentioned above is inserted into a vector so that the polynucleotide is connected downstream of a promoter which can function in a host cell, and the recombinant vector thus obtained is introduced into a host cell to obtain a transformant. A cultured product of the transformant thus obtained is reacted with α-hydroxycarboxylic acid (e.g., sulfur-containing α-hydroxycarboxylic acid, more specifically, 2-hydroxy-4-(methylthio)butyric acid). By analyzing the amount of corresponding α-oxocarboxylic acid in the reaction product (e.g., sulfur-containing α-oxocarboxylic acid, more specifically, 2-oxo-4-(methylthio)butyric acid), the fact that the polynucleotide thus obtained encodes an amino acid sequence of a protein having target ability can be confirmed.

To express the present invented polynucleotide (A) in a host cell, for example, a polynucleotide in which a promoter which can function in a host cell is connected with the present invented polynucleotide (A) so that they can function is prepared, and introduced into a host cell.

Examples of the promoter which can function in a microorganism include a synthetic promoter which can function in *E. coli* as mentioned above. A promoter which controls the expression of the present invented polynucleotide (A) in *Achromobacter denitrificans* may be used.

The present invented recombinant vector can be prepared by integrating the present invented polynucleotide (A), or a polynucleotide in which a promoter which can function in a host cell is connected with the present invented polynucleotide (A) so that they can function into a vector.

The present invented recombinant vector can also include the present invented polynucleotide (A), or a polynucleotide in which a promoter which can function in a host cell is connected with the present invented polynucleotide (A) so that they can function, as well as a polynucleotide encoding an amino acid sequence of a protein having the ability to aminate an α-oxocarboxylic acid compound and convert the same into a corresponding L-α-amino acid compound (hereinafter sometimes referred to as the present invented protein (B)), or a polynucleotide in which the polynucleotide is connected with a promoter which can function in a host cell so that they can function.

Examples of the protein having the ability to aminate an α-oxocarboxylic acid compound and convert the same into a corresponding L-α-amino acid compound include an amino acid dehydrogenase and an aminotransferase. Specific examples of the amino acid dehydrogenase can include an alanine dehydrogenase, a glutamic acid dehydrogenase, a leucine dehydrogenase, and a phenylalanine dehydrogenase, and preferably a leucine dehydrogenase.

More specific examples of the above protein having the ability to aminate an α-oxocarboxylic acid compound and convert the same into a corresponding L-α-amino acid compound can include a leucine dehydrogenase derived from a *Bacillus sphaericus* IFO3525 strain mentioned in Journal of Molecular Catalysis B: Enzymatic 23 (2003) 239-247, and a protein having an amino acid sequence of the leucine dehydrogenase in which the 113th alanine is converted to glycine.

An amino acid sequence represented by SEQ ID NO: 39 is an amino acid sequence of a leucine dehydrogenase derived from a *Bacillus sphaericus* IFO3525 strain mentioned in Journal of Molecular Catalysis B: Enzymatic 23 (2003) 239-247.

An amino acid sequence represented by SEQ ID NO: 7 is an amino acid sequence represented by SEQ ID NO: 39 in which the 113th alanine is converted to glycine.

Specific examples of the amino acid sequence of a protein having the ability to aminate an α-oxocarboxylic acid compound and convert the same into a corresponding L-α-amino acid compound can also include any one of the following amino acid sequences (B1) to (B3): (B1) an amino acid sequence represented by SEQ ID NO: 7, (B2) an amino acid sequence i) represented by SEQ ID NO: 7 and having at least 90% sequence identity, and ii) of a protein having the ability to aminate a 2-oxo-4-(methylthio)butyric acid derivative and convert the same into a corresponding L-methionine derivative, or (B3) an amino acid sequence i, represented by SEQ ID NO: 7 in which one or plural amino acids are deleted, substituted, or added, and ii) of a protein having the ability to aminate a 2-oxo-4-(methylthio)butyric acid derivative and convert the same into a corresponding L-methionine derivative.

A difference which is sometimes observed between the amino acid sequence of the present invented protein (B) and an amino acid sequence represented by SEQ ID NO: 7 is deletion, substitution, or addition, etc. of some amino acids. The "addition" includes not only addition of an amino acid to the end of a sequence but also insertion of an amino acid into a sequence. Examples of the alteration of an amino acid can include (a) deletion by intracellular processing of a protein having an amino acid sequence represented by SEQ ID NO: 7, (b) deletion, substitution, or addition of an amino acid as a result of a naturally occurring gene mutation due to the species difference or individual difference of an organism from which the protein is derived, or (c) deletion, substitution, or addition of an amino acid occurring due to a mutation of an artificially introduced gene, etc.

The number of amino acids to be altered is not limited as long as the number is within a range so that a protein having the above altered amino acid sequence can exert the ability to aminate a 2-oxo-4-(methylthio)butyric acid derivative and convert the same into a corresponding L-methionine derivative. Examples of "plural amino acids" in the above amino acid sequence (B3) of the present invented protein (B) include 2, 3, 4, 5, 6, 7, 10, 15, 18, 20, 25, 30, 35, 36, or 40 amino acids.

Examples of the substitution of an amino acid include conservative substitution to an amino acid having similar hydrophobicity, electric charge, pK, conformational characteristics, or the like. Specific examples of such substitution include substitution of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine; and the like in the group.

Examples of the addition of an amino acid can include addition of about 20 residues of amino acid including about consecutive 6 residues of histidine to the amino terminus or carboxy terminus of an amino acid sequence.

Examples of a method for artificially altering an amino acid include a method in which a site-specific mutation is introduced into a polynucleotide encoding an amino acid sequence represented by SEQ ID NO: 7 and then this polynucleotide is expressed by a conventional method.

Examples of the method for artificially altering an amino acid also include a method in which a mutation is randomly introduced into a polynucleotide encoding an amino acid sequence represented by SEQ ID NO: 7 and then this polynucleotide is expressed by a conventional method.

Examples of "at least 90% sequence identity" in the above amino acid sequence (B2) of the present invented protein (B) include at least 90, 95, 983, or 99% sequence identity.

A polynucleotide encoding an amino acid sequence of a protein having the ability to aminate an α-oxocarboxylic acid compound and convert the same into a corresponding L-α-amino acid compound (hereinafter sometimes referred to as the present polynucleotide (B)) can be obtained from, for example, a microorganism having the ability to aminate an α-oxocarboxylic acid compound and convert the same into a corresponding L-α-amino acid compound, for example, a microorganism belonging to the genus Bacillus such as a Bacillus sphaericus IFO03525 strain.

A DNA library is prepared from a microorganism belonging to the genus Bacillus such as a Bacillus sphaericus IFO3525 strain, etc. in accordance with a usual genetic engineering method. Then, by performing PCR using the DNA library thus prepared as a template and using an appropriate primer, a polynucleotide encoding an amino acid sequence represented by SEQ ID NO: 39, or a polynucleotide encoding an amino acid sequence represented by SEQ ID NO: 39 in which one or plural amino acids are deleted, substituted, or added, etc. is amplified, and thereby the present polynucleotide (B) can be prepared.

For example, as a primer for amplification of a polynucleotide having a base sequence represented by SEQ ID NO: 40 encoding an amino acid sequence represented by SEQ ID NO: 39, an oligonucleotide having a base sequence represented by SEQ ID NO: 18 and an oligonucleotide having a base sequence represented by SEQ ID NO: 19 are synthesized. As a primer for mutation introduction for converting the 113th alanine in an amino acid sequence represented by SEQ ID NO: 39 to glycine, an oligonucleotide having a base sequence represented by SEQ ID NO: 20 and an oligonucleotide having a base sequence represented by SEQ ID NO: 21 are synthesized.

By performing PCR using the above DNA library as a template and using an oligonucleotide having a base sequence represented by SEQ ID NO: 18 and an oligonucleotide having a base sequence represented by SEQ ID NO: 19 as a primer, a polynucleotide having a base sequence represented by SEQ ID NO: 40 is amplified. The polynucleotide thus amplified is integrated into a vector to obtain a recombinant vector containing a polynucleotide having a base sequence represented by SEQ ID NO: 40. PCR is performed using the recombinant vector thus obtained as a template and using an oligonucleotide having a base sequence represented by SEQ ID NO: 20 and an oligonucleotide having a base sequence represented by SEQ ID NO: 21 as a primer, and the PCR product thus obtained is processed with Dpn I, and then introduced into E. coli. The base sequence of the recombinant vector of the transformant thus obtained is analyzed to obtain a polynucleotide encoding an amino acid sequence into which the target amino acid mutation is introduced, namely an amino acid sequence represented by SEQ ID NO: 39 in which the 113th alanine is substituted by glycine (an amino acid sequence represented by SEQ ID NO: 7). Examples of a base sequence encoding an amino acid sequence represented by SEQ ID NO: 7 include a base sequence represented by SEQ ID NO: 8.

The present polynucleotide (B) can also be prepared by performing chemical synthesis of a nucleic acid having a target base sequence in accordance with a usual method such as, for example, the phosphite-triester method (Hunkapiller, M. et al., Nature, 310, 105, 1984), based on its base sequence.

The present polynucleotide (B) can also be prepared by selecting, as a codon encoding any one of the above amino acid sequences (B1) to (B3), a codon so that the frequency of use of codon corresponds to that in *E. coli* to design a base sequence, and by chemically synthesizing a polynucleotide composed of the base sequence thus designed.

To express the present polynucleotide (B) in a host cell, for example, a polynucleotide in which a promoter which can function in a host cell is connected with the present polynucleotide (B) so that they can function is prepared, and introduced into a host cell.

Examples of the promoter which can function in a microorganism include a synthetic promoter which can function in *E. coli* as mentioned above. A promoter which controls the expression of the present polynucleotide (B) in a microorganism belonging to the genus *Bacillus* such as *Bacillus sphaericus* may be used.

The fact that the polynucleotide prepared as mentioned above encodes an amino acid sequence of a protein having the ability to aminate an α-oxocarboxylic acid compound (e.g., 2-oxo-4-(methylthio)butyric acid) and convert the same into a corresponding L-α-amino acid compound (e.g., L-methionine) can be confirmed by, for example, the following procedures.

The polynucleotide obtained as mentioned above is inserted into a vector so that the polynucleotide is connected downstream of a promoter which can function in a host cell, and the recombinant vector thus obtained is introduced into a host cell to obtain a transformant. A cultured product of the transformant thus obtained is reacted with α-oxocarboxylic acid (e.g., sulfur-containing α-oxocarboxylic acid, more specifically, 2-oxo-4-(methylthio)butyric acid). By analyzing the amount of corresponding L-α-amino acid in the reaction product (e.g., sulfur-containing L-α-amino acid, more specifically, L-methionine), the fact that the polynucleotide thus obtained encodes an amino acid sequence of a protein having target ability can be confirmed.

A transformant can be produced by introducing the present invented polynucleotide (A), the present polynucleotide (B), or a recombinant vector containing any one or both of these polynucleotides into a host cell.

Examples of the host cell include a microorganism belonging to the genus *Escherichia*, *Bacillus*, *Corynebacterium*, *Staphylococcus*, *Streptomyces*, *Saccharomyces*, *Kluyveromyces*, *Pichia*, *Rhodococcus*, or *Aspergillus*.

As mentioned above, by introducing the present invented polynucleotide (A), or a polynucleotide in which a promoter which can function in a host cell is connected with the present invented polynucleotide (A) so that they can function into a host cell, a transformant having the present invented polynucleotide (A), or a polynucleotide in which a promoter which can function in a host cell is connected with the present invented polynucleotide (A) so that they can function can be obtained. Examples of the transformant can also include a transformant in which the above exogenous polynucleotide is introduced into a chromosome of a host cell, namely a transformant having the above exogenous polynucleotide on a chromosome.

The transformant having the present invented polynucleotide (A), or a polynucleotide in which a promoter which can function in a host cell is connected with the present invented polynucleotide (A) so that they can function can also further have the present polynucleotide (B), or a polynucleotide in which a promoter which can function in a host cell is connected with the present polynucleotide (B) so that they can function.

As mentioned above, by introducing:
i) the present polynucleotide (B), or a polynucleotide in which a promoter which can function in a host cell is connected with the present polynucleotide (B) so that they can function; and
ii) the present invented polynucleotide (A), or a polynucleotide in which a promoter which can function in a host cell is connected with the present invented polynucleotide (A) so that they can function;
into a host cell, a transformant having:
i) the present polynucleotide (B), or a polynucleotide in which a promoter which can function in a host cell is connected with the present polynucleotide (B) so that they can function; and
ii) the present invented polynucleotide (A), or a polynucleotide in which a promoter which can function in a host cell is connected with the present invented polynucleotide (A) so that they can function;
can be obtained.

The above i) polynucleotide and ii) polynucleotide may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of the above i) polynucleotide and ii) polynucleotide may be on a chromosome of a host cell.

The present invented protein (A) can be produced by, for example, culturing a transformant having the present invented polynucleotide (A) to express the present invented protein (A).

The present invented protein (B) can be produced by, for example, culturing a transformant having the present polynucleotide (B) to express the present invented protein (B).

As a method for purifying the present invented protein (A) or the present invented protein (B) from a cultured product of a transformant having the present invented polynucleotide (A) or the present polynucleotide (B), a usual method used for purification of proteins can be applied.

A fraction containing the present invented protein (A) can be selected by, for example, using the ability to oxidize 2-hydroxy-4-(methyltho)butyric acid and preferentially produce 2-oxo-4-(methylthio)butyric acid as an index.

A fraction containing the present invented protein (B) can be selected by, for example, using the ability to aminate 2-oxo-4-(methylthio)butyric acid and preferentially produce L-methionine as an index.

The present invented production method 1 is a method for producing an α-oxocarboxylic acid compound, which includes the step of reacting the present invented protein (A) with an α-hydroxycarboxylic acid compound.

Examples of the above α-hydroxycarboxylic acid compound can include a sulfur-containing α-hydroxycarboxylic acid compound, and examples of the corresponding α-oxocarboxylic acid compound can include a sulfur-containing α-oxocarboxylic acid compound.

Examples of the above sulfur-containing α-hydroxycarboxylic acid compound include sulfur-containing α-hydroxycarboxylic acid represented by formula (1):

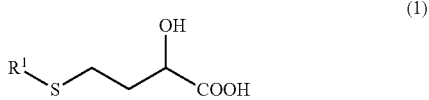

(1)

wherein R¹ represents a hydrogen atom or an optionally substituted a C1-8 alkyl group.

Examples of a sulfur-containing α-oxocarboxylic acid compound obtained by reacting the above sulfur-containing α-hydroxycarboxylic acid represented by formula (1) with the present invented protein (A) include sulfur-containing α-oxocarboxylic acid represented by formula (2):

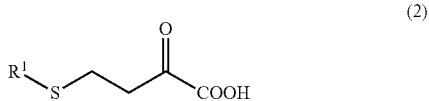

(2)

wherein R¹ is the same as defined above.

In the sulfur-containing α-hydroxycarboxylic acid represented by formula (1) and the sulfur-containing α-oxocarboxylic acid represented by formula (2), examples of a C1-8 alkyl group in the optionally substituted a C1-8 alkyl group represented by R¹ include a methyl group, an ethyl group, a propyl group, an isopropyl group, a butyl group, a pentyl group, a hexyl group, a heptyl group, and an octyl group.

Specific examples of the sulfur-containing α-hydroxycarboxylic acid represented by formula (1) can include 2-hydroxy-4-(methylthio)butyric acid, 2-hydroxy-4-(ethylthio) butyric acid, 2-hydroxy-4-(propylthio)butyric acid, 2-hydroxy-4-(butylthio)butyric acid, 2-hydroxy-4-(pentylthio)butyric acid, 2-hydroxy-4-(hexylthio)butyric acid, 2-hydroxy-4-(heptylthio)butyric acid, and 2-hydroxy-4-(octylthio)butyric acid.

Specific examples of the sulfur-containing α-oxocarboxylic acid represented by formula (2) can include 2-oxo-4-(methylthio)butyric acid, 2-oxo-4-(ethylthio)butyric acid, 2-oxo-4-(propylthio)butyric acid, 2-oxo-4-(butylthio)butyric acid, 2-oxo-4-(pentylthio)butyric acid, 2-oxo-4-(hexylthio)butyric acid, 2-oxo-4-(heptylthio)butyric acid, and 2-oxo-4-(octylthio)butyric acid.

As the optionally substituted a C1-8 alkyl group represented by R¹, a methyl group is preferable, and as the sulfur-containing α-hydroxycarboxylic acid represented by formula (1), 2-hydroxy-4-(methylthio)butyric acid is preferably exemplified.

In the present invented production method 1, when 2-hydroxy-4-(methylthio)butyric acid is used as a substrate, 2-oxo-4-(methylthio)butyric acid is obtained.

In the present invented production method 1, the present invented protein (A) can be provided to a reaction system for reaction with an α-hydroxycarboxylic acid compound, in various forms. The present invented protein (A) may be provided to a reaction system in the present invented production method 1 in the form of a purified protein, or may be provided to the reaction system in the form in which the protein is included in a microorganism producing the protein or in a treated product of the microorganism. "Treated product of microorganism" means that prepared in a similar manner to the above mentioned "treated product of transformant". The present invented protein (A) may be provided to the above reaction system in the form in which the protein is included in a transformant in which a polynucleotide encoding the protein is introduced into a host cell or in a treated product thereof.

To react the present invented protein (A) with an α-hydroxycarboxylic acid compound, specifically, for example, the present invented protein (A), an immobilized product of the present invented protein (A), a cultured product of a transformant producing the present invented protein (A) in which a polynucleotide encoding the present invented protein (A) is introduced into a host cell, or a treated product of the transformant can be provided to a reaction system in the present invented production method 1.

The present invented production method 1 is usually performed in the presence of water. Water used in this case may be a buffered aqueous solution. Examples of a buffer used for the buffered aqueous solution include tris(hydroxymethyl)aminomethane, alkali metal phosphates such as sodium phosphate or potassium phosphate, alkali metal acetates such as sodium acetate or potassium acetate, or mixtures thereof.

In the present invented production method 1, in addition to water, an organic solvent can also coexist in a reaction system. Examples of the organic solvent to be used include ethers such as t-butyl methyl ether, diisopropyl ether, and tetrahydrofuran; esters such as ethyl formate, ethyl acetate, propyl acetate, butyl acetate, ethyl propionate, and butyl propionate; hydrocarbons such as toluene, hexane, cyclohexane, heptane, and isooctane; alcohols such as methanol, ethanol, 2-propanol, butanol, t-butyl alcohol; organic sulfur compounds such as dimethyl sulfoxide; ketones such as acetone; nitriles such as acetonitrile; and mixtures thereof.

In the present invented production method 1, as the oxidation reaction of an α-hydroxycarboxylic acid compound (e.g., sulfur-containing α-hydroxycarboxylic acid such as 2-hydroxy-4-(methylthio)butyric acid) proceeds, oxygen in the reaction solution is consumed and converted into hydrogen peroxide. Since hydrogen peroxide occurred as a result of the conversion can return to the original molecular oxygen by being reacted with a protein having the ability to convert hydrogen peroxide into molecular oxygen, a protein having the ability to convert hydrogen peroxide into molecular oxygen may further exist in a reaction system in the above method.

Examples of the protein having the ability to convert hydrogen peroxide into molecular oxygen include a catalase. Examples of the catalase can include a catalase of E. coli, more specifically, a catalase having an amino acid sequence represented by SEQ ID NO: 41.

A protein having the ability to convert hydrogen peroxide into molecular oxygen may be provided to a reaction system in the present invented production method 1 in the form of a purified protein or an immobilized product thereof, or may be provided to the reaction system in the form in which the protein is included in a microorganism producing the protein or in a treated product of the microorganism. "Treated product of microorganism" means that prepared in a similar manner to the above mentioned "treated product of transformant". A transformant in which a polynucleotide encoding a protein having the ability to convert hydrogen peroxide into molecular oxygen is introduced into a host cell or a treated product thereof may be provided to the above reaction system. Examples of a base sequence encoding a catalase having an amino acid sequence represented by SEQ ID NO: 41 can include a base sequence represented by SEQ ID NO: 42.

In the present invented production method 1, a transformant in which a polynucleotide encoding the present invented protein (A) is introduced into a host cell or a treated product thereof, and a transformant in which a polynucleotide encoding a protein having the ability to convert hydrogen peroxide into molecular oxygen is introduced into a host cell or a treated product thereof may be provided to a reaction system for reaction with an α-hydroxycarboxylic acid compound.

In the present invented production method 1, a transformant in which both of a polynucleotide encoding the present invented protein (A) and a polynucleotide encoding a protein having the ability to convert hydrogen peroxide into molecular oxygen are introduced in the same host cell or a treated product thereof may be provided to the reaction system. A polynucleotide encoding the present invented protein (A) and a polynucleotide encoding a protein having the ability to convert hydrogen peroxide into molecular oxygen may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding the present invented protein (A) and a polynucleotide encoding a protein having the ability to convert hydrogen peroxide into molecular oxygen may be on a chromosome of a host cell.

A reaction in the present invented production method 1 is performed by, for example, mixing water, an α-hydroxycarboxylic acid compound (e.g., a sulfur-containing α-hydroxycarboxylic acid compound such as 2-hydroxy-4-(methylthio)butyric acid), the present invented protein (A) or a transformant producing it or a treated product thereof, and further, as needed, a reaction solution containing an organic solvent, a catalase, and the like by stirring, shaking, and the like.

The pH at the time of reaction in the above method can be appropriately selected, and is usually within a range of about 3 to about 10. The reaction temperature can be appropriately selected, and is usually within a range of about 0° C. to about 60° C. in terms of the stability and the reaction rate of raw materials and products.

The end point of the reaction can be determined by, for example, analyzing the amount of an α-hydroxycarboxylic acid compound (e.g., a sulfur-containing α-hydroxycarboxylic acid compound such as 2-hydroxy-4-(methylthio)butyric acid) in the reaction solution by liquid chromatography, etc.

The reaction time can be appropriately selected, and is usually within a range of about 0.5 hour to about 10 days.

Recovery of α-oxocarboxylic acid (e.g., a sulfur-containing α-oxocarboxylic acid compound such as 2-oxo-4-(methylthio)butyric acid) from the reaction solution may be performed by a generally known arbitrary method.

Example thereof include a method for purifying a target compound by performing post-treatment operations of the reaction solution such as extraction with an organic solvent and concentration in combination with column chromatography, distillation, or the like as needed.

The present invented production method 2 is a method for producing an L-α-amino acid compound, which includes:
(1) the step of reacting the present invented protein (A) with an α-hydroxycarboxylic acid compound to obtain a corresponding α-oxocarboxylic acid compound, and
(2) the step of reacting a protein having the ability to aminate an α-oxocarboxylic acid compound and convert the same into a corresponding L-α-amino acid compound (the present invented protein (B)) with the α-oxocarboxylic acid compound obtained in the step (1) to obtain a corresponding L-α-amino acid compound.

Examples of the above α-hydroxycarboxylic acid include sulfur-containing α-hydroxycarboxylic acid represented by formula (1):

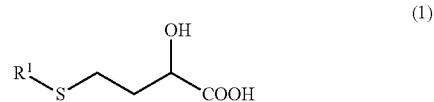

wherein $R^1$ represents a hydrogen atom or an optionally substituted C1-8 alkyl group.

Examples of a sulfur-containing α-oxocarboxylic acid compound obtained by reacting the above sulfur-containing α-hydroxycarboxylic acid represented by formula (1) with the present invented protein (A) include sulfur-containing α-oxocarboxylic acid represented by formula (2):

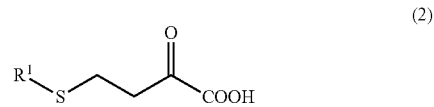

wherein $R^1$ is the same as defined above.

Examples of a sulfur-containing L-α-amino acid compound obtained by reacting the above sulfur-containing α-oxocarboxylic acid represented by formula (2) with the present invented protein (B) include sulfur-containing L-α-amino acid represented by formula (3):

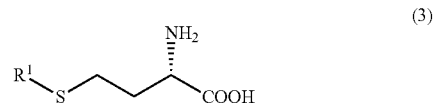

In the sulfur-containing α-hydroxycarboxylic acid represented by formula (1), the sulfur-containing α-oxocarboxylic acid represented by formula (2), and the sulfur-containing L-α-amino acid represented by formula (3), examples of a C1-8 alkyl group in the optionally substituted C1-8 alkyl group represented by $R^1$ include a methyl group, an ethyl group, a propyl group, an isopropyl group, a butyl group, a pentyl group, a hexyl group, a heptyl group, and an octyl group.

Specific examples of the sulfur-containing α-hydroxycarboxylic acid represented by formula (1) can include 2-hydroxy-4-(methylthio)butyric acid, 2-hydroxy-4-(ethylthio)butyric acid, 2-hydroxy-4-(propylthio)butyric acid, 2-hydroxy-4-(butylthio)butyric acid, 2-hydroxy-4-(pentylthio)butyric acid, 2-hydroxy-4-(hexylthio)butyric acid, 2-hydroxy-4-(heptylthio)butyric acid, and 2-hydroxy-4-(octylthio)butyric acid.

Specific examples of the sulfur-containing α-oxo carboxylic acid represented by formula (2) can include 2-oxo-4-(methylthio)butyric acid, 2-oxo-4-(ethylthio)butyric acid, 2-oxo-4-(propylthio)butyric acid, 2-oxo-4-(butylthio)butyric acid, 2-oxo-4-(pentylthio)butyric acid, 2-oxo-4-(hexylthio)butyric acid, 2-oxo-4-(heptylthio)butyric acid, and 2-oxo-4-(octylthio)butyric acid.

Specific examples of the sulfur-containing L-α-amino acid represented by formula (3) can include 2-amino-4-(methylthio)butyric acid, 2-amino-4-(ethylthio)butyric acid, 2-amino-4-(propylthio)butyric acid, 2-amino-4-(butylthio)butyric acid, 2-amino-4-(pentylthio)butyric acid, 2-amino-4-(hexylthio)butyric acid, 2-amino-4-(heptylthio)butyric acid, and 2-amino-4-(octylthio)butyric acid.

As the optionally substituted C1-8 alkyl group represented by $R^f$, a methyl group is preferable, and as the sulfur-containing α-hydroxycarboxylic acid represented by formula (1), 2-hydroxy-4-(methylthio)butyric acid is preferably exemplified.

In the step (1) of the present invented production method 2, when 2-hydroxy-4-(methylthio)butyric acid is used as a substrate, 2-oxo-4-(methylthio)butyric acid is obtained in the step (1) and L-methionine is obtained in the step (2).

The step (1) of the present invented production method 2 can be performed in a similar manner to the present invented production method 1.

An α-oxocarboxylic acid (e.g., a sulfur-containing α-oxocarboxylic acid compound such as 2-oxo-4-(methylthio)butyric acid) obtained in the step (1) is purified or partially purified from the reaction solution, and then can be subjected to the step (2). By adding the reaction solution in the step (1) to the step (2), an α-oxocarboxylic acid (e.g., a sulfur-containing α-oxocarboxylic acid compound such as 2-oxo-4-(methylthio)butyric acid) obtained in the step (1) can also be subjected to the step (2).

In the step (2) of the present invented production method 2, the present invented protein (B) can be provided to a reaction system for reaction with an α-oxocarboxylic acid compound, in various forms. The present invented protein (B) may be provided to a reaction system in the above step (2) in the form of a purified protein, or may be provided to the reaction system in the form in which the protein is included in a microorganism producing the protein or in a treated product of the microorganism. "Treated product of microorganism" means that prepared in a similar manner to the above mentioned "treated product of transformant". The present invented protein (B) may be provided to the above reaction system in the form in which the protein is included in a transformant in which a polynucleotide encoding the protein is introduced into a host cell or in a treated product thereof.

To react the present invented protein (B) with an α-oxocarboxylic acid compound, specifically, for example, the present invented protein (B), an immobilized product of the present invented protein (B), a cultured product of a transformant producing the present invented protein (B) in which a polynucleotide encoding the present invented protein (B) is introduced into a host cell, or a treated product of the transformant can be provided to a reaction system in the above step (2).

The step (2) of the present invented production method 2 is usually performed in the presence of water, an ammonium ion, and a coenzyme.

Water used in this case may be a buffered aqueous solution. Examples of a buffer used for the buffered aqueous solution include tris(hydroxymethyl)aminomethane, alkali metal phosphates such as sodium phosphate or potassium phosphate, alkali metal acetates such as sodium acetate or potassium acetate, or mixtures thereof.

In the step (2) of the present invented production method 2, in addition to water, an organic solvent can also coexist in a reaction system. Examples of the organic solvent to be used include ethers such as t-butyl methyl ether, diisopropyl ether, and tetrahydrofuran; esters such as ethyl formate, ethyl acetate, propyl acetate, butyl acetate, ethyl propionate, and butyl propionate; hydrocarbons such as toluene, hexane, cyclohexane, heptane, and isooctane; alcohols such as methanol, ethanol, 2-propanol, butanol, and t-butyl alcohol; organic sulfur compounds such as dimethyl sulfoxide; ketones such as acetone; nitriles such as acetonitrile; and mixtures thereof.

In the step (2) of the present invented production method 2, since an ammonium ion is used as an amino group donor, usually an ammonium salt compound is added to a reaction system. Examples of the ammonium salt compound to be added can include ammonium sulfate, ammonium formate, ammonium chloride, ammonium nitrate, ammonium phosphate, ammonium hydroxide, ammonium tartrate, and ammonium acetate. The amount of an ammonium ion in the reaction system is usually equimolar to or more than the amount of an α-oxocarboxylic acid compound as a substrate, and the ammonium ion is preferably added at the start of reaction.

In the step (2) of the present invented production method 2, since a cofactor is used as a conjugated system, usually it is better to add a coenzyme to a reaction system. Examples of the coenzyme to be added can include reduced β-nicotinamide adenine dinucleotide (hereinafter sometimes referred to as NADH) and reduced β-nicotinamide adenine dinucleotide phosphate (hereinafter sometimes referred to as NADPH). The amount of a cofactor in the reaction system is usually equimolar to or more than the amount of an α-oxocarboxylic acid compound as a substrate, and the cofactor is preferably added at the start of reaction.

In the step (2) of the present invented production method 2, as the reductive amination reaction of α-oxocarboxylic acid (e.g., sulfur-containing α-oxocarboxylic acid such as 2-oxo-4-(methylthio)butyric acid) proceeds, NADH in the reaction solution is converted into oxidized β-nicotinamide adenine dinucleotide (hereinafter sometimes referred to as NAD+). Since NAD+ occurred as a result of the conversion can return to the original NADH by being reacted with a protein having the ability to convert NAD+ into its reduced form (NADH), a protein having the ability to convert NAD+ into NADH may further exist in a reaction system in the above step (2). When a protein having the ability to convert NAD+ into NADH further exists in a reaction system in the above step (2), the amount of a cofactor in the reaction system may be usually a catalytic amount, and equimolar to or less than the amount of an α-oxocarboxylic acid compound as a substrate.

Examples of the protein having the ability to convert NAD+ into NADH include organic acid dehydrogenases such as a formate dehydrogenase and a malate dehydrogenase; a glucose dehydrogenase, an alcohol dehydrogenase, an aldehyde dehydrogenase, or an amino acid dehydrogenase. Examples of the formate dehydrogenase can include a formate dehydrogenase of a microorganism belonging to the genus *Bacillus*, more specifically, a formate dehydrogenase having an amino acid sequence represented by SEQ ID NO: 43.

A protein having the ability to convert NAD+ into NADH may be provided to a reaction system in the step (2) of the present invented production method 2 in the form of a purified protein or an immobilized product thereof, or may be provided to the reaction system in the form in which the protein is included in a microorganism producing the protein or in a treated product of the microorganism. "Treated product of microorganism" means that prepared in a similar manner to the above mentioned "treated product of transformant". A transformant in which a polynucleotide encoding a protein having the ability to convert NAD+ into NADH is introduced into a host cell or a treated product thereof may be provided to the above reaction system.

In the step (2) of the present invented production method 2, a transformant in which a polynucleotide encoding the present invented protein (B) is introduced into a host cell or a treated product thereof, and a transformant in which a polynucleotide encoding a protein having the ability to convert NAD4 into NADH is introduced into a host cell or a treated product thereof may be provided to a reaction system for reaction with an α-oxocarboxylic acid compound.

In the step (2) of the present invented production method 2, a transformant in which both of a polynucleotide encoding the present invented protein (B) and a polynucleotide encoding a protein having the ability to convert NAD+ into NADH are introduced in the same host cell or a treated product thereof may be provided to the reaction system. A polynucleotide encoding the present invented protein (B) and a polynucleotide encoding a protein having the ability to convert NAD+ into NADH may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding the present invented protein (B) and a polynucleotide encoding a protein having the ability to convert NAD+ into NADH may be on a chromosome of a host cell.

A reaction in the step (2) of the present invented production method 2 is performed by, for example, mixing water, an ammonium salt compound, NADH, an α-oxocarboxylic acid compound (e.g., a sulfur-containing α-oxocarboxylic acid compound such as 2-oxo-4-(methylthio)butyric acid), the present invented protein (B) or a transformant producing it or a treated product thereof, and further, as needed, a reaction solution containing an organic solvent, a protein having the ability to convert NAD+ into NADH, and the like by stirring, shaking, and the like.

When the protein having the ability to convert NAD+ into NADH is a glucose dehydrogenase, the activity of the protein is sometimes enhanced by coexistence of glucose, etc. in the reaction system, and, for example, glucose, etc. may be added to the reaction solution. When the protein having the ability to convert NAD+ into NADH is a formate dehydrogenase, the activity of the protein is sometimes enhanced by coexistence of ammonium formate as an amino group donor in the reaction system, and, for example, ammonium formate may be added to the reaction solution.

The pH at the time of reaction in the above method can be appropriately selected, and is usually within a range of about 3 to about 10. The reaction temperature can be appropriately selected, and is usually within a range of about 0° C. to about 60° C. in terms of the stability and the reaction rate of raw materials and products.

The end point of the reaction can be determined by, for example, analyzing the amount of an α-oxocarboxylic acid compound (e.g., a sulfur-containing α-oxocarboxylic acid compound such as 2-oxo-4-(methylthio)butyric acid) in the reaction solution by liquid chromatography, etc.

The reaction time can be appropriately selected, and is usually within a range of about 0.5 hour to about 10 days.

Recovery of L-α-amino acid (e.g., sulfur-containing L-α-amino acid such as L-methionine) from the reaction solution may be performed by a generally known arbitrary method. Example thereof include a method for purifying a target compound by performing post-treatment operations of the reaction solution such as crystallization, extraction with an organic solvent, and concentration in combination with column chromatography, distillation, or the like as needed.

The step (1) and step (2) of the present invented production method 2 can be performed in one reaction system. In this case, the present invented protein (A) and the present invented protein (B) can be provided to the above reaction system in different various forms.

The present invented protein (A) and the present invented protein (B) may be provided to the above reaction system in the form of a purified protein, or may be provided to the above reaction system in the form in which the proteins are included in a microorganism producing these proteins or in a treated product of the microorganism.

The present invented protein (A) and the present invented protein (B) may be provided to the above reaction system in the form in which the proteins are included in a transformant in which a polynucleotide encoding these proteins is introduced into a host cell or in a treated product thereof.

For example, a transformant in which a polynucleotide encoding the present invented protein (A) is introduced into a host cell or a treated product thereof, and a transformant in which a polynucleotide encoding the present invented protein (B) is introduced into a host cell or a treated product thereof may be provided to the above reaction system. A transformant in which both of a polynucleotide encoding the present invented protein (A) and a polynucleotide encoding the present invented protein (B) are introduced into the same host cell or a treated product thereof may be provided to the above reaction system. A polynucleotide encoding the present invented protein (A) and a polynucleotide encoding the present invented protein (B) may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding the present invented protein (A) and a polynucleotide encoding the present invented protein (B) may be on a chromosome of a host cell.

A protein having the ability to convert hydrogen peroxide into molecular oxygen or a protein having the ability to convert NAD+ into NADH, or both of these proteins may further exist in the above reaction system. A protein having the ability to convert hydrogen peroxide into molecular oxygen and a protein having the ability to convert NAD+ into NADH may be provided to the above reaction system in the form of a purified protein or an immobilized product thereof, or may be provided to the above reaction system in the form in which the proteins are included in a microorganism producing these proteins or in a treated product of the microorganism. A transformant in which a polynucleotide encoding a protein having the ability to convert hydrogen peroxide into molecular oxygen or a polynucleotide encoding a protein having the ability to convert NAD+ into NADH is introduced into a host cell or a treated product thereof may be provided to the above reaction system.

A transformant in which two or more polynucleotides selected from the group consisting of a polynucleotide encoding the present invented protein (A), a polynucleotide encoding the present invented protein (B), a polynucleotide encoding a protein having the ability to convert hydrogen peroxide into molecular oxygen, and a polynucleotide encoding a protein having the ability to convert NAD+ into NADH are introduced into the same host cell or a treated product thereof may be provided to the above reaction system.

A reaction when the step (1) and the step (2) of the present invented production method 2 are performed in one reaction system can be performed in a reaction solution and under a reaction condition in accordance with the reaction in the step (2) of the present invented production method 2 mentioned above.

The end point of the reaction can be determined by, for example, analyzing the amount of an α-hydroxycarboxylic acid compound (e.g., a sulfur-containing α-hydroxycarboxylic acid compound such as 2-hydroxy-4-(methylthio)butyric acid) in the reaction solution by liquid chromatography, etc.

The reaction time can be appropriately selected, and is usually within a range of about 0.5 hour to about 10 days.

Recovery of L-α-amino acid (e.g., sulfur-containing L-α-amino acid such as L-methionine) from the reaction solution may be performed in the same manner as in the step (2) of the present invented production method 2 mentioned above.

EXAMPLES

The present invention will be described in more detail below by way of Examples, etc., but the present invention is not limited to these Examples.

Reference Example 1

Preparation of Chromosomal DNA

Into each of two 500 ml flasks, 100 ml of a medium (2 g of glucose, 0.5 g of polypeptone, 0.3 g of yeast extract, 0.3 g of meat extract, 0.2 g of ammonium sulfate, 0.1 g of potassium dihydrogenphosphate, 0.05 g of magnesium sulfate heptahydrate were dissolved in 100 ml of water, and the pH was adjusted to 6 with 2 N HCl) was put, and the medium was sterilized at 121° C. for 15 minutes. To each thereof, 0.3 ml of a culture solution of an *Achromobacter denitrificans* ATCC55564 strain which was cultured by shaking in a medium of the same composition at 30° C. for 48 hours was added, and the medium was cultured by shaking at 30° C. for 24 hours. The culture solution thus obtained was centrifuged at 8,000 rpm and 4° C. for 10 minutes and the precipitate thus produced was collected. The precipitate thus obtained was washed with 50 ml of 0.85% saline to obtain 3.5 g of wet cells.

From the cells thus obtained, chromosomal DNA (hereinafter referred to as the chromosomal DNA (A)) was obtained using the QIAprep Genomic-tip System (manufactured by Qiagen).

Example 1 (Preparation of Present Invented Polynucleotide (A), Present Invented Recombinant Vector, and Transformant of Present Invention)

Oligonucleotide primers each having a base sequence represented by any one of SEQ ID NO: 9 to 14 are synthesized.

TABLE 1

| Sense primer | Antisense primer |
|---|---|
| SEQ ID NO: 9<br>CCATGAGCCGGCTGGACCG<br>CTGCCTGTC | SEQ ID NO: 10<br>GGATCCCTATGCCGGGCTGG<br>CCGGCCGTATC |
| SEQ ID NO: 11<br>CCATATGAACTCAAAGAAA<br>CTCTTGTCGATAG | SEQ ID NO: 12<br>GGATCCCTAAGGGCGCGACA<br>CGATGAAGTCG |
| SEQ ID NO: 13<br>CCATATGACATCCATCCTT<br>CCGTCCGTCACC | SEQ ID NO: 14<br>GGATCCCTAATCTGCCAGGC<br>TCTCGCGGGCC |

Using an oligonucleotide primer having a base sequence represented by SEQ ID NO: 9 and an oligonucleotide primer having a base sequence represented by SEQ ID NO: 10, PCR was performed using the above chromosomal DNA (A) as a template and with the following reaction solution composition.

[Reaction Solution Composition]

| Chromosomal DNA (A) solution: | 1.5 μl |
| dNTP (a mixture of 2 mM each): | 10 μl |
| Primer (50 pmol/μl): | 0.3 μl each |
| 2x buffer: | 25 μl |
| KOD-FX (1 U/μl, Toyobo): | 1 μl |
| Ultrapure water: | 11.9 μl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.2 kb was detected.

By adding restriction enzymes NdeI and BamHI to the remaining PCR reaction solution, DNA was double-digested, and enzymatically digested DNA of about 1.2 kb was purified.

Plasmid vector pET-22b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NdeI and BamHI, and then subjected to agarose gel electrophoresis. In each of six plasmids, DNA of about 1.2 kb was confirmed to be inserted into the above vector. When the base sequence of the inserted DNA of about 1.2 kb of one of these plasmids was analyzed, it was found that the DNA has a base sequence represented by SEQ ID NO: 2. This plasmid was designated as pET174. A base sequence represented by SEQ ID NO: 2 encodes an amino acid sequence represented by SEQ ID NO: 1.

Using an oligonucleotide primer having a base sequence represented by SEQ ID NO: 11 and an oligonucleotide primer having a base sequence represented by SEQ ID NO: 12, PCR was performed using the above chromosomal DNA (A) as a template and with the following reaction solution composition.
[Reaction Solution Composition]

| | |
|---|---|
| Chromosomal DNA (A) solution: | 1.5 µl |
| dNTP (a mixture of 2 mM each): | 10 µl |
| Primer (50 pmol/µl): | 0.3 µl each |
| 2x buffer: | 25 µl |
| KOD-FX (1 U/µl, Toyobo): | 1 µl |
| Ultrapure water: | 11.9 µl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.2 kb was detected.

By adding restriction enzymes NdeI and BamHI to the remaining PCR reaction solution, DNA was double-digested, and enzymatically digested DNA of about 1.2 kb was purified.

Plasmid vector pET-22b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, E. coli DH5α was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NdeI and BamHI, and then subjected to agarose gel electrophoresis. In each of six plasmids, DNA of about 1.2 kb was confirmed to be inserted into the above vector. When the base sequence of the inserted DNA of about 1.2 kb of one of these plasmids was analyzed, it was found that the DNA has a base sequence represented by SEQ ID NO: 4. This plasmid was designated as pET204. A base sequence represented by SEQ ID NO: 4 encodes an amino acid sequence represented by SEQ ID NO: 3.

Using an oligonucleotide primer having a base sequence represented by SEQ ID NO: 13 and an oligonucleotide primer having a base sequence represented by SEQ ID NO: 14, PCR was performed using the above chromosomal DNA (A) as a template and with the following reaction solution composition.
[Reaction Solution Composition]

| | |
|---|---|
| Chromosomal DNA (A) solution: | 1.5 µl |
| dNTP (a mixture of 2 mM each): | 10 µl |
| Primer (50 pmol/µl): | 0.3 µl each |
| 2x buffer: | 25 µl |
| KOD-FX (1 U/µl, Toyobo): | 1 µl |
| Ultrapure water: | 11.9 µl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.2 kb was detected.

By adding restriction enzymes NdeI and BamHI to the remaining PCR reaction solution, DNA was double-digested, and enzymatically digested DNA of about 1.2 kb was purified.

Plasmid vector pET-22b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, E. coli DH5α was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NdeI and BamHI, and then subjected to agarose gel electrophoresis. In each of six plasmids, DNA of about 1.2 kb was confirmed to be inserted into the above vector. When the base sequence of the inserted DNA of about 1.2 kb of one of these plasmids was analyzed, it was found that the DNA has a base sequence represented by SEQ ID NO: 6. This plasmid was designated as pET436. A base sequence represented by SEQ ID NO: 6 encodes an amino acid sequence represented by SEQ ID NO: 5.

Example 2 (Preparation of L-α-Amino Acid Compound Using Treated Product of Transformant of Present Invention)

An E. coli BL21(DE3) strain was transformed using the plasmid pET174. The transformant thus obtained was inoculated into 10 ml of a sterilized LB medium containing 0.1 mM IPTG and 50 µg/ml of ampicillin, and the medium was cultured by shaking at 37° C. for 15 hours. The culture solution thus obtained was centrifuged to obtain wet cells. About 1 g of the wet cells were suspended in I ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.45 ml of the centrifuged supernatant liquid thus obtained, 1.0 mg of a calcium salt of 2-hydroxy-4-(methylthio)butyric acid (manufactured by Tokyo Chemical Industry), 2.5 mg of NADH, 0.05 ml of 100 mM Tris-HCl buffer (pH 8.0), 0.2 mg of ammonium sulfate, and 0.4 U of a leucine dehydrogenase (Wako Pure Chemical Industries) were mixed, and the solution was shaken at 30°

C. for 22 hours. This reaction solution was subjected to content analysis by liquid chromatography under the following condition. It was found that L-methionine was produced in a proportion of 1.6% based on the amount of a calcium salt of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An E. coli BL21(DE3) strain was transformed using the plasmid pET204. The transformant thus obtained was inoculated into 10 ml of a sterilized LB medium containing 0.1 mM IPTG and 50 μg/ml of ampicillin, and the medium was cultured by shaking at 37° C. for 15 hours. The culture solution thus obtained was centrifuged to obtain wet cells. About 1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 0.7 ml of centrifuged supernatant liquid. With 0.45 ml of the centrifuged supernatant liquid thus obtained, 1.0 mg of a calcium salt of 2-hydroxy-4-(methylthio)butyric acid (manufactured by Tokyo Chemical Industry), 2.5 mg of NADH, 0.05 ml of 100 mM Tris-HCl buffer (pH 8.0), 0.2 mg of ammonium sulfate, and 0.4 U of a leucine dehydrogenase (Wako Pure Chemical Industries) were mixed, and the solution was shaken at 30° C. for 22 hours. This reaction solution was subjected to content analysis by liquid chromatography under the following condition. It was found that L-methionine was produced in a proportion of 2.8% based on the amount of a calcium salt of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An E. coli BL21(DE3) strain was transformed using the plasmid pET436. The transformant thus obtained was inoculated into 10 ml of a sterilized LB medium containing 0.1 mM IPTG and 50 μg/ml of ampicillin, and the medium was cultured by shaking at 37° C. for 15 hours. The culture solution thus obtained was centrifuged to obtain wet cells. About 1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.45 ml of the centrifuged supernatant liquid thus obtained, 1.0 mg of a calcium salt of 2-hydroxy-4-(methylthio)butyric acid (manufactured by Tokyo Chemical Industry), 2.5 mg of NADH, 0.05 ml of 100 mM Tris-HCl buffer (pH 8.0), 0.2 mg of ammonium sulfate, and 0.4 U of a leucine dehydrogenase (Wako Pure Chemical Industries) were mixed, and the solution was shaken at 30° C. for 22 hours. This reaction solution was subjected to content analysis by liquid chromatography under the following condition. It was found that L-methionine was produced in a proportion of 3.9% based on the amount of a calcium salt of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 3 (Preparation of Recombinant Vector Containing Polynucleotide Encoding Present Protein (B) and Transformant Having the Vector, and Preparation of Present Protein (B))

(1) Preparation of Recombinant Vector Containing Polynucleotide Encoding Amino Acid Sequence of Present Protein (B) and Transformant Having the Vector (1)

A *Bacillus sphaericus* IFO3525 strain was cultured in 100 ml of a sterilized LB medium to obtain 0.4 g of cells. From the cells, chromosomal DNA (hereinafter referred to as the chromosomal DNA (B)) was purified using the Qiagen Genomic Tip (manufactured by Qiagen) in accordance with the method mentioned in the manual attached thereto.

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide primer having a base sequence represented by SEQ ID NO: 18 (GCCATG-GAAATCTTCAAGTATATGG) and an oligonucleotide primer having a base sequence represented by SEQ ID NO: 19 (GGGCCCGGGTTAACGGCCGTTCAAAATATT) are synthesized.

Using an oligonucleotide primer having a base sequence represented by SEQ ID NO: 18 and an oligonucleotide primer having a base sequence represented by SEQ ID NO: 19, PCR was performed using the above chromosomal DNA (B) as a template and with the following reaction solution composition using the Expand High Fidelity PCR System (Roche Diagnostics).

[Reaction Solution Composition]

| | |
|---|---|
| Chromosomal DNA (B) solution: | 1 μl |
| dNTP (a mixture of 2.5 mM each): | 1 μl |
| Primer (20 pmol/μl): | 0.4 μl |
| Primer (4 pmol/μl): | 2 μl |
| 5x buffer (with MgCl$_2$): | 10 μl |
| enz.expandHiFi (3.5 × 10$^3$ U/ml): | 0.5 μl |
| Ultrapure water: | 35.1 μl |

A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 20 seconds, followed by 55° C. for 30 seconds, followed by 72° C. for 1.5 minutes was performed 25 times, and further the solution was maintained at 72° C. for 7 minutes.

Subsequently, a part of the above PCR reaction solution was subjected to agarose gel electrophoresis. A DNA band of about 1.1 kb was detected.

By adding restriction enzymes NcoI and SmaI to the remaining PCR reaction solution, DNA was double-digested, and enzymatically digested DNA of about 1.1 kb was purified.

Plasmid vector pTrc99A (manufactured by GE Healthcare Japan) was double-digested with restriction enzymes NcoI and SmaI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and XbaI, and then subjected to agarose gel electrophoresis. In each of six plasmids, DNA of about 1.1 kb was confirmed to be inserted into the above vector. One of these plasmids was designated as pTrcLD.

(2) Preparation of Recombinant Vector Containing Polynucleotide Encoding Amino Acid Sequence of Present Protein (B) and Transformant Having the Vector (2)

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide having a base sequence represented by SEQ ID NO: 20 (GTCGCTATAT-TACCGGTGAAGATGTTG) (sense primer) and an oligonucleotide having a base sequence represented by SEQ ID NO: 21 (CAACATCTTCACCGGTAATATAGCGAC) (antisense primer) are synthesized as a primer for mutation introduction for substituting the 113th alanine in the enzyme by glycine. Using an oligonucleotide having a base sequence represented by SEQ ID NO: 20 and an oligonucleotide having a base sequence represented by SEQ ID NO: 21 as a primer, PCR was performed using the recombinant vector pTrcLD prepared in the above (1) as a template and with the following reaction solution composition using the QuikChange II Site-Directed Mutagenesis Kit (STRATAGENE).

[Reaction Solution Composition]

| | |
|---|---|
| DNA solution of pTrcLD: | 0.4 μl |
| dNTP mix (contained in the above Kit): | 1 μl |
| Sense primer (50 μM): | 0.4 μl |
| Antisense primer (50 μM): | 0.4 μl |
| 10x buffer (contained in the above Kit): | 5 μl |
| PfuUltra (contained in the above Kit): | 1 μl |
| Ultrapure water: | 41.8 μl |

A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 55° C. for one minute, followed by 68° C. for 5 minutes was performed 12 times, and then the solution was stored at 4° C.

To the PCR reaction solution thus obtained, 1 μl of a DpnI restriction enzyme (contained in the above Kit) was added, and then the solution was incubated at 37° C. for one hour. Using the incubated solution thus obtained, *E. coli* DH5α was transformed.

From each of the transformants thus obtained, plasmids were extracted, and then a base sequence at the mutation site was determined by the dideoxy method to confirm that the designed mutation was introduced. A plasmid having a base sequence represented by SEQ ID NO: 8 was designated as pTrcLD(A113G). A base sequence represented by SEQ ID NO: 8 encodes an amino acid sequence represented by SEQ ID NO: 7.

(3) Preparation of Recombinant Vector Containing Polynucleotide Encoding Amino Acid Sequence of Present Protein (B) and Transformant Having the Vector (3)

(3-1) Introduction of Site-Specific Mutation for Base Substitution

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide having a base sequence represented by SEQ ID NO: 22 (GATAGTATTC-CAACCTATGTTGCGGC) (sense primer) and an oligonucleotide having a base sequence represented by SEQ ID NO: 23 (GCCGCAACATAGGTTGGAATACTATC) (antisense primer) are synthesized as a primer for mutation introduction for substituting the 993rd adenine by cytosine. Using an oligonucleotide having a base sequence represented by SEQ ID NO: 22 and an oligonucleotide having a base sequence represented by SEQ ID NO: 23 as a primer, PCR was performed using the recombinant vector pTrcLD (A113G) prepared in the above (2) as a template and with the following reaction solution composition using the QuikChange II Site-Directed Mutagenesis Kit (STRATAGENE).

[Reaction Solution Composition]

| | |
|---|---|
| DNA solution of pTrcLD(A113G): | 1 μl |
| dNTP mix (contained in the above Kit): | 1 μl |
| Sense primer (50 μM): | 0.4 μl |
| Antisene primer (50 μM): | 0.4 μl |
| 10x buffer (contained in the above Kit): | 5 μl |
| PfuUltra (contained in the above Kit): | 1 μl |
| Ultrapure water: | 41.2 μl |

A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 μl of a DpnI restriction enzyme (contained in the above Kit) was added, and then the solution was incubated at 37° C. for one hour. Using the incubated solution thus obtained, *E. coli* DH5α was transformed.

From each of the transformants thus obtained, plasmids were extracted, and then a base sequence at the mutation site was determined by the dideoxy method. A plasmid into which the designed mutation was confirmed to be introduced was designated as pTrcLD(A113G)nd.

(3-2) Preparation of Recombinant Vector Containing Polynucleotide Encoding Amino Acid Sequence of Present Protein (B) and Transformant Having the Vector Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide primer having a base sequence represented by SEQ ID NO: 24 (GGGCATATG-GAAATCTTCAAGTATATGG) (sense primer) and an oligonucleotide primer having a base sequence represented by SEQ ID NO: 25 (GGATCCTTAACGGCCGTTCAAAAT-ATT) (antisense primer) are synthesized. Using an oligonucleotide primer having a base sequence represented by SEQ ID NO: 24 and an oligonucleotide primer having a base sequence represented by SEQ ID NO: 25 as a primer, PCR was performed using the recombinant vector pTrcLD (A113G)nd prepared in the above (3-1) as a template and with the following reaction solution composition using the Expand High Fidelity PCR System (Roche Diagnostics).

[Reaction Solution Composition]

| | |
|---|---|
| DNA solution of pTrcLD(A113G)nd: | 1 µl |
| dNTP (a mixture of 2.5 mM each): | 1 µl |
| Primer (20 pmol/µl): | 0.4 µl each |
| 5x buffer (with MgCl$_2$): | 10 µl |
| enz.expandHiFi (3.5 × 10$^3$ U/ml): | 0.5 µl |
| Ultrapure water: | 36.7 µl |

A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.1 kb was detected.

By adding restriction enzymes NdeI and BamHI to the remaining PCR reaction solution, DNA was double-digested, and enzymatically digested DNA of about 1.1 kb was purified.

Plasmid vector pET-15b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 µg/ml of ampicillin, 10 colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NdeI and BamHI, and then subjected to agarose gel electrophoresis. In each of four plasmids, DNA of about 1.1 kb was confirmed to be inserted into the above vector. The plasmids thus obtained are designed so that they can express a protein in which an amino acid sequence composed of 20 amino acids including consecutive 6 residues of histidine (SEQ ID NO: 44: Met-GlySerSerHisHisHisHisHisHisSerSerGlyLeuValProArg-GlySerHis) is added to the amino terminus of a leucine dehydrogenase encoded by the recombinant vector pTrcLD (A113G)nd. One of the plasmids thus obtained was designated as pETLD(A113G).

(4) Preparation of Present Protein (B)

An *E. coli* BL21(DE3) strain was transformed using the recombinant vector pETLD(A113G). The transformant thus obtained was inoculated into 100 ml of a sterilized LB medium containing 0.1 mM IPTG and 50 µg/ml of ampicillin, and the medium was cultured by shaking at 30° C. for 15 hours. The culture solution thus obtained was centrifuged to obtain about 0.8 g of wet cells. About 0.8 g of the wet cells were suspended in 10 ml of 20 mM phosphate buffer (pH 7.4) containing 0.5 M NaCl and 5 mM imidazole (hereinafter sometimes referred to as the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 7 ml of centrifuged supernatant liquid.

To about 7 ml of the centrifuged supernatant liquid thus obtained, 3 ml of the binding buffer was added to make about 10 ml, and then this liquid was applied to a HisTrap HP column (gel bed 5 ml) (manufactured by GE Healthcare Japan) with a flow rate of 5 ml/min. By passing about 25 ml of the binding buffer through this column with a flow rate of 5 ml/min, non-adsorbed proteins were eluted. Then, while maintaining the flow rate, by passing about 35 ml of 20 mM phosphate buffer (pH 7.4) containing 0.5 M NaCl and 29.75 mM imidazole through the column, non-adsorbed proteins and low adsorbed proteins were eluted. Next, adsorbed proteins were eluted by gradient elution in which the imidazole concentration was increased from 29.75 mM to 500 mM while 47.5 ml was passed through, and 25 ml of a fraction with the imidazole concentration of about 160 mM to 443 mM was collected. The fraction thus obtained was subjected to the Amicon Ultra-15 (manufactured by Merck Millipore), and desalting and concentration was performed and the buffer was replaced by 0.5 M Tris-HCl (pH 9) to obtain about 1.5 ml of a fraction. This fraction is hereinafter referred to as the leucine dehydrogenase (A113G) purified enzyme solution.

Example 4 (Preparation of L-α-Amino Acid Compound Using Treated Product of Transformant of Present Invention)

An *E. coli* BL21(DE3) strain was transformed using the plasmid pET174. The transformant thus obtained was inoculated into 10 ml of a sterilized LB medium containing 0.1 mM IPTG and 50 µg/ml of ampicillin, and the medium was cultured by shaking at 37° C. for 15 hours. The culture solution thus obtained was centrifuged to obtain wet cells. About 1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 10 mg of NAD+, 2 U of a formate dehydrogenase (Sigma-Aldrich), 2.5 mg of ammonium formate, and 0.1 ml of the leucine dehydrogenase (A113G) purified enzyme solution obtained in Example 3 (36 g protein/l) were mixed, and the solution was shaken at 30° C. for 16 hours. This reaction solution was subjected to content analysis by liquid chromatography under the following condition. It was found that L-methionine was produced in a proportion of 1.7% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET204. The transformant thus obtained was inoculated into 10 ml of a sterilized LB medium containing 0.1 mM IPTG and 50 g/ml of ampicillin, and the medium was cultured by shaking at 37° C. for 15 hours. The culture solution thus obtained was centrifuged to obtain wet cells. About 1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 10 mg of NAD+, 2 U of a formate dehydrogenase (Sigma-Aldrich), 2.5 mg of ammonium formate, and 0.1 ml of the leucine dehydrogenase (A113G) purified enzyme solution obtained in Example 3 (36 g protein/l) were mixed, and the solution was shaken at 30° C. for 16 hours. This reaction solution was subjected to content analysis by liquid chromatography under the following condition. It was found that L-methionine was produced in a proportion of 9.7% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET436. The transformant thus obtained was inoculated into 10 ml of a sterilized LB medium containing 0.1 mM IPTG and 50 μg/ml of ampicillin, and the medium was cultured by shaking at 37° C. for 15 hours. The culture solution thus obtained was centrifuged to obtain wet cells. About 1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 10 mg of NAD+, 2 U of a formate dehydrogenase (Sigma-Aldrich), 2.5 mg of ammonium formate, and 0.1 ml of the leucine dehydrogenase (A113G) purified enzyme solution obtained in Example 3 (36 g protein/l) were mixed, and the solution was shaken at 30° C. for 16 hours. This reaction solution was subjected to content analysis by liquid chromatography under the following condition. It was found that L-methionine was produced in a proportion of 6.7% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 2:10 nm Example 5 (Preparation of Present Invented Polynucleotide (A), Present Invented Recombinant Vector, and Transformant of Present Invention)

Double-stranded DNA having a base sequence represented by SEQ ID NO: 15 in which the base sequence ccatggct is added to its 5' end and the base sequence ggatcc is added to its 3' end is prepared. A base sequence represented by SEQ ID NO: 15 encodes an amino acid sequence represented by SEQ ID NO: 1.

The above double-stranded DNA (about 1.2 kb) thus prepared was double-digested with restriction enzymes NcoI and BamHI, and enzymatically digested DNA was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, an *E. coli* JM109 strain was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and BamHI, and then subjected to agarose gel electrophoresis. In each of six plasmids, DNA of about 1.2 kb was confirmed to be inserted into the above vector. Base sequences of the plasmids thus obtained were determined, and a plasmid having the target base sequence was designated as pTrc174.

Double-stranded DNA having a base sequence represented by SEQ ID NO: 16 in which the base sequence ccatggct is added to its 5' end side and the base sequence ggatcc is added to its 3' end side is prepared. A base sequence represented by SEQ ID NO: 16 encodes an amino acid sequence represented by SEQ ID NO: 3.

The above double-stranded DNA (about 1.2 kb) thus prepared was double-digested with restriction enzymes NcoI and BamHI, and enzymatically digested DNA was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, an *E. coli* JM109 strain was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and BamHI, and then subjected to agarose gel electrophoresis. In each of six plasmids, DNA of about 1.2 kb was confirmed to be inserted into the above vector. Base sequences of the plasmids thus obtained were determined, and a plasmid having the target base sequence was designated as pTrc204.

Double-stranded DNA having a base sequence represented by SEQ ID NO: 17 in which the base sequence ccatggct is added to its 5' end side and the base sequence ggatcc is added to its 3' end side is prepared. A base sequence represented by SEQ ID NO: 17 encodes an amino acid sequence represented by SEQ ID NO: 5.

The above double-stranded DNA (about 1.2 kb) thus prepared was double-digested with restriction enzymes NcoI and BamHI, and enzymatically digested DNA was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, an *E. coli* JM109 strain was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and BamHI, and then subjected to agarose gel electrophoresis. In each of six plasmids, the above DNA of about 1.2 kb was confirmed to be inserted into the above vector. Base sequences of the plasmids thus obtained were determined, and a plasmid having the target base sequence was designated as pTrc436.

Example 6 (Preparation of Recombinant Vector Containing a Polynucleotide Encoding Protein Having Ability to Convert Oxidized β-Nicotinamide Adenine Dinucleotide into its Reduced Form and Transformant Having the Vector)

Based on an amino acid sequence of a formate dehydrogenase derived from a *Bacillus* sp. F1(2010) strain mentioned in Journal of Applied Microbiology, 111 (2011) 1075-1085, a base sequence represented by SEQ ID NO: 26 is designed. A base sequence represented by SEQ ID NO: 26 encodes an amino acid sequence represented by SEQ ID NO: 43. Double-stranded DNA having a base sequence represented by SEQ ID NO: 26 in which the base sequence ccatggct is added to its 5' end side and the base sequence ggatcc is added to its 3' end side is prepared.

The above double-stranded DNA (about 1.2 kb) thus prepared was double-digested with restriction enzymes NcoI and BamHI, and enzymatically digested DNA was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, an *E. coli* JM109 strain was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and BamHI, and then subjected to agarose gel electrophoresis. In each of six plasmids, DNA of about 1.2 kb was confirmed to be inserted into the above vector. Base sequences of the plasmids thus obtained were determined, and a plasmid having the target base sequence was designated as pTrcFDH.

An *E. coli* JM109 strain was transformed using the plasmid pTrcFDH. The transformant thus obtained was inoculated into 20 ml of a sterilized LB medium containing 0.1 mM IPTG and 50 g/ml of ampicillin, and the medium was cultured by shaking at 30° C. for 15 hours. The culture solution thus obtained was centrifuged to obtain wet cells. About 0.7 g of the wet cells were suspended in 10 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 0.7 ml of centrifuged supernatant liquid.

Example 7 (Preparation of L-α-Amino Acid Compound Using Treated Product of Transformant of Present Invention)

An *E. coli* JM109 strain was transformed using the plasmid pTrc174. The transformant thus obtained was inoculated into 20 ml of a sterilized LB medium containing 0.1 mM IPTG and 50 µg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 10 mg of NAD+, 0.05 ml of the centrifuged supernatant liquid obtained in Example 6, 2.5 mg of ammonium formate, and 0.05 ml of the leucine dehydrogenase (A113G) purified enzyme solution obtained in Example 3 (36 g protein/l) were mixed, and the solution was shaken at 30° C. for 17.5 hours. This reaction solution was subjected to content analysis by liquid chromatography under the following condition. It was found that L-methionine was produced in a proportion of 5.6% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* JM109 strain was transformed using the plasmid pTrc204. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 1.0 mg of NAD4, 0.05 ml of the centrifuged supernatant liquid obtained in Example 6, 2.5 mg of ammonium formate, and 0.05 ml of the leucine dehydrogenase (A113G) purified enzyme solution obtained in Example 3 (36 g protein/l) were mixed, and the solution was shaken at 30° C. for 17.5 hours. This reaction solution was subjected to content analysis by liquid chromatography under the following condition. It was found that L-methionine was produced in a proportion of 30.2% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* JM109 strain was transformed using the plasmid pTrc436. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.4 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 10 mg of NAD+, 0.05 ml of the centrifuged supernatant liquid obtained in Example 6, 2.5 mg of ammonium formate, and 0.05 ml of the leucine dehydrogenase (A113G) purified enzyme solution obtained in Example 3 (36 g protein/l) were mixed, and the solution was shaken at 30° C. for 17.5 hours. This reaction solution was subjected to content analysis by liquid chromatography under the following condition. It was found that L-methionine was produced in a proportion of 1.2.1% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 8 (Preparation of Present Invented Polynucleotide (A), Present Invented Recombinant Vector, and Transformant of Present Invention)

Oligonucleotide primers each having a base sequence represented by any one of SEQ ID NO: 27 to 32 are synthesized.

TABLE 2

| Sense primer | Antisense primer |
|---|---|
| SEQ ID NO: 27<br>CCATATGTCTCGCCTGGACC<br>GCTGTCTGAG | SEQ ID NO: 28<br>GGATCCTTAAGCCGGGCTGG<br>CCGGACGG |
| SEQ ID NO: 29<br>CCATATGAACTCCAAGAAAC<br>TGCTGTCTATC | SEQ ID NO: 30<br>GGATCCTTACGGACGAGAAA<br>CGATAAAG |
| SEQ ID NO: 31<br>CCATATGACCTCTATTCTGC<br>CTTCTGTTAC | SEQ ID NO: 32<br>ACTCGAGGTCAGCCAGGGAT<br>TCACGCGCCAG |

Using an oligonucleotide primer having a base sequence represented by SEQ ID NO: 27 and an oligonucleotide primer having a base sequence represented by SEQ ID NO: 28, PCR was performed using the plasmid pTrc174 as a template and with the following reaction solution composition.
[Reaction Solution Composition]

| DNA solution of pTrc174: | 1.5 μl |
| dNTP (a mixture of 2 mM each): | 10 μl |
| Primer (50 pmol/μl): | 0.3 μl each |
| 2x buffer: | 25 μl |
| KOD-FX (1 U/μl, Toyobo): | 1 μl |
| Ultrapure water: | 11.9 μl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4'C.

Subsequently, a part of the above PCR reaction solution was subjected to agarose gel electrophoresis. A DNA band of about 1.2 kb was detected.

By adding restriction enzymes NdeI and BamHI to the remaining PCR reaction solution, DNA was double-digested, and enzymatically digested DNA of about 1.2 kb was purified.

Plasmid vector pET-15b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and BamHI, and then subjected to agarose gel electrophoresis. In each of six plasmids, DNA of about 1.2 kb was confirmed to be inserted into the above vector. The plasmids thus obtained are designed so that they can express a protein in which an amino acid sequence composed of 20 amino acids including consecutive 6 residues of histidine (SEQ ID NO: 44: MetGlySerSerHisHisHisHisHisHisSerSerGlyLeuValProArgGlySerHis) is added to the amino terminus of the present invented protein (A) encoded by the recombinant vector pTrc174. One of the plasmids thus obtained was designated as pET174SC.

Using an oligonucleotide primer having a base sequence represented by SEQ ID NO: 29 and an oligonucleotide primer having a base sequence represented by SEQ ID NO: 30, PCR was performed using the plasmid pTrc204 as a template and with the following reaction solution composition.

[Reaction Solution Composition]

| | |
|---|---|
| DNA solution of pTrc204: | 1.5 μl |
| dNTP (a mixture of 2 mM each): | 10 μl |
| Primer (50 pmol/μl): | 0.3 μl each |
| 2x buffer: | 25 μl |
| KOD-FX (1 U/μl, Toyobo): | 1 μl |
| Ultrapure water: | 11.9 μl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.2 kb was detected.

By adding restriction enzymes NdeI and BamHI to the remaining PCR reaction solution, DNA was double-digested, and enzymatically digested DNA of about 1.2 kb was purified.

Plasmid vector pET-15b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and BamHI, and then subjected to agarose gel electrophoresis. In each of six plasmids, DNA of about 1.2 kb was confirmed to be inserted into the above vector. The plasmids thus obtained are designed so that they can express a protein in which an amino acid sequence composed of 20 amino acids including consecutive 6 residues of histidine (SEQ ID NO: 44: MetGlySerSerHisHisHisHisHisHisSerSerGlyLeuValProArgGlySerHis) is added to the amino terminus of the present invented protein (A) encoded by the recombinant vector pTrc204. One of the plasmids thus obtained was designated as pET204SC.

Using an oligonucleotide primer having a base sequence represented by SEQ ID NO: 31 and an oligonucleotide primer having a base sequence represented by SEQ ID NO: 32, PCR was performed using the plasmid pTrc436 as a template and with the following reaction solution composition.

[Reaction Solution Composition]

| | |
|---|---|
| DNA solution of pTrc436: | 1.5 μl |
| dNTP (a mixture of 2 mM each): | 10 μl |
| Primer (50 pmol/μl): | 0.3 μl each |
| 2x buffer: | 25 μl |
| KOD-FX (1 U/μl, Toyobo): | 1 μl |
| Ultrapure water: | 11.9 μl |

A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.2 kb was detected.

By adding restriction enzymes NdeI and XhoI to the remaining PCR reaction solution, DNA was double-digested, and enzymatically digested DNA of about 1.2 kb was purified.

Plasmid vector pET-22b (manufactured by Novagen) was double-digested with restriction enzymes NdeI and XhoI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NcoI and XhoI, and then subjected to agarose gel electrophoresis. In each of six plasmids, DNA of about 1.2 kb was confirmed to be inserted into the above vector. The plasmids thus obtained are designed so that they can express a protein in which an amino acid sequence composed of 20 amino acids including consecutive 6 residues of histidine (SEQ ID NO: 44: MetGlySerSerHisHisHisHisHisHisSerSerGlyLeuValProArgGiySerHis) is added to the amino terminus of the present invented protein (A) encoded by the recombinant vector pTrc436. One of the plasmids thus obtained was designated as pET436SC.

Example 9 (Preparation of Recombinant Vector Containing Polynucleotide Encoding Protein Having Ability to Convert Hydrogen Peroxide into Molecular Oxygen and Transformant Having the Vector, and Preparation of the Protein)

(1) Preparation of Recombinant Vector Containing Polynucleotide Encoding Amino Acid Sequence of Protein Having Ability to Convert Hydrogen Peroxide into Molecular Oxygen, and Transformant Having the Vector An *E. coli* BL21(DE3) strain was cultured in 100 ml of a sterilized LB medium to obtain about 1.0 g of cells. From the cells, chromosomal DNA (hereinafter referred to as the chromosomal DNA (C)) was purified using the Qiagen Genomic Tip (manufactured by Qiagen) in accordance with the method mentioned in the manual attached thereto.

Based on a base sequence encoding a catalase derived from *E. coli* mentioned in Journal of Bacteriology, 170(9) (1988) 4415-4419, an oligonucleotide primer having a base sequence represented by SEQ ID NO: 33 (CCATATGAGCACGTCAGACGATATCCATAAC) and an oligonucleotide primer having a base sequence represented by SEQ ID NO: 34 (ACTCGAGCAGCAGGTCGAAACGGTCGAGGTTC) are synthesized.

Using an oligonucleotide primer having a base sequence represented by SEQ ID NO: 33 and an oligonucleotide primer having a base sequence represented by SEQ ID NO: 34, PCR was performed using the chromosomal DNA (C) as a template and with the following reaction solution composition using the Expand High Fidelity PCR System (Roche Diagnostics).

[Reaction Solution Composition]

| | |
|---|---|
| Chromosomal DNA (C) solution: | 1 μl |
| dNTP (a mixture of 2.5 mM each): | 1 μl |
| Primer (20 pmol/μl): | 0.4 μl each |
| 5x buffer (with MgCl$_2$): | 10 μl |
| enz.expandHiFi (3.5 × 10$^3$ U/ml): | 0.5 μl |
| Ultrapure water: | 33.7 μl |

A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 60° C. for 30 seconds, followed by 72° C. for 2 minutes was performed 10 times, and then an incubation cycle consisting of incubation at 94° C. for 15 seconds, followed by 65° C. for 30 seconds, followed by 72° C. for 2 minutes was performed 20 times, and further the solution was maintained at 72° C. for 7 minutes.

Subsequently, a part of the above PCR reaction solution was subjected to agarose gel electrophoresis. A DNA band of about 2.2 kb was detected.

By adding restriction enzymes NdeI and XhoI to the remaining PCR reaction solution, DNA was double-digested, and enzymatically digested DNA of about 2.2 kb was purified.

Plasmid vector pET-22b (manufactured by Novagen) was double-digested with restriction enzymes NdeI and XhoI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NdeI and XhoI, and then subjected to agarose gel electrophoresis. In each of six plasmids, DNA of about 2.2 kb was confirmed to be inserted into the above vector. The plasmids thus obtained are designed so that they can express a protein in which an amino acid sequence composed of 8 amino acids including consecutive 6 residues of histidine (SEQ ID NO: 45: LeuGluHisHisHisHisHisHis) is added to the carboxy terminus of the above catalase. One of the plasmids thus obtained was designated as pETcatE.

(2) Preparation of Protein Having Ability to Convert Hydrogen Peroxide into Molecular Oxygen An *E. coli* BL21(DE3) strain was transformed using the recombinant vector pETcatE. The transformant thus obtained was inoculated into 20 ml of a sterilized LB medium containing 0.1 mM IPTG and 50 μg/ml of ampicillin, and the medium was cultured by shaking at 37° C. for 15 hours. The culture solution thus obtained was centrifuged to obtain about 0.8 g of wet cells. About 0.8 g of the wet cells were suspended in 10 ml of 20 mM phosphate buffer (pH 7.4) containing 0.5 M NaCl and 5 mM imidazole (i.e., the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 7 ml of centrifuged supernatant liquid.

To about 7 ml of the centrifuged supernatant liquid thus obtained, 3 ml of the binding buffer was added to make about 10 ml, and then this liquid was applied to a HisTrap HP column (gel bed 1 ml) (manufactured by GE Healthcare Japan) with a flow rate of 1 ml/min. By passing about 5 ml of the binding buffer through this column with a flow rate of 1 ml/min, non-adsorbed proteins were eluted. Then, while maintaining the flow rate, by passing about 7 ml of 20 mM phosphate buffer (pH 7.4) containing 0.5 M NaCl and 29.75 mM imidazole through the column, non-adsorbed proteins and low adsorbed proteins were eluted. Next, adsorbed proteins were eluted by gradient elution in which the imidazole concentration was increased from 29.75 mM to 500 mM while 9.5 ml was passed through, and 5 ml of a fraction with the imidazole concentration of about 30 mM to 180 mM was collected. The fraction thus obtained was subjected to the Amicon Ultra-15 (manufactured by Merck Millipore), and desalting and concentration was performed and the buffer was replaced by 0.1 M Tris-HCl (pH 8) to obtain about 1 ml of a fraction. This fraction is hereinafter referred to as the catalase purified enzyme solution.

Example 10 (Preparation of α-Oxocarboxylic Acid Compound Using Treated Product of Transformant of Present Invention)

An *E. coli* BL21(DE3) strain was transformed using the plasmid pET174SC. The transformant thus obtained was inoculated into 20 ml of a sterilized LB medium containing 0.1 mM IPTG and 50 µg/ml of ampicillin, and the medium was cultured by shaking at 30° C. for 15 hours. The culture solution thus obtained was centrifuged to obtain wet cells. About 0.1 g of the wet cells were suspended in I ml of 0.1 M Tris-HCl buffer (pH 8.0), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), and 0.1 ml of 0.1 M Tris-HCl buffer (pH 8.0) were mixed, and the solution was shaken at 30° C. for 22 hours. This reaction solution was subjected to content analysis by liquid chromatography under the following condition. It was found that 2-oxo-4-(methylthio)butyric acid was produced in a proportion of 18.0% based on the amount of 2-hydroxy-4-(methylthio)butyric acid used for the reaction.
(Content Analysis Condition)
Column: UNISON UK-C18 (4.6 mmφ×25 cm, 3 µm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET204SC. The transformant thus obtained was inoculated into 20 ml of a sterilized LB medium containing 0.1 mM IPTG and 50 µg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), and 0.1 ml of 0.1 M Tris-HCl buffer (pH 8.0) were mixed, and the solution was shaken at 30° C. for 22 hours. This reaction solution was subjected to content analysis by liquid chromatography under the following condition. It was found that 2-oxo-4-(methylthio)butyric acid was produced in a proportion of 22.8% based on the amount of 2-hydroxy-4-(methylthio)butyric acid used for the reaction.
(Content Analysis Condition)
Column: UNISON UK-C18 (4.6 mmφ×25 cm, 3 µm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET436SC. The transformant thus obtained was inoculated into 20 ml of a sterilized LB medium containing 0.1 mM IPTG and 50 µg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), and 0.1 ml of 0.1 M Tris-HCl buffer (pH 8.0) were mixed, and the solution was shaken at 30° C. for 22 hours. This reaction solution was subjected to content analysis by liquid chromatography under the following condition. It was found that 2-oxo-4-(methylthio)butyric acid was produced in a proportion of 24.2% based on the amount of 2-hydroxy-4-(methylthio)butyric acid used for the reaction.
(Content Analysis Condition)
Column: UNISON UK-C18 (4.6 mmφ×25 cm, 3 µm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 11 (Preparation of Recombinant Vector Containing Polynucleotide Encoding Protein Having Ability to Convert Oxidized β-Nicotinamide Adenine Dinucleotide into its Reduced Form and Transformant Having the Vector, and Preparation of the Protein)

(1) Preparation of Recombinant Vector Containing Polynucleotide Encoding Protein Having Ability to Convert Oxidized β-Nicotinamide Adenine Dinucleotide into its Reduced Form and Transformant Having the Vector Based on an amino acid sequence of a formate dehydrogenase derived from a *Bacillus* sp. F1(2010) strain mentioned in Journal of Applied Microbiology 111 (2011) 1075-1085, a base sequence represented by SEQ ID NO: 26 is designed so that the frequency of use of codon is close to that in *E. coli*, and based on the base sequence, an oligonucleotide primer having a base sequence represented by SEQ ID NO: 35 (CCATATGGCTAAGATCGTTTGCGTTCTGTAC) and an oligonucleotide primer having a base sequence represented by SEQ ID NO: 36 (ACTCGAGAGCAGATTTCTTGAAACGTGCAG) are synthesized.

Using an oligonucleotide primer having a base sequence represented by SEQ ID NO: 35 and an oligonucleotide primer having a base sequence represented by SEQ ID NO: 36, PCR was performed using the recombinant vector pTrcFDH as a template and with the following reaction solution composition using the Expand High Fidelity PCR System (Roche Diagnostics).
[Reaction Solution Composition]

| DNA solution of pTrcFDH: | 1 µl |
| dNTP (a mixture of 2.5 mM each): | 1 µl |
| Primer (20 pmol/µl): | 0.4 µl each |
| 5x buffer (with MgCl$_2$): | 10 µl |
| enz.expandHiFi (3.5 × 10$^3$ U/ml): | 0.5 µl |
| Ultrapure water: | 33.7 µl |

A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.2 kb was detected.

By adding restriction enzymes NdeI and XhoI to the remaining PCR reaction solution, DNA was double-digested, and enzymatically digested DNA of about 1.2 kb was purified.

Plasmid vector pET-22b (manufactured by Novagen) was double-digested with restriction enzymes NdeI and XhoI, and an enzymatically digested vector DNA fragment was purified.

These purified DNAs were mixed and ligated with a T4 DNA ligase, and using the ligation solution thus obtained, *E. coli* DH5α was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with NdeI and XhoI, and then subjected to agarose gel electrophoresis. In each of six plasmids, DNA of about 1.2 kb was confirmed to be inserted into the above vector. The plasmids thus obtained are designed so that they can express a protein in which an amino acid sequence composed of 8 amino acids including consecutive 6 residues of histidine (SEQ ID NO: 45: LeuGluHisHisHisHisHisHis) is added to the carboxy terminus of the above formate dehydrogenase. One of the plasmids thus obtained was designated as pETFDH.

(2) Preparation of Protein Having Ability to Convert Oxidized β-Nicotinamide Adenine Dinucleotide into its Reduced Form An *E. coli* BL21(DE3) strain was transformed using the recombinant vector pETFDH. The transformant thus obtained was inoculated into 20 ml of a sterilized LB medium containing 0.1 mM IPTG and 50 µg/ml of ampicillin, and the medium was cultured by shaking at 37° C. for 15 hours. The culture solution thus obtained was centrifuged to obtain about 0.8 g of wet cells. About 0.8 g of the wet cells were suspended in 10 ml of 20 mM phosphate buffer (pH 7.4) containing 0.5 M NaCl and 5 mM imidazole (i.e., the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 7 ml of centrifuged supernatant liquid.

To about 7 ml of the centrifuged supernatant liquid thus obtained, 3 ml of the binding buffer was added to make about 10 ml, and then this liquid was applied to a HisTrap HP column (gel bed 1 ml) (manufactured by GE Healthcare Japan) with a flow rate of 1 ml/min. By passing about 5 ml of the binding buffer through this column with a flow rate of 1 ml/min, non-adsorbed proteins were eluted. Then, while maintaining the flow rate, by passing about 7 ml of 20 mM phosphate buffer (pH 7.4) containing 0.5 M NaCl and 29.75 mM imidazole through the column, non-adsorbed proteins and low adsorbed proteins were eluted. Next, adsorbed proteins were eluted by gradient elution in which the imidazole concentration was increased from 29.75 mM to 500 mM while 9.5 ml was passed through, and 4 ml of a fraction with the imidazole concentration of about 30 mM to 230 mM was collected. The fraction thus obtained was subjected to the Amicon Ultra-15 (manufactured by Merck Millipore), and desalting and concentration was performed and the buffer was replaced by 0.1 M Tris-HCl (pH 8) to obtain about 1 ml of a fraction. This fraction is hereinafter referred to as the formate dehydrogenase purified enzyme solution.

Example 12 (Preparation of L-α-Amino Acid Compound Using Treated Product of Transformant of Present Invention)

An *E. coli* BL21(DE3) strain was transformed using the plasmid pET174SC. The transformant thus obtained was inoculated into 20 ml of a sterilized LB medium containing 0.1 mM IPTG and 50 µg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), 0.05 ml of the formate dehydrogenase purified enzyme solution obtained in Example 11 (5.3 g protein/l), 10 mg of NAD+, 2.5 mg of ammonium formate, and 0.05 ml of the leucine dehydrogenase (A113G) purified enzyme solution obtained in Example 3 (36 g protein/l) were mixed, and the solution was shaken at 30° C. for 22 hours. This reaction solution was subjected to content analysis by liquid chromatography under the following condition. It was found that L-methionine was produced in a proportion of 12.0% based on the amount of 2-hydroxy-4-(methylthio)butyric acid used for the reaction.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET204SC. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), 0.05 ml of the formate dehydrogenase purified enzyme solution obtained in Example 11 (5.3 g protein/l), 10 mg of NAD+, 2.5 mg of ammonium formate, and 0.05 ml of the leucine dehydrogenase (A113G) purified enzyme solution obtained in Example 3 (36 g protein/l) were mixed, and the solution was shaken at 30° C. for 22 hours. This reaction solution was subjected to content analysis by liquid chromatography under the following condition. It was found that L-methionine was produced in a proportion of 7.7% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm An *E. coli* BL21(DE3) strain was transformed using the plasmid pET436SC. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH was adjusted to 9 with ammonia water, 0.05 ml of the catalase purified enzyme solution obtained in Example 9 (3.3 g protein/l), 0.05 ml of the formate dehydrogenase purified enzyme solution obtained in Example 11 (5.3 g protein/l), 10 mg of NAD+, 2.5 mg of ammonium formate, and 0.05 ml of the leucine dehydrogenase (A113G) purified enzyme solution obtained in Example 3 (36 g protein/l) were mixed, and the solution was shaken at 30° C. for 22 hours. This reaction solution was subjected to content analysis by liquid chromatography under the following condition. It was found that L-methionine was produced in a proportion of 33.9% based on the amount of 2-hydroxy-4-(methylthio)butyric acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 13 (Preparation of Present Invented Recombinant Vector)

(1) Preparation of Polynucleotide Encoding Present Protein (B)

With reference to a sequence near the Shine-Dalgarno sequence of pTrc99A (manufactured by GE Healthcare Japan), an oligonucleotide primer having a base sequence represented by SEQ ID NO: 37 (CGGATCCGAGGAAACAGACCATGG) is synthesized. Based on a sequence of a leucine dehydrogenase derived from a *Bacillus sphaericus* IF O3525 strain mentioned in Journal of Molecular Catalysis B: Enzymatic, 23 (2003) 239-247, an oligonucleotide primer having a base sequence represented by SEQ ID NO: 38 (ctcagagTTAACGGCCGTTCAAAATATT) is synthesized.

Using an oligonucleotide primer having a base sequence represented by SEQ ID NO: 37 and an oligonucleotide primer having a base sequence represented by SEQ ID NO: 38, PCR is performed using the recombinant vector pTrcLD (A113G) mentioned in Example 3 (2) as a template and with the following reaction solution composition using the Expand High Fidelity PCR System (manufactured by Roche Diagnostics). (0159)
[Reaction Solution Composition]

| | |
|---|---|
| Plasmid pTrcLD solution: | 1 μl |
| dNTP (a mixtuxe of 2.5 mM each): | 1 μl |
| Primer (20 pmol/μl): | 0.4 μl each |
| 5x buffer (with MgCl$_2$): | 10 μl |
| enz.expandHiFi (3.5 × 10$^3$ U/ml): | 0.5 μl |
| Ultrapure water: | 36.7 μl |

A container containing a reaction solution with the above composition is set in a thermal cycler (PERKIN ELMER-GeneAmp PCR System 2400) and incubated at 94° C. for 2 minutes, and an incubation cycle consisting of incubation at 94° C. for 20 seconds, followed by 55° C. for 30 seconds, followed by 72° C. for 1.5 minutes is performed 25 times, and further the solution is maintained at 72° C. for 7 minutes.

Subsequently, a part of the above PCR reaction solution is subjected to agarose gel electrophoresis. A DNA band of about 1.1 kb is detected.

By adding restriction enzymes BamHI and XbaI to the remaining PCR reaction solution, DNA was double-digested, and enzymatically digested DNA of about 1.1 kb was purified.

(2) Preparation of Present Invented Vector

The recombinant vector pTrc174 mentioned in Example 5 is double-digested with restriction enzymes BamHI and XbaI, and enzymatically digested DNA is purified.

The DNA thus obtained and the DNA of about 1.1 kbp purified in the above (1) are mixed and ligated with a T4 DNA ligase, and using the ligation solution thus obtained, an *E. coli* DH5α is transformed.

The transformant thus obtained is cultured in an LB agar medium containing 50 μg/ml of ampicillin, colonies are randomly selected from the growing colonies. Each of the selected colonies is inoculated into 2 ml of a sterilized LB medium containing 50 μg/ml of ampicillin, and the medium is cultured by shaking in a test tube at 37° C. for 17 hours. Plasmids are removed from each cultured cell using the QIAprep Spin Miniprep Kit (manufactured by Qiagen). A part of each of the removed plasmids is double-digested with BamHI and XbaI, and then subjected to agarose gel electrophoresis. Confirm that DNA of about 1.1 kb is inserted into the plasmid thus obtained. The plasmid thus obtained is hereinafter referred to as pTrc174LD(A113G).

The recombinant vector pTrc204 mentioned in Example 5 is double-digested with restriction enzymes BamHI and XbaI, and enzymatically digested DNA is purified.

The DNA thus obtained and the DNA of about 1.1 kbp purified in the above (1) are mixed and ligated with a T4 DNA ligase, and using the ligation solution thus obtained, an *E. coli* DH5α is transformed.

The transformant thus obtained is cultured in an LB agar medium containing 50 μg/ml of ampicillin, colonies are randomly selected from the growing colonies. Each of the selected colonies is inoculated into 2 ml of a sterilized LB medium containing 50 μg/ml of ampicillin, and the medium is cultured by shaking in a test tube at 37° C. for 17 hours. Plasmids are removed from each cultured cell using the QIAprep Spin Miniprep Kit (manufactured by Qiagen). A part of each of the removed plasmids is double-digested with BamHI and XbaI, and then subjected to electrophoresis. Confirm that DNA of about 1.1 kb is inserted into the plasmid thus obtained. The plasmid thus obtained is hereinafter referred to as pTrc204LD(A113G).

The recombinant vector pTrc436 mentioned in Example 5 is double-digested with restriction enzymes BamHI and XbaI, and enzymatically digested DNA is purified.

The DNA thus obtained and the DNA of about 1.1 kbp purified in the above (1) are mixed and ligated with a T4 DNA ligase, and using the ligation solution thus obtained, an *E. coli* DH5α is transformed.

The transformant thus obtained is cultured in an LB agar medium containing 50 μg/ml of ampicillin, colonies are randomly selected from the growing colonies. Each of the selected colonies is inoculated into 2 ml of a sterilized LB medium containing 50 μg/ml of ampicillin, and the medium is cultured by shaking in a test tube at 37° C. for 17 hours. Plasmids are removed from each cultured cell using the QIAprep Spin Miniprep Kit (manufactured by Qiagen). A part of each of the removed plasmids is double-digested with BamHI and XbaI, and then subjected to electrophoresis. Confirm that DNA of about 1.1 kb is inserted into the plasmid thus obtained. The plasmid thus obtained is hereinafter referred to as pTrc436LD(A113G).

Example 14 (Preparation of L-α-Amino Acid Compound Using Treated Product of a Transformant of Present Invention)

An *E. coli* JM109 strain is transformed using the plasmid pTrc174LD(A113G) mentioned in (2) of Example 13. The transformant thus obtained is inoculated into 20 ml of a sterilized LB medium containing 0.1 mM IPTG and 50 μg/ml of ampicillin, and the medium is cultured by shaking at 30° C. for 15 hours. The culture solution thus obtained is centrifuged to obtain wet cells. About 0.1 g of the wet cells are suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained is centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH is adjusted to 9 with ammonia water, 0.05 ml of the catalase purified enzyme solution mentioned in Example 9 (3.3 g protein/l), 0.05 ml of the formate dehydrogenase purified enzyme solution mentioned in Example 11 (5.3 g protein/l), 10 mg of NAD+, and 2.5 mg of ammonium formate are mixed, and the solution is shaken at 30° C. for 22 hours. This reaction solution is subjected to content analysis by liquid chromatography under the following condition. The yield of L-methionine based on the amount of 2-hydroxy-4-(methylthio)butyric acid used for the reaction is confirmed.

(Content Analysis Condition)

Column: UNISON UK-C18 (4.6 mmφ×25 cm, 3 μm)

Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10

Flow rate: 0.8 ml/min

Column temperature: 37° C.

Detection: 210 nm

An *E. coli* JM109 strain is transformed using the plasmid pTrc204LD(A113G) mentioned in (2) of Example 13. The transformant thus obtained is inoculated into 20 ml of a sterilized LB medium containing 0.1 mM IPTG and 50 μg/ml of ampicillin, and the medium is cultured by shaking at 30° C. for 15 hours. The culture solution thus obtained is centrifuged to obtain wet cells. About 0.1 g of the wet cells are suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained is centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH is adjusted to 9 with ammonia water, 0.05 ml of the catalase purified enzyme solution mentioned in Example 9 (3.3 g protein/l), 0.05 ml of the formate dehydrogenase purified enzyme solution mentioned in Example 11 (5.3 g protein/l), 10 mg of NAD+, and 2.5 mg of ammonium formate are mixed, and the solution is shaken at 30° C. for 22 hours. This reaction solution is subjected to content analysis by liquid chromatography under the following condition. The yield of L-methionine based on the amount of 2-hydroxy-4-(methylthio)butyric acid used for the reaction is confirmed.

(Content Analysis Condition)

Column: UNISON UK-C18 (4.6 mmφ×25 cm, 3 mm)

Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10

Flow rate: 0.8 ml/min
Column temperature: 37° C.
Detection: 210 nm

An *E. coli* JM109 strain is transformed using the plasmid pTrc436LD(A113G) mentioned in (2) of Example 13. The transformant thus obtained is inoculated into 20 ml of a sterilized LB medium containing 0.1 mM IPTG and 50 μg/ml of ampicillin, and the medium is cultured by shaking at 30° C. for 15 hours. The culture solution thus obtained is centrifuged to obtain wet cells. About 0.1 g of the wet cells are suspended in 1 ml of 0.1 M Tris-HCl buffer (pH 8.0), and disrupted at 2,500 rpm for 20 minutes using the Multi-beads shocker (manufactured by Yasui Kikai Corporation) and glass beads (0.1 mmΦ). The disruption liquid thus obtained is centrifuged at 8,000 rpm and 4° C. for 10 minutes to obtain about 0.7 ml of centrifuged supernatant liquid. With 0.35 ml of the centrifuged supernatant liquid thus obtained, 0.02 ml of a 40% aqueous solution of 2-hydroxy-4-(methylthio)butyric acid (manufactured by Tokyo Chemical Industry) whose pH is adjusted to 9 with ammonia water, 0.05 ml of the catalase purified enzyme solution mentioned in Example 9 (3.3 g protein/l), 0.05 ml of the formate dehydrogenase purified enzyme solution mentioned in Example 11 (5.3 g protein/l), 10 mg of NAD+, and 2.5 mg of ammonium formate are mixed, and the solution is shaken at 30° C. for 22 hours. This reaction solution is subjected to content analysis by liquid chromatography under the following condition. The yield of L-methionine based on the amount of 2-hydroxy-4-(methylthio)butyric acid used for the reaction is confirmed.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm

INDUSTRIAL APPLICABILITY

According to the present invention, it is possible to provide an oxidase, a polynucleotide encoding the same, a method for producing an α-amino acid compound such as methionine using these, and the like.

[Sequence Listing Free Text]
SEQ ID NO: 9-14
    An oligonucleotide primer designed for PCR
SEQ ID NO: 15-17
    A polynucleotide encoding an oxidase
SEQ ID NO: 18-38
    An oligonucleotide primer designed for PCR
SEQ ID NO: 44-45
    An amino acid sequence designed

The invention claimed is:

1. A method for producing a sulfur containing L-α-amino acid compound of formula (3):

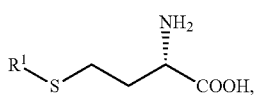

wherein the method comprises:

(I) a step of reacting a protein with a sulfur-containing α-hydroxycarboxylic acid compound of formula (1) to obtain the corresponding sulfur-containing α-oxocarboxylic acid compound of formula (2):

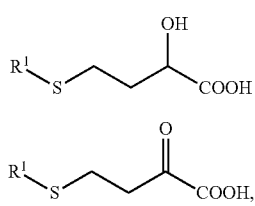

wherein the protein is selected from the group consisting of:

(A1) a protein having the amino acid sequence of SEQ ID NO: 5, (A2) a protein having an amino acid sequence having at least 95% sequence identity to the amino acid sequence of SEQ ID NO: 5, wherein the protein has the ability to oxidize and convert the sulfur-containing α-hydroxycarboxylic acid compound of formula (1) into the corresponding sulfur-containing α-oxocarboxylic acid compound of formula (2), and (A3) a protein having the amino acid sequence of SEQ ID NO: 5 in which 1 to 10 amino acids are deleted, substituted, or added, wherein the protein has the ability to oxidize and convert the sulfur-containing α-hydroxycarboxylic acid compound of formula (1) into the corresponding sulfur-containing α-oxocarboxylic acid compound of formula (2); and (II) a step of reacting the sulfur-containing α-oxocarboxylic acid compound of formula (2) obtained in the step (I) with a protein having the ability to aminate and convert the sulfur-containing α-oxocarboxylic acid compound of formula (2) into the corresponding sulfur-containing L-α-amino acid compound of formula (3) to thereby obtain the sulfur-containing L-α-amino acid compound of formula (3), wherein the protein is selected from the group consisting of:

(B1) a protein having the amino acid sequence of SEQ ID NO: 7, (B2) a protein having an amino acid sequence having at least 90% sequence identity to the amino acid sequence of SEQ ID NO: 7, wherein the protein has the ability to aminate and convert the sulfur-containing α-oxocarboxylic acid compound of formula (2) into the corresponding sulfur-containing L-α-amino acid compound of formula (3), and (B3) a protein having the amino acid sequence of SEQ ID NO: 7 in which 1 to 36 amino acids are deleted, substituted, or added, wherein the protein has the ability to aminate and convert the sulfur-containing α-oxocarboxylic acid compound of formula (2) into the corresponding sulfur-containing L-α-amino acid compound of formula (3), wherein $R^1$ in formula (1), formula (2), and formula (3) is a $C_1$-$C_8$ alkyl group.

2. The production method according to claim 1, wherein the protein in step (II) having the ability to aminate and convert the sulfur-containing α-oxocarboxylic acid compound of formula (2) into the corresponding sulfur-containing L-α-amino acid compound of formula (3) is a leucine dehydrogenase.

3. The production method according to claim 2, wherein the leucine dehydrogenase is a leucine dehydrogenase derived from *Bacillus sphaericus*.

4. The production method according to claim 1, wherein the protein having any one of the amino acid sequences (A1), (A2), or (A3) is provided as a transformant, a freeze-dried transformant, an organic solvent-treated transformant, a dried transformant, a triturated transformant, an autolysate of a transformant, a sonicate of a transformant, a transformant extract, or an alkali-treated product of a transformant, wherein the transformant is a host cell comprising a polynucleotide encoding the protein.

5. The production method according to claim 4, wherein the polynucleotide is comprised in a recombinant vector.

6. The production method according to claim 1, wherein the protein having any one of the amino acid sequences (B1), (B2), or (B3) is provided as a transformant, a freeze-dried transformant, an organic solvent-treated transformant, a dried transformant, a triturated transformant, an autolys ate of a transformant, a sonic ate of a transformant, a transformant extract, or an alkali-treated product of a transformant, wherein the transformant is a host cell comprising a polynucleotide encoding the protein.

7. The production method according to claim 6, wherein the polynucleotide is comprised in a recombinant vector.

8. The production method according to claim 1, wherein step (I) is performed in the presence of a protein having the ability to convert hydrogen peroxide into molecular oxygen.

9. The production method according to claim 8, wherein the protein having the ability to convert hydrogen peroxide into molecular oxygen is a catalase.

10. The production method according to claim 8, wherein the protein having the ability to convert hydrogen peroxide into molecular oxygen is provided as a transformant a freeze-dried transformant, an organic solvent-treated transformant, a dried transformant, a triturated transformant, an autolysate of a transformant, a sonicate of a transformant, a transformant extract, or an alkali-treated product of a transformant, wherein the transformant is a host cell comprising a polynucleotide encoding the protein.

11. The production method according to claim 1, wherein step (II) is performed in the presence of a protein having the ability to convert an oxidized β-nicotinamide adenine dinucleotide or an oxidized β-nicotinamide adenine dinucleotide phosphate into its reduced form.

12. The production method according to claim 11, wherein the protein having the ability to convert an oxidized β-nicotinamide adenine dinucleotide or an oxidized β-nicotinamide adenine dinucleotide phosphate into its reduced form is a formate dehydrogenase.

13. The production method according to claim 11, wherein the protein having the ability to convert an oxidized β-nicotinamide adenine dinucleotide or an oxidized β-nicotinamide adenine dinucleotide phosphate into its reduced form is provided as a transformant, a freeze-dried transformant, an organic solvent-treated transformant, a dried transformant, a triturated transformant, an autolysate of a transformant, a sonicate of a transformant, a transformant extract, or an alkali-treated product of a transformant, wherein the transformant is a host cell comprising a polynucleotide encoding the protein.

14. The production method according to claim 1, wherein step (I) and step (II) are performed in a single reaction system.

15. The production method according to claim 1, wherein the sulfur containing L-α-amino acid compound of formula (3) is L-methionine.

\* \* \* \* \*

```
                        SEQUENCE LISTING

<160> NUMBER OF SEQ ID NOS: 45

<210> SEQ ID NO 1
<211> LENGTH: 391
<212> TYPE: PRT
<213> ORGANISM: Achromobacter denitrificans

<400> SEQUENCE: 1

Met Ser Arg Leu Asp Arg Cys Leu Ser Val Arg Asp Phe Glu Arg Glu
1               5                  10                  15

Ala Arg Arg Ile Met Pro Arg Cys Val Glu Gly Tyr Val Cys Gly Gly
                20                  25                  30

Thr Glu Asp Gly Ala Ser Leu Ala Glu Ser Val Arg Ala Leu Gly Asp
            35                  40                  45

Val Gly Phe Arg Pro Arg Gly Leu Arg Val Val Asp Gln Arg Asn Ser
        50                  55                  60

Lys Val Glu Leu Tyr Gly Gln Thr Tyr Ala Met Pro Val Gly Phe Ala
65                  70                  75                  80

Pro Thr Gly Phe Ser Ala Ile Val Met His Glu Cys Asp Leu Ala Leu
                85                  90                  95

Ala Gln Ala Ala Gln His Ala Glu Ile Pro Phe Ile Ile Ser Gly Ala
                100                 105                 110

Ser Ser Val Pro Leu Glu Arg Leu Gln Gln Ala Thr Gly Lys Arg Cys
            115                 120                 125

Trp Tyr Gln Ala Tyr Leu Pro Gly Asn Thr Glu Arg Ile Gly Arg Leu
        130                 135                 140

Leu Gly Arg Leu Arg Gln Ala Glu Ile Pro Val Leu Val Val Thr Ile
145                 150                 155                 160

Asp Thr Cys Val Gly Ala Asn Arg Glu Asn Leu Gln Arg Leu Ala Phe
                165                 170                 175
```

```
Thr Val Pro Phe Lys Met Ser Ala Ser Val Val Leu Asp Gly Leu Arg
            180                 185                 190

His Pro Arg Trp Ser Leu Asn Val Phe Met Arg Thr Leu Leu Gly Ser
        195                 200                 205

Gly Val Pro Arg Phe Ser Asn Leu Cys Glu Glu Ile Gly Pro Pro Ile
    210                 215                 220

Thr Gln Asp Pro Pro Asn Gly Phe Arg Gly Glu Arg Asp Lys Leu Ser
225                 230                 235                 240

Trp Glu His Ile Arg Trp Ile Arg Glu Asn Trp Pro Gly Lys Leu Val
                245                 250                 255

Leu Lys Gly Val Met His Pro Asp Asp Ala Arg Gln Ala Cys Val Ala
            260                 265                 270

Gly Ala Asp Gly Val Ile Val Ser Asn His Gly Gly Arg Gln Leu Asp
        275                 280                 285

Gly Cys Ile Ser Pro Leu Gln Ala Leu Pro Glu Ile Val Ala Ala Val
    290                 295                 300

Pro Pro Gly Phe Pro Val Met Val Asp Gly Gly Phe Arg Arg Gly Ser
305                 310                 315                 320

Asp Val Leu Lys Ala Val Ala Leu Gly Ala Arg Met Val Phe Thr Gly
                325                 330                 335

Arg Pro Gln Leu Phe Gly Ala Ala Val Gly Gly Gln Ala Gly Ile Arg
            340                 345                 350

Lys Val Ala Ala Ile Phe Arg Ser Glu Ile Ser Thr Asp Leu Ala Leu
        355                 360                 365

Leu Gly Cys Ser Ser Leu Ala Asp Val Thr Pro Asp Leu Ile Ala Pro
    370                 375                 380

Ile Arg Pro Ala Ser Pro Ala
385                 390

<210> SEQ ID NO 2
<211> LENGTH: 1173
<212> TYPE: DNA
<213> ORGANISM: Achromobacter denitrificans

<400> SEQUENCE: 2
atgagccggc tggaccgctg cctgtcggtg cgcgacttcg agcgcgaggc gcggcgcatc      60
atgccgcgct gcgtcgaagg ctacgtctgc ggcggcaccg aggacggcgc ttcgctggcc     120
gagtcggtgc gcgccctggg cgacgtcggg ttccggccgc gggggctgcg cgtagtggac     180
cagcgcaaca gcaaggtcga actctacggc cagacctacg ccatgccggt gggtttcgcg     240
cccaccggat tctccgccat cgtcatgcac gagtgcgacc tggcgctggc gcaggccgcg     300
cagcacgccg agattccgtt catcatcagc ggcgcttcca gcgtgccgct ggaacgcctg     360
cagcaggcca cgggcaagcg ctgctggtac caggcctatc tgccgggcaa caccgaacgc     420
atcggcaggc tgttgggccg cctgcgccag gccgagatcc cggtgctggt ggtcaccatc     480
gacacctgcg taggcgcgaa ccgcgagaac ctgcagcgcc tggccttcac cgtgccttc      540 aagatgagcg ccagcgtggt actcgacggc ctgcggcatc cgcgctggag cctgaacgtc     600
ttcatgcgca cgctgctggg cagcggcgtg ccgcgcttct cgaatctttg cgaggagatc     660
ggcccgccca tcacgcagga cccacccaac ggctttcgcg gcgaacgcga caagctgtcg     720
tgggagcaca tccgctggat cgcgagaac tggccgggca agctggtgct caagggcgtg     780
atgcatcccg acgacgcgcg ccaggcctgc gtggccggcg ccgacggcgt catcgtctcc     840
aaccacggcg gccgccagct ggacggctgc atttcgccgc tgcaggcgct gcccgagatc     900
```

```
gtggcggcgg tgccgcccgg atttccggtc atggtcgacg gcggattccg ccgcggctcg    960
gacgtgctca aggcggtggc cctgggcgcg cgcatggtgt tcaccggcag gccgcagctt   1020
ttcggggcgg cggtcggcgg ccaggccggc atccgcaagg tggccgcgat tttccgcagc   1080
gaaatctcga ccgacctggc gctgctgggc tgcagcagcc tggccgacgt cacgccggat   1140
ctgatcgcgc cgatacggcc ggccagcccg gca                                1173
```

<210> SEQ ID NO 3
<211> LENGTH: 386
<212> TYPE: PRT
<213> ORGANISM: Achromobacter denitrificans

<400> SEQUENCE: 3

```
Met Asn Ser Lys Lys Leu Leu Ser Ile Gly Asp Tyr Glu Arg Ala Ala
1               5                   10                  15

Lys Ala Val Leu Pro His Ala Val Phe Gly Tyr Val Asn Gly Gly Thr
            20                  25                  30

Glu Asp Cys Leu Thr Leu Gln Ala Asn Arg Glu Ala Phe Arg Ser Val
        35                  40                  45

Gln Phe Arg Pro Arg Gly Leu Val Gly Val Ala Gln Arg Thr Gln Ala
    50                  55                  60

Val Glu Leu Trp Gly Arg Gln Tyr Arg His Pro Phe Gly Ile Ala Pro
65                  70                  75                  80

Met Gly Met Thr Ala Met Cys Arg His Arg Cys Glu Trp Asp Leu Ala
                85                  90                  95

Lys Ala Ala Ser Glu Ala Lys Ile Pro Phe Val Leu Ser Gly Leu Ser
            100                 105                 110

Thr Leu Ala Met Glu Thr Val Arg Gln Ala Asp Ala Asp Phe Trp Tyr
        115                 120                 125

Gln Gly Tyr Ile Pro Gly Asp Lys Asp Val Ile Glu Pro Leu Leu Arg
    130                 135                 140

Arg Leu Arg Ala Asn Glu Val Asp Val Leu Val Thr Ile Asp Thr
145                 150                 155                 160

Pro Val Gly Ala Asn Arg Glu Asn Asn Gln Arg Asn Gly Phe Thr Ile
                165                 170                 175

Pro Phe Lys Phe Ser Gly Gly Leu Leu Trp Asp Gly Leu Arg His Pro
            180                 185                 190

Arg Trp Ser Ala Asn Val Phe Leu Arg Thr Leu Leu Ser Asp Arg Gln
        195                 200                 205

Val Pro Arg Phe Cys Asn Val Val Ala Asp Thr Arg Gly Tyr Arg Ile
    210                 215                 220

Thr Glu Glu Pro Lys Gly Gly Leu Arg Gly Gly Arg Asp Arg Leu Asp
225                 230                 235                 240

Trp Ser His Leu Ala Trp Met Arg Asp Ile Trp Pro Gly Arg Ile Val
                245                 250                 255

Leu Lys Gly Val Ala His Pro Gly Asp Ala Gln Leu Ala Glu Gln Met
            260                 265                 270

Gly Leu Asp Gly Val Ile Val Ser Asn His Gly Gly Arg Gln Leu Asp
        275                 280                 285

Gly Ala Gln Gly Ala Leu Asp Ala Leu Pro Glu Val Val Ala Ala Val
    290                 295                 300

Gly Pro Asn Phe Pro Val Met Val Asp Gly Gly Phe Arg Arg Gly Ala
305                 310                 315                 320
```

```
Asp Val Leu Lys Ala Ile Ala Leu Gly Ala Arg Met Val Phe Leu Gly
                325                 330                 335

Arg Pro Phe Leu Tyr Gly Ala Ser Val Ala Gly Gln Ala Gly Val Ala
            340                 345                 350

Arg Ile Ile Asp Ile Leu Gly Thr Glu Ile Asp Arg Asn Leu Gly Leu
        355                 360                 365

Leu Gly Cys Arg Asp Leu Ala Glu Leu Gly Ser Asp Phe Ile Val Ser
    370                 375                 380

Arg Pro
385

<210> SEQ ID NO 4
<211> LENGTH: 1158
<212> TYPE: DNA
<213> ORGANISM: Achromobacter denitrificans

<400> SEQUENCE: 4
atgaactcaa agaaactctt gtcgataggc gactacgagc gcgcggccaa ggcggtcctg      60
ccgcacgcgg tgttcggcta cgtcaacggc ggcaccgaag actgtctgac gctgcaagcc     120
aaccgcgagg cgttccgttc ggtccagttc gtccgcgcg gcctggtcgg cgtcgcgcag      180
cgcacgcagg ccgtggaact ctggggaagg caataccggc atcctttcgg gatcgcgccc     240
atgggcatga ccgccatgtg ccgccaccgc tgcgaatggg acctggccaa ggccgcgtca     300
gaggcgaaaa ttccgttcgt gctcagcggc cttttccacgc tggccatgga aaccgtgcgc    360
caggccgatg ccgatttctg gtaccagggc tacatccccg cgacaaggga cgtcatcgaa    420
ccgctgctgc ggcgcctgcg ggccaacgag gtcgacgtgc tggtcgtcac catcgacacg    480
cccgtgggcg cgaaccgcga gaacaaccag cgcaacggct tcaccattcc gttcaagttc    540
agcggcggcc tgctctggga cgggctgcgt catccccgct ggtccgccaa cgtgtttctc    600 cgcacccttgc tttcggaccg gcaggtgccg cgcttctgca acgtggtcgc cgatacgcgc   660
ggctaccgca tcaccgaaga acccaagggc ggcctgcgcg gcggccgcga ccggctggac    720
tggtcgcacc tggcctggat gcgcgacatc tggccgggcc gcatcgtcct caagggcgtc    780
gcccatcccg gcgacgcgca gctggcggaa caaatgggcc tggacggcgt catcgtctcc    840
aaccacggcg gacgccagct cgacggcgcg cagggcgccc tggacgcctt gcccgaggtc    900
gtcgccgcgg tgggcccgaa tttccggtgg atggtcgacg gcggttttcg ccgcggcgcc    960
gacgtcctca aggccatcgc gctgggcgcg cgcatggtgt tcctgggccg ccccttctc   1020 tacgcgcgcg ccgtggccgg acaggccggc gtggcgcgca tcatcgacat tttgggaacc  1080
gaaatcgacc gcaacctggg gttgcttggg tgccgcgacc tggcggagct gggaagcgac  1140
ttcatcgtgt cgcgccct                                                1158

<210> SEQ ID NO 5
<211> LENGTH: 409
<212> TYPE: PRT
<213> ORGANISM: Achromobacter denitrificans

<400> SEQUENCE: 5

Met Thr Ser Ile Leu Pro Ser Val Thr Val Pro Gly Ser Ser Pro Ala
1               5                   10                  15

Glu Ala Ser Arg Pro Leu Pro Arg Ala Leu Gln Arg Met Leu Ser Leu
            20                  25                  30

Asp Asp Phe Glu Ala Ala Ala Arg Arg Arg Leu Pro Arg Pro Ile Phe
        35                  40                  45
```

Gly Tyr Ile Ala Gly Ala Ala Glu Asp Asn Gln Ser Leu Arg Ser Asn
            50                  55                  60

Arg Glu Ala Phe Gly Arg Tyr Ala Phe Ala Pro Arg Val Leu Val Asp
 65                  70                  75                  80

Val Ser Arg Arg Ser Gln Gln Thr Glu Leu Phe Gly Arg Arg Tyr Ala
                 85                  90                  95

Ser Pro Phe Gly Ile Ala Pro Met Gly Ile Ser Ala Leu Ser Thr Tyr
                100                 105                 110

Arg Gly Asp Ile Val Leu Ala Arg Ala Arg Glu Gln Gly Ile Pro
            115                 120                 125

Ala Ile Leu Ser Gly Thr Ser Leu Ile Pro Leu Glu Asp Val Ile Arg
130                 135                 140

Glu Ala Pro Gly Thr Trp Phe Gln Ala Tyr Leu Pro Gly Asp Pro Gln
145                 150                 155                 160

Arg Ile Asp Ala Leu Val Glu Arg Ala Arg Arg Ala Gly Phe Glu Thr
                165                 170                 175

Leu Val Leu Thr Val Asp Ile Pro Val Ser Ala Asn Arg Glu Asn Asn
                180                 185                 190

Val Arg Thr Gly Phe Ser Thr Pro Leu Lys Pro Ser Leu Arg Leu Ala
                195                 200                 205

Trp Asp Gly Val Thr Arg Pro Arg Trp Leu Ala Gly Thr Phe Leu Arg
210                 215                 220

Thr Leu Leu Lys His Gly Met Pro His Phe Glu Asn Ser Phe Ala Thr
225                 230                 235                 240

Arg Gly Ala Pro Ile Val Ser Ala Ser Val Leu Arg Asp Phe Ser Ala
                245                 250                 255

Arg Asp His Leu Asn Trp Glu His Val Ala Arg Ile Arg Arg Gln Trp
                260                 265                 270

Pro Gly Ala Leu Ile Ile Lys Gly Ile Leu His Pro Gln Asp Ala Ala
            275                 280                 285

Leu Ala Arg Ser His Gly Ala Asp Gly Val Ile Val Ser Asn His Gly
290                 295                 300

Gly Arg Gln Leu Asp Gly Ala Ile Ser Pro Leu Arg Ala Leu Pro Gly
305                 310                 315                 320

Val Val Ala Ala Ala Gly Asp Met Thr Val Met Met Asp Ser Gly Ile
                325                 330                 335

Arg Arg Gly Ser Asp Val Leu Lys Ala Leu Ala Leu Gly Ala Arg His
                340                 345                 350

Val Phe Val Gly Arg Pro Phe Asn Tyr Ala Ala Val Gly Gly Glu
            355                 360                 365

Ala Gly Val Ala His Ala Ile Gly Leu Leu Arg Ala Glu Ile Asp Arg
370                 375                 380

Asn Met Ala Met Leu Gly Ile Asn Thr Leu Arg Glu Met Asp Ala Gly
385                 390                 395                 400

Leu Leu Ala Arg Glu Ser Leu Ala Asp
                405

<210> SEQ ID NO 6
<211> LENGTH: 1227
<212> TYPE: DNA
<213> ORGANISM: Achromobacter denitrificans

<400> SEQUENCE: 6
atgacatcca tccttccgtc cgtcaccgtt cccggcagca gccccgccga ggcctcgcgg      60

```
ccgctgccgc gcgcgctgca acgcatgctg tcgctggatg atttcgaggc cgccgcgcgc    120
cgccgcctgc cgcgcccgat cttcggctac atcgccggcg cggccgaaga caaccagtcg    180
ctgcgcagca accgcgaggc cttcggccgc tacgcgttcg cgccccgcgt gctggtggac    240
gtgtcgcgcc gcagccagca gaccgaactg ttcggacgcc gctacgcctc gcccttcggc    300
atcgcgccga tgggcatcag cgcgctgtcg acctaccgcg gcgacatcgt gctggcgcgc    360
gccgcccgcg agcaaggcat cccggccatc ctcagcggga cttcgctgat tccgctggaa    420
gacgtgatcc gcgaagcgcc cggcacctgg ttccaggcct atctgccggg cgatccgcag    480
cgcatcgacg cgctggtcga acgcgcgcgc gcgccggtt tcgaaaccct ggtgctgacg    540
gtggacatcc cggtgtcggc caatcgcgaa acaacgtgc gcaccggctt ttccacgccg    600
ctcaagccca gctgcgggct ggcctgggac ggcgtcacgc gcccgcgctg gttggccggc    660 accttctctgc gcacgctgct caagcacggc atgccgcatt tcgagaattc cttcgccacg    720
cgcggcgcgc ccatcgtctc ggcctcggtg ctgcgcgact tcagcgcgcg cgaccacctg    780
aactgggaac acgtggcccg catccgccgg caatggcccg gcgcgctgat catcaagggc    840
atcctgcacc gcaggacgc ggcgctggcc cgcagccacg gcgccgacgg cgtcatcgtc    900
tcgaaccacg cggccgcca gctcgacggc gcgatctcgc cgctgcgcgc gctgcccggc    960
gtggtcgcgg ccgccggcga catgacggtg atgatggaca cggcatccg ccgcggcagc    1020 gacgtgctca aggccctggc gctgggcgcg cgccacgtgt tcgtgggccg ccccttcaac    1080
tatgcggcgg cggtcggcgg cgaggccggc gtggcgcacg ccatcggcct gctgcgcgcc    1140
gagatcgacc gcaacatggc catgctggga atcaatacat tgcgcgaaat ggacgcaggc    1200
ctgctggccc gcgagagcct ggcagat                                         1227
```

<210> SEQ ID NO 7
<211> LENGTH: 364
<212> TYPE: PRT
<213> ORGANISM: Bacillus sphaericus

<400> SEQUENCE: 7

```
Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
                20                  25                  30

Asp Thr Thr Leu Gly Pro Ala Leu Gly Gly Ala Arg Met Trp Thr Tyr
            35                  40                  45

Ala Thr Glu Glu Asn Ala Ile Glu Asp Ala Leu Arg Leu Ala Arg Gly
        50                  55                  60

Met Thr Tyr Lys Asn Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
                100                 105                 110

Gly Glu Asp Val Gly Thr Thr Val Thr Asp Met Asp Leu Ile His Glu
            115                 120                 125

Glu Thr Asn Tyr Val Thr Gly Ile Ser Pro Ala Phe Gly Ser Ser Gly
        130                 135                 140

Asn Pro Ser Pro Val Thr Ala Tyr Gly Val Tyr Arg Gly Met Lys Ala
145                 150                 155                 160
```

-continued

```
Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
    210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360
```

<210> SEQ ID NO 8
<211> LENGTH: 1095
<212> TYPE: DNA
<213> ORGANISM: Bacillus sphaericus

<400> SEQUENCE: 8

```
atggaaatct tcaagtatat ggaaaagtat gattatgaac aattggtatt ttgccaagac      60
gaagcatctg ggttaaaagc gattatcgct atccatgaca caacacttgg accagcatta     120
ggtggtgctc gtatgtggac ctacgcgaca gaagaaaatg cgattgagga tgcattaaga     180
ttagcacgcg ggatgacata taaaaatgca gctgctggtt taaaccttgg cggtggaaaa     240
acggtcatta ttggggaccc atttaaagat aaaaacgaag aaatgttccg tgctttaggt     300
cgtttcattc aaggattaaa cggtcgctat attaccggtg aagatgttgg tacaaccgta     360
acagatatgg atttaatcca tgaggaaaca aattacgtta caggtatatc gccagcgttt     420
ggttcatcgg gtaatccttc accagtaact gcttatggcg tttatcgtgg catgaaagca     480
gcggcgaaag aagcatttgg tacggatatg ctagaaggtc gtactatatc ggtacaaggg     540
ctaggaaacg tagcttacaa gctttgcgag tatttacata atgaaggtgc aaaacttgta     600
gtaacagata ttaaccaagc ggctattgat cgtgttgtca atgattttgg cgctacagca     660
gttgcacctg atgaaatcta ttcacaagaa gtcgatattt tctcaccgtg tgcacttggc     720
gcaattttaa atgacgaaac gattccgcaa ttaaaagcaa aagttattgc tggttctgct     780
aataaccaac tacaagattc acgacatgga gattatttac acgagctagg cattgtttat     840
gcacctgact atgtcattaa tgcaggtggt gtaataaatg tcgcggacga attatatggc     900
tataatcgtg aacgagcgtt gaaacgtgta gatggtattt acgatagtat tgaaaaaatc     960
```

```
tttgaaattt ccaaacgtga tagtattcca acatatgttg cggcaaatcg tttggcagaa    1020
gaacgtattg ctcgtgtagc gaaatcgcgt agtcagttct taaaaaatga aaaaaatatt    1080
ttgaacggcc gttaa                                                     1095

<210> SEQ ID NO 9
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 9
ccatatgagc cggctggacc gctgcctgtc                                     30

<210> SEQ ID NO 10
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 10
ggatccctat gccgggctgg ccggccgtat c                                   31

<210> SEQ ID NO 11
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 11
ccatatgaac tcaaagaaac tcttgtcgat ag                                  32

<210> SEQ ID NO 12
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 12
ggatccctaa gggcgcgaca cgatgaagtc g                                   31

<210> SEQ ID NO 13
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 13
ccatatgaca tccatccttc cgtccgtcac c                                   31

<210> SEQ ID NO 14
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 14
ggatccctaa tctgccaggc tctcgcgggc c                                   31
```

<210> SEQ ID NO 15
<211> LENGTH: 1176
<212> TYPE: DNA
<213> ORGANISM: Artificial Sequence
<220> FEATURE:
<223> OTHER INFORMATION: Polynucleotide encoding Oxidase

<400> SEQUENCE: 15

| | | | | |
|---|---|---|---|---|
| atgtctcgcc | tggaccgctg | tctgagcgtt | cgcgattttg | agcgtgaagc ccgtcgtatt | 60 |
| atgccgcgct | gcgtagaagg | ttatgtgtgt | ggtggtacgg | aagatggtgc atctctggcg | 120 |
| gagtctgtgc | gcgcgctggg | cgatgtgggc | ttccgtccgc | gtggcctgcg tgtagtggac | 180 |
| cagcgcaatt | ccaaagttga | gctgtacggt | cagacctacg | cgatgccggt cggtttcgcg | 240 |
| cctactggct | tctctgctat | cgttatgcac | gaatgcgatc | tggccctggc ccaggcggca | 300 |
| cagcatgcgg | aaatccctttt | tatcatctcc | ggcgcgtcca | gcgttccgct ggaacgtctg | 360 |
| caacaggcaa | ccggcaaacg | ctgttggtat | caggcgtacc | tgccgggcaa caccgaacgc | 420 |
| atcggtcgcc | tgctgggtcg | tctgcgtcag | gccgaaatcc | cggttctggt agttaccatc | 480 |
| gacacttgcg | tcggtgctaa | ccgcgagaac | ctgcaacgcc | tggcgttcac cgttccattc | 540 |
| aagatgtccg | cgagcgtagt | tctggacggc | ctgcgccacc | cgcgttggag cctgaacgta | 600 |
| ttcatgcgta | ctctgctggg | ctctggtgtt | ccgcgtttca | gcaacctgtg cgaagaaatt | 660 |
| ggcccaccaa | tcacccagga | cccgccaaac | ggcttccgtg | cgaacgtga caaactgtct | 720 |
| tgggagcaca | tccgttggat | cgtgaaaaac | tggcctggca | aactggttct gaaaggcgtg | 780 |
| atgcacccag | acgatgcgcg | tcaggcgtgt | gttgcaggtg | ctgacggtgt gatcgttagc | 840 |
| aatcatggtg | gtcgtcagct | ggatggctgc | atttctccgc | tgcaagcact gccggaaatt | 900 |
| gtagctgctg | tcccgccggg | ctttccggtg | atggttgatg | cggtttccg tcgtggttcc | 960 |
| gatgtcctga | aggctgttgc | tctgggcgct | cgtatggtgt | ttacgggtcg tccgcagctg | 1020 |
| ttcggtgccg | ctgtgggtgg | tcaggctggc | atccgtaaag | tcgcggcaat tttccgttct | 1080 |
| gaaatctcta | ccgacctggc | actgctgggt | tgctcctccc | tggcagatgt aactccggac | 1140 |
| ctgattgcac | cgatccgtcc | ggccagcccg | gcttaa | | 1176 |

<210> SEQ ID NO 16
<211> LENGTH: 1161
<212> TYPE: DNA
<213> ORGANISM: Artificial Sequence
<220> FEATURE:
<223> OTHER INFORMATION: Polynucleotide encoding Oxidase

<400> SEQUENCE: 16

| | | | | |
|---|---|---|---|---|
| atgaactcca | gaaaactgct | gtctatcggc | gactacgaac | gtgccgctaa agccgttctg | 60 |
| ccacacgcgg | tattcggtta | tgtgaacggt | ggcaccgaag | attgtctgac gctgcaagct | 120 |
| aaccgtgaag | cattccgtag | cgtacaattt | cgcccgcgcg | gtctggtagg tgtagcgcag | 180 |
| cgtactcagg | cggtggaact | gtgggtcgt | cagtaccgtc | acccgttcgg tatcgccccg | 240 |
| atgggtatga | ccgctatgtg | ccgtcatcgc | tgcgaatggg | atctggcaaa agctgcgagc | 300 |
| gaagcgaaga | tcccttttcgt | actgtctggt | ctgtccaccc | tggctatgga aaccgttcgc | 360 |
| caggcagatg | ccgacttctg | gtatcaggc | tacattccgg | cgataaaga tgttatcgaa | 420 |
| ccgctgctgc | gccgtctgcg | cgccaacgaa | gttgatgttc | tggttgtgac tatcgacacc | 480 |
| ccggtgggtg | ctaaccgcga | gaacaaccaa | cgcaacggct | tcaccatccc gttcaaattc | 540 |
| tccggcggtc | tgctgtggga | tggtctgcgt | caccgcgtt | ggtctgcaaa tgtcttcctg | 600 |

| | |
|---|---|
| cgtactctgc tgagcgaccg tcaggtgcca cgttttttgca acgtagtggc ggacacccgt | 660 |
| ggctaccgta tcactgaaga accgaaaggt ggcctgcgtg gtggccgtga tcgcctggat | 720 |
| tggtcccacc tggcgtggat gcgcgatatt tggccgggtc gcatcgtcct gaaaggcgtt | 780 |
| gcgcaccctg gtgacgcgca gctggctgaa cagatgggcc tggacggtgt gattgtgagc | 840 |
| aatcatggcg tcgtcagct ggatggcgca cagggtgctc tggacgctct gccggaggtt | 900 |
| gtcgcggctg ttggtccgaa cttcccggtc atggttgacg gtggctttcg tcgtggcgca | 960 |
| gacgttctga aagcaattgc gctgggtgcg cgtatggttt ttctgggtcg cccattcctg | 1020 |
| tacggcgcat ctgtggcggg ccaggctggt gtagcacgta tcattgacat tctgggcacg | 1080 |
| gagatcgacc gtaacctggg cctgctgggc tgtcgtgacc tggccgagct gggttctgac | 1140 |
| tttatcgttt ctcgtccgta a | 1161 |

<210> SEQ ID NO 17
<211> LENGTH: 1230
<212> TYPE: DNA
<213> ORGANISM: Artificial Sequence
<220> FEATURE:
<223> OTHER INFORMATION: Polynucleotide encoding Oxidase

<400> SEQUENCE: 17

| | |
|---|---|
| atgacctcta ttctgccttc tgttactgtt ccgggttctt ctccggcgga ggcttctcgc | 60 |
| ccgctgcctc gtgcactgca acgtatgctg tccctggacg attttgaggc tgctgcacgt | 120 |
| cgtcgcctgc cgcgcccgat tttcggttat atcgcaggcg ccgccgaaga taaccagtct | 180 |
| ctgcgtagca atcgcgaagc gttcggccgc tacgcattcg ctccgcgtgt actggttgac | 240 |
| gtatcccgtc gttctcagca gactgaactg ttcggccgtc gttacgcgag cccgttcggc | 300 |
| attgcgccga tgggtatctc tgctctgagc acctaccgtg gcgacatcgt actggctcgt | 360 |
| gcggcccgtg aacagggtat cccagctatc ctgtccggta cgtctctgat tccgctggaa | 420 |
| gacgtgattc gcgaagcacc gggcacctgg ttccaagcat atctgccggg tgatccacag | 480 |
| cgcatcgacg cactggtcga gcgcgcccgt cgtgcgggct cgagactctt ggtgctgacc | 540 |
| gttgacatcc cggtctccgc taaccgtgaa aacaacgttc gcaccggctt ctctaccccg | 600 |
| ctgaaaccga gcctgcgcct ggcatgggat ggcgtaactc gtccgcgttg gctggcaggt | 660 |
| acttttctgc gtaccctgct gaaacatggt atgccgcact cgaaaactc cttcgcgacc | 720 |
| cgtggcgcac cgatcgtgag cgcctccgtg ctgcgtgact ttagcgcacg tgaccacctg | 780 |
| aactgggaac acgttgctcg catccgtcgt cagtggccgg tgcactgat cattaagggt | 840 |
| attctgcacc ctcaggatgc cgctctggca cgttctcacg gtgctgatgg cgttatcgtt | 900 |
| tccaatcatg gtgccgtca gctggatggc gcgatctctc cactgcgtgc gctgccaggt | 960 |
| gttgtggcgg ctgcgggtga tatgaccgtg atgatggaca gcggtatccg tcgcggttct | 1020 |
| gatgtcctga agctctggc gctgggtgcc cgccatgttt tcgtgggtcg cccgtttaac | 1080 |
| tacgctgctg cggttggtgg cgaagcgggc gtagcccacg cgatcggtct gctgcgtgcc | 1140 |
| gaaattgacc gcaacatggc gatgctgggc atcaacacgc tgcgcgaaat ggatgcgggc | 1200 |
| ctgctggcgc gtgaatccct ggctgactaa | 1230 |

<210> SEQ ID NO 18
<211> LENGTH: 25
<212> TYPE: DNA
<213> ORGANISM: Artificial Sequence
<220> FEATURE:
<223> OTHER INFORMATION: Designed oligonucleotide primer for PCR

```
<400> SEQUENCE: 18
gccatggaaa tcttcaagta tatgg                                        25

<210> SEQ ID NO 19
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 19
gggcccgggt taacggccgt tcaaaatatt                                   30

<210> SEQ ID NO 20
<211> LENGTH: 27
<212> TYPE: DNA
<213> ORGANISM: Artificial Sequence
<220> FEATURE:
<223> OTHER INFORMATION: Designed oligonucleotide primer for mutagenesis

<400> SEQUENCE: 20
gtcgctatat taccggtgaa gatgttg                                      27

<210> SEQ ID NO 21
<211> LENGTH: 27
<212> TYPE: DNA
<213> ORGANISM: Artificial Sequence
<220> FEATURE:
<223> OTHER INFORMATION: Designed oligonucleotide primer for mutagenesis

<400> SEQUENCE: 21
caacatcttc accggtaata tagcgac                                      27

<210> SEQ ID NO 22
<211> LENGTH: 26
<212> TYPE: DNA
<213> ORGANISM: Artificial Sequence
<220> FEATURE:
<223> OTHER INFORMATION: Designed oligonucleotide primer for mutagenesis

<400> SEQUENCE: 22
gatagtattc caacctatgt tgcggc                                       26

<210> SEQ ID NO 23
<211> LENGTH: 26
<212> TYPE: DNA
<213> ORGANISM: Artificial Sequence
<220> FEATURE:
<223> OTHER INFORMATION: Designed oligonucleotide primer for mutagenesis

<400> SEQUENCE: 23
gccgcaacat aggttggaat actatc                                       26

<210> SEQ ID NO 24
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 24
gggcatatgg aaatcttcaa gtatatgg                                     28

<210> SEQ ID NO 25
```

```
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 25
ggatccttaa cggccgttca aaatatt                                              27

<210> SEQ ID NO 26
<211> LENGTH: 1206
<212> TYPE: DNA
<213> ORGANISM: Artificial Sequence
<220> FEATURE:
<223> OTHER INFORMATION: Polynucleotide encoding Formate Dehydrogenase

<400> SEQUENCE: 26
atggctaaga tcgtttgcgt tctgtacgat gacccggtta ccggttaccc taaaacttac          60
gcacgcgatg atctgccgaa atcgaatgc tatccggacg ccagaccct gccgaccca            120 cgtgcgattg acttccagcc gggtgctctg ctgggtagcg tatctggtga actgggtctg          180
cgtaaatacc tggaaagcaa cggccacgaa ctggtcgtta cctcttccaa agacggtgac          240
aattccgtac tggaccgtga actggcagat gcggaaattg ttatcagcca gccgttctgg          300
ccagcgtata tgacggctga acgtatcaag cgcgcgaaaa aactgaaaat gattgtgact          360
gcgggcattg ctccgacca cacgatctg caagcagcga tggaacacgg tatcaccgtg           420
gcagaagtta cttactgcaa ctccaactcc gtggcggaac atgttatgat gaccaccctg          480
gctctggtac gtaactacct gccatcctac cagtgggtac tgaaaggtgg ttggaacatc         540
gcagattgtg ttgaacgttc ttacgatctg gaaggcatgc acgtcggtac tgtagcggcc          600
ggtcgtattg gtctgcgtgt tctgcgcctg atgaaacctt cggtactca cctgcattat           660 ctggatcgtc accgcctgcc ggaatctgtg gagaaagagc tgaacctgac ccaccacact          720
tctctggagt ccctggcgaa agtgtgcgac gtggttacgc tgaactgccc gctgcacccg          780
gaaaccgaac acatgatcaa cgctgactcc ctgaaacatt ttaaacgcgg tgcgtacctg          840
atcaataccg cccgtggcaa actgtgtgac cgtgatgccg tcgcggcagc cctggaatct          900
ggccaactgg ccggctacgg cggcgacgtt tggtttccgc agccggcacc ggcggatcat         960
ccgtggcgta gcatgccgca ccacggtatg actccgcata ttagcggcac ctctctgtct         1020
gcccagaccc gttacgcggc tggcacccgc gagatcctgg aatgttattt cgagaaccgc        1080
ccgatccgta cgaatatct gatcgtgcag aacggcaagc tggctggtgt cggtgctcac         1140
agctattctg ctggtaacgc aactggcggc agcgaggaag ctgcacgttt caagaaatct         1200
gcttaa                                                                   1206

<210> SEQ ID NO 27
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 27
ccatatgtct cgcctggacc gctgtctgag                                           30

<210> SEQ ID NO 28
<211> LENGTH: 28
<212> TYPE: DNA
<213> ORGANISM: Artificial Sequence
```

```
<220> FEATURE:
<223> OTHER INFORMATION: Designed oligonucleotide primer for PCR

<400> SEQUENCE: 28
ggatccttaa gccgggctgg ccggacgg                                    28

<210> SEQ ID NO 29
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 29
ccatatgaac tccaagaaac tgctgtctat c                                31

<210> SEQ ID NO 30
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 30
ggatccttac ggacgagaaa cgataaag                                    28

<210> SEQ ID NO 31
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 31
ccatatgacc tctattctgc cttctgttac                                  30

<210> SEQ ID NO 32
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 32
actcgaggtc agccagggat tcacgcgcca g                                31

<210> SEQ ID NO 33
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 33
ccatatgagc acgtcagacg atatccataa c                                31

<210> SEQ ID NO 34
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 34
actcgagcag caggtcgaaa cggtcgaggt tc                               32
```

<210> SEQ ID NO 35
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 35
ccatatggct aagatcgttt gcgttctgta c                                31

<210> SEQ ID NO 36
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 36
actcgagagc agatttcttg aaacgtgcag                                  30

<210> SEQ ID NO 37
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 37
cggatccgag gaaacagacc atgg                                        24

<210> SEQ ID NO 38
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 38
ctcagagtta acggccgttc aaaatatt                                    28

<210> SEQ ID NO 39
<211> LENGTH: 364
<212> TYPE: PRT
<213> ORGANISM: Bacillus sphaericus

<400> SEQUENCE: 39

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
                20                  25                  30

Asp Thr Thr Leu Gly Pro Ala Leu Gly Gly Ala Arg Met Trp Thr Tyr
            35                  40                  45

Ala Thr Glu Glu Asn Ala Ile Glu Asp Ala Leu Arg Leu Ala Arg Gly
        50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
                100                 105                 110

Ala Glu Asp Val Gly Thr Thr Val Thr Asp Met Asp Leu Ile His Glu
            115                 120                 125

```
Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360

<210> SEQ ID NO 40
<211> LENGTH: 1095
<212> TYPE: DNA
<213> ORGANISM: Bacillus sphaericus

<400> SEQUENCE: 40
atggaaatct tcaagtatat ggaaaagtat gattatgaac aattggtatt ttgccaagac     60
gaagcatctg ggttaaaagc gattatcgct atccatgaca caacacttgg accagcatta    120
ggtggtgctc gtatgtggac ctacgcgaca gaagaaaatg cgattgagga tgcattaaga    180
ttagcacgcg ggatgacata taaaaatgca gctgctggtt taaaccttgg cggtggaaaa    240
acggtcatta ttggggaccc atttaaagat aaaaacgaag aaatgttccg tgctttaggt    300
cgtttcattc aaggattaaa cggtcgctat attaccgctg aagatgttgg tacaaccgta    360
acagatatgg atttaatcca tgaggaaaca aattacgtta caggtatatc gccagcgttt    420
ggttcatcgg gtaatccttc accagtaact gcttatggcg tttatcgtgg catgaaagca    480
gcggcgaaag aagcatttgg tacggatatg ctagaaggtc gtactatatc ggtacaaggg    540
ctaggaaacg tagcttacaa gctttgcgag tatttacata tgaaggtgca aaacttgta    600 gtaacagata ttaaccaagc ggctattgat cgtgttgtca atgattttgg cgctacagca    660
gttgcacctg atgaaatcta ttcacaagaa gtcgatattt tctcaccgtg tgcacttggc    720
gcaattttaa atgacgaaac gattccgcaa ttaaaagcaa aagttattgc tggttctgct    780
```

```
aataaccaac tacaagattc acgacatgga gattatttac acgagctagg cattgtttat    840
gcacctgact atgtcattaa tgcaggtggt gtaataaatg tcgcggacga attatatggc    900
tataatcgtg aacgagcgtt gaaacgtgta gatggtattt acgatagtat tgaaaaaatc    960
tttgaaattt ccaaacgtga tagtattcca acatatgttg cggcaaatcg tttggcagaa   1020
gaacgtattg ctcgtgtagc gaaatcgcgt agtcagttct taaaaaatga aaaaaatatt   1080
ttgaacggcc gttaa                                                    1095
```

<210> SEQ ID NO 41
<211> LENGTH: 726
<212> TYPE: PRT
<213> ORGANISM: Escherichia coli

<400> SEQUENCE: 41

```
Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

Pro Leu Asn Ser Trp Pro Asp Asn Val Ser Leu Asp Lys Ala Arg Arg
    130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
        195                 200                 205

Pro Glu Ala Leu Ala Lys Ala Pro Leu Gly Ala Thr Glu Met Gly Leu
    210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly Gly His Thr Leu Gly Lys Thr
            260                 265                 270

His Gly Ala Gly Pro Thr Ser Asn Val Gly Pro Asp Pro Glu Ala Ala
        275                 280                 285

Pro Ile Glu Glu Gln Gly Leu Gly Trp Ala Ser Thr Tyr Gly Ser Gly
    290                 295                 300

Val Gly Ala Asp Ala Ile Thr Ser Gly Leu Glu Val Val Trp Thr Gln
```

```
            305                 310                 315                 320
            Thr Pro Thr Gln Trp Ser Asn Tyr Phe Phe Glu Asn Leu Phe Lys Tyr
                        325                 330                 335

Glu Trp Val Gln Thr Arg Ser Pro Ala Gly Ala Ile Gln Phe Glu Ala
                        340                 345                 350

Val Asp Ala Pro Glu Ile Ile Pro Asp Pro Phe Asp Pro Ser Lys Lys
                        355                 360                 365

Arg Lys Pro Thr Met Leu Val Thr Asp Leu Thr Leu Arg Phe Asp Pro
                    370                 375                 380

Glu Phe Glu Lys Ile Ser Arg Arg Phe Leu Asn Asp Pro Gln Ala Phe
            385                 390                 395                 400

Asn Glu Ala Phe Ala Arg Ala Trp Phe Lys Leu Thr His Arg Asp Met
                            405                 410                 415

Gly Pro Lys Ser Arg Tyr Ile Gly Pro Glu Val Pro Lys Glu Asp Leu
                        420                 425                 430

Ile Trp Gln Asp Pro Leu Pro Gln Pro Ile Tyr Asn Pro Thr Glu Gln
                        435                 440                 445

Asp Ile Ile Asp Leu Lys Phe Ala Ile Ala Asp Ser Gly Leu Ser Val
                    450                 455                 460

Ser Glu Leu Val Ser Val Ala Trp Ala Ser Ala Ser Thr Phe Arg Gly
            465                 470                 475                 480

Gly Asp Lys Arg Gly Gly Ala Asn Gly Ala Arg Leu Ala Leu Met Pro
                                485                 490                 495

Gln Arg Asp Trp Asp Val Asn Ala Ala Ala Val Arg Ala Leu Pro Val
                        500                 505                 510

Leu Glu Lys Ile Gln Lys Glu Ser Gly Lys Ala Ser Leu Ala Asp Ile
                        515                 520                 525

Ile Val Leu Ala Gly Val Val Gly Val Glu Lys Ala Ala Ser Ala Ala
                    530                 535                 540

Gly Leu Ser Ile His Val Pro Phe Ala Pro Gly Arg Val Asp Ala Arg
            545                 550                 555                 560

Gln Asp Gln Thr Asp Ile Glu Met Phe Glu Leu Leu Glu Pro Ile Ala
                            565                 570                 575

Asp Gly Phe Arg Asn Tyr Arg Ala Arg Leu Asp Val Ser Thr Thr Glu
                        580                 585                 590

Ser Leu Leu Ile Asp Lys Ala Gln Gln Leu Thr Leu Thr Ala Pro Glu
                        595                 600                 605

Met Thr Ala Leu Val Gly Gly Met Arg Val Leu Gly Gly Asn Phe Asp
            610                 615                 620

Gly Ser Lys Asn Gly Val Phe Thr Asp Arg Val Gly Val Leu Ser Asn
            625                 630                 635                 640

Asp Phe Phe Val Asn Leu Leu Asp Met Arg Tyr Glu Trp Lys Ala Thr
                            645                 650                 655

Asp Glu Ser Lys Glu Leu Phe Glu Gly Arg Asp Arg Glu Thr Gly Glu
                        660                 665                 670

Val Lys Phe Thr Ala Ser Arg Ala Asp Leu Val Phe Gly Ser Asn Ser
                        675                 680                 685

Val Leu Arg Ala Val Ala Glu Val Tyr Ala Ser Ser Asp Ala His Glu
                    690                 695                 700

Lys Phe Val Lys Asp Phe Val Ala Ala Trp Val Lys Val Met Asn Leu
            705                 710                 715                 720

Asp Arg Phe Asp Leu Leu
                        725
```

<210> SEQ ID NO 42
<211> LENGTH: 2181
<212> TYPE: DNA
<213> ORGANISM: Escherichia coli

<400> SEQUENCE: 42

| | | | | | |
|---|---|---|---|---|---|
| atgagcacgt | cagacgatat | ccataacacc | acagccactg | gcaaatgccc | gttccatcag | 60 |
| ggcggtcacg | accagagtgc | ggggcgggc | acaaccactc | gcgactggtg | gccaaatcaa | 120 |
| cttcgtgttg | acctgttaaa | ccaacattct | aatcgttcta | acccactggg | tgaggacttt | 180 |
| gactaccgca | agaattcag | caaattagat | tactacggcc | tgaaaaaga | tctgaaagcc | 240 |
| ctgttgacag | aatctcaacc | gtggtggcca | gccgactggg | gcagttacgc | cggtctgttt | 300 |
| attcgtatgg | cctggcacgg | cgcggggact | taccgttcaa | tcgatggacg | cggtggcgcg | 360 |
| ggtcgtggtc | agcaacgttt | tgcaccgctg | aactcctggc | cggataacgt | aagcctcgat | 420 |
| aaagcgcgtc | gcctgttgtg | gccaatcaaa | cagaaatatg | gtcagaaaat | ctcctgggcc | 480 |
| gacctgttta | tcctcgcggg | taacgtggcg | ctagaaaact | ccggcttccg | taccttcggt | 540 |
| tttggtgccg | tcgtgaaga | cgtctgggaa | ccggatctgg | atgttaactg | ggtgatgaa | 600 |
| aaagcctggc | tgactcaccg | tcatccggaa | gcgctggcga | agcaccgct | gggtgcaacc | 660 |
| gagatgggtc | tgatttacgt | taacccggaa | ggcccggatc | acagcggcga | accgctttct | 720 |
| gcggcagcag | ctatccgcgc | gaccttcggc | aacatgggca | tgaacgacga | agaaaccgtg | 780 |
| gcgctgattg | cgggtggtca | tacgctgggt | aaaacccacg | gtgccggtcc | gacatcaaat | 840 |
| gtaggtcctg | atccagaagc | tgcaccgatt | gaagaacaag | gtttaggttg | ggcgagcact | 900 |
| tacggcagcg | gcgttggcgc | agatgccatt | acctctggtc | tggaagtagt | ctggaccagg | 960 |
| acgccgaccc | agtggagcaa | ctatttcttc | gagaacctgt | tcaagtatga | gtgggtacag | 1020 |
| acccgcagcc | cggctggcgc | aatccagttc | gaagcggtag | acgcaccgga | aattatcccg | 1080 |
| gatccgtttg | atccgtcgaa | gaaacgtaaa | ccgacaatgc | tggtgaccga | cctgacgctg | 1140 |
| cgttttgatc | ctgagttcga | gaagatctct | cgtcgtttcc | tcaacgatcc | gcaggcgttc | 1200 |
| aacgaagcct | ttgcccgtgc | ctggttcaaa | ctgacgcaca | gggatatggg | gccgaaatct | 1260 |
| cgctacatcg | gccggaagt | gccgaaagaa | gatctgatct | ggcaagatcc | gctgccgcag | 1320 |
| ccgatctaca | cccgaccga | gcaggacatt | atcgatctga | aattcgcgat | tgcggattct | 1380 |
| ggtctgtctg | ttagtgagct | ggtatcggtg | gcctgggcat | ctgcttctac | cttccgtggt | 1440 |
| ggcgacaaac | gcggtggtgc | caacggtgcg | cgtctgcat | taatgccgca | gcgcgactgg | 1500 |
| gatgtgaacg | ccgcagccgt | tcgtgctctg | cctgttctgg | agaaaatcca | gaaagagtct | 1560 |
| ggtaaagcct | cgctggcgga | tatcatagtg | ctggctggtg | tggttggtgt | tgagaaagcc | 1620 |
| gcaagcgccg | caggtttgag | cattcatgta | ccgtttgcgc | cgggtcgcgt | tgatgcgcgt | 1680 |
| caggatcaga | ctgacattga | gatgtttgag | ctgctggagc | caattgctga | cggtttccgt | 1740 |
| aactatcgcg | ctcgtctgga | cgtttccacc | accgagtcac | tgctgatcga | caaagcacag | 1800 |
| caactgacgc | tgaccgcgcc | ggaaatgact | gcgctggtgg | gcggcatgcg | tgtactgggt | 1860 |
| ggcaacttcg | atggcagcaa | aaacggcgtc | ttcactgacc | gcgttggcgt | attgagcaat | 1920 |
| gacttcttcg | tgaacttgct | ggatatgcgt | tacgagtgga | aagcgaccga | cgaatcgaaa | 1980 |
| gagctgttcg | aaggccgtga | ccgtgaaacc | ggcgaagtga | aatttacggc | cagccgtgcg | 2040 |
| gatctggtgt | ttggttctaa | ctccgtcctg | cgtgcggtgg | cggaagttta | cgccagtagc | 2100 |

```
gatgcccacg agaagtttgt taaagacttc gtggcggcat gggtgaaagt gatgaacctc      2160
gaccgtttcg acctgctgta a                                                2181
```

<210> SEQ ID NO 43
<211> LENGTH: 401
<212> TYPE: PRT
<213> ORGANISM: Bacillus sp.

<400> SEQUENCE: 43

```
Met Ala Lys Ile Val Cys Val Leu Tyr Asp Asp Pro Val Thr Gly Tyr
1               5                   10                  15

Pro Lys Thr Tyr Ala Arg Asp Asp Leu Pro Lys Ile Glu Cys Tyr Pro
            20                  25                  30

Asp Gly Gln Thr Leu Pro Thr Pro Arg Ala Ile Asp Phe Gln Pro Gly
        35                  40                  45

Ala Leu Leu Gly Ser Val Ser Gly Glu Leu Gly Leu Arg Lys Tyr Leu
    50                  55                  60

Glu Ser Asn Gly His Glu Leu Val Val Thr Ser Ser Lys Asp Gly Asp
65                  70                  75                  80

Asn Ser Val Leu Asp Arg Glu Leu Ala Asp Ala Glu Ile Val Ile Ser
                85                  90                  95

Gln Pro Phe Trp Pro Ala Tyr Met Thr Ala Glu Arg Ile Lys Arg Ala
            100                 105                 110

Lys Lys Leu Lys Met Ile Val Thr Ala Gly Ile Gly Ser Asp His Thr
        115                 120                 125

Asp Leu Gln Ala Ala Met Glu His Gly Ile Thr Val Ala Glu Val Thr
    130                 135                 140

Tyr Cys Asn Ser Asn Ser Val Ala Glu His Val Met Met Thr Thr Leu
145                 150                 155                 160

Ala Leu Val Arg Asn Tyr Leu Pro Ser Tyr Gln Trp Val Leu Lys Gly
                165                 170                 175

Gly Trp Asn Ile Ala Asp Cys Val Glu Arg Ser Tyr Asp Leu Glu Gly
            180                 185                 190

Met His Val Gly Thr Val Ala Ala Gly Arg Ile Gly Leu Arg Val Leu
        195                 200                 205

Arg Leu Met Lys Pro Phe Gly Thr His Leu His Tyr Leu Asp Arg His
    210                 215                 220

Arg Leu Pro Glu Ser Val Glu Lys Glu Leu Asn Leu Thr His His Thr
225                 230                 235                 240

Ser Leu Glu Ser Leu Ala Lys Val Cys Asp Val Val Thr Leu Asn Cys
                245                 250                 255

Pro Leu His Pro Glu Thr Glu His Met Ile Asn Ala Asp Ser Leu Lys
            260                 265                 270

His Phe Lys Arg Gly Ala Tyr Leu Ile Asn Thr Ala Arg Gly Lys Leu
        275                 280                 285

Cys Asp Arg Asp Ala Val Ala Ala Leu Glu Ser Gly Gln Leu Ala
    290                 295                 300

Gly Tyr Gly Gly Asp Val Trp Phe Pro Gln Pro Ala Pro Ala Asp His
305                 310                 315                 320

Pro Trp Arg Ser Met Pro His His Gly Met Thr Pro His Ile Ser Gly
                325                 330                 335

Thr Ser Leu Ser Ala Gln Thr Arg Tyr Ala Ala Gly Thr Arg Glu Ile
            340                 345                 350

Leu Glu Cys Tyr Phe Glu Asn Arg Pro Ile Arg Asn Glu Tyr Leu Ile
```

```
                355                 360                 365
Val Gln Asn Gly Lys Leu Ala Gly Val Gly Ala His Ser Tyr Ser Ala
        370                 375                 380

Gly Asn Ala Thr Gly Gly Ser Glu Glu Ala Ala Arg Phe Lys Lys Ser
385                 390                 395                 400

Ala

<210> SEQ ID NO 44
<211> LENGTH: 20
<212> TYPE: PRT
<213> ORGANISM: Artificial Sequence
<220> FEATURE:
<223> OTHER INFORMATION: Designed amino acid sequence

<400> SEQUENCE: 44

Met Gly Ser Ser His His His His His His Ser Ser Gly Leu Val Pro
1               5                   10                  15

Arg Gly Ser His
            20

<210> SEQ ID NO 45
<211> LENGTH: 8
<212> TYPE: PRT
<213> ORGANISM: Artificial Sequence
<220> FEATURE:
<223> OTHER INFORMATION: Designed amino acid sequence

<400> SEQUENCE: 45

Leu Glu His His His His His His
1               5
```